(12) United States Patent
Dunten et al.

(10) Patent No.: US 7,148,229 B2
(45) Date of Patent: Dec. 12, 2006

(54) SULFONAMIDE SUBSTITUTED XANTHINE DERIVATIVES

(75) Inventors: Peter W. Dunten, Mountain View, CA (US); Louise H. Foley, Fort Myers, FL (US); Nicholas J. S. Huby, Scotch Plains, NJ (US); Sherrie L. Pietranico-Cole, Montclair, NJ (US); Weiya Yun, Warren, NJ (US)

(73) Assignee: Hoffman-La Roche Inc., Nutley, NJ (US)

( * ) Notice: Subject to any disclaimer, the term of this patent is extended or adjusted under 35 U.S.C. 154(b) by 226 days.

(21) Appl. No.: 10/776,697

(22) Filed: Feb. 11, 2004

(65) Prior Publication Data

US 2004/0192708 A1    Sep. 30, 2004

Related U.S. Application Data

(60) Provisional application No. 60/536,561, filed on Jan. 15, 2004, provisional application No. 60/448,652, filed on Feb. 19, 2003.

(51) Int. Cl.
| | | |
|---|---|---|
| C07D 473/08 | (2006.01) | |
| C07D 473/04 | (2006.01) | |
| C07D 473/06 | (2006.01) | |
| A61K 31/522 | (2006.01) | |
| A61P 31/31 | (2006.01) | |

(52) U.S. Cl. .............. 514/263.21; 544/268; 544/267; 544/269; 544/270; 544/271; 544/310; 544/311; 514/263.2; 514/263.22; 514/263.23; 514/263.34; 546/311; 546/312

(58) Field of Classification Search ............ 544/268, 544/267, 269, 270, 271; 514/263.34, 263.23, 514/263.22, 263.2, 263.21

See application file for complete search history.

(56) References Cited

U.S. PATENT DOCUMENTS 5,670,498 A * 9/1997 Suzuki et al. .......... 514/211.15

FOREIGN PATENT DOCUMENTS

| WO | WO 01/77110 A | 10/2001 |
|---|---|---|
| WO | WO 03/106459 | 12/2003 |

OTHER PUBLICATIONS

Müller, C. E., Tetrahedron Letters, 32, pp. 6539-6540 (1991).
Müller, et al., J. Med. Chem., 36, pp. 3341-3349 (1993).
Papesch et al., J. Org. Chem., 16, pp. 1879-1890 (1951).
Müller et al., Synthesis, pp. 1295-1299 (1995).
Jacobson et al., J. Med. Chem., 36, pp. 1333-1342 (1993).
Kawashima et al., Chem. Pharm. Bull., 43, pp. 1132-1136 (1995).
Ishikawa et al., Heterocycles, 31, pp. 1641-1646 (1990).

* cited by examiner

*Primary Examiner*—Mark L. Berch
(74) *Attorney, Agent, or Firm*—George W. Johnston; Patricia S. Rocha-Tramaloni; Brian C. Remy

(57) ABSTRACT

The present invention is a sulfonamide substituted xanthine derivative of formula I:

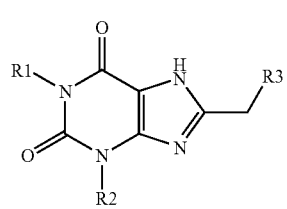

or a pharmaceutically acceptable salt thereof, wherein $R_1$ is lower alkyl, lower alkyl substituted by phenyl, or lower alkyl substituted by halogen substituted phenyl; $R_2$ is lower alkyl or lower alkyl substituted by lower cycloalkyl; and $R_3$ is:

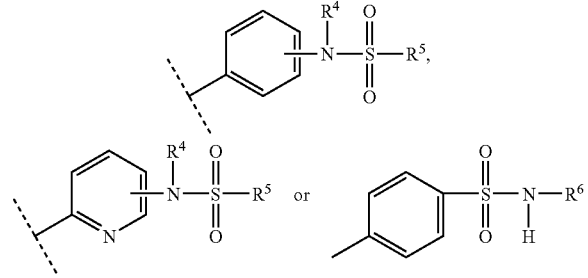

Compounds of formula I and pharmaceutically acceptable salts or prodrugs thereof show activity as modulators of gluconeogenesis.

103 Claims, No Drawings

SULFONAMIDE SUBSTITUTED XANTHINE DERIVATIVES

PRIORITY TO PROVISIONAL APPLICATION(S) UNDER 35 U.S.C. §119(e)

This application claims priority under 35 U.S.C. §119(e) of provisional application(s) Ser. No. 60/448,562, filed on Feb. 19, 2003 and Ser. No. 60/536,561, filed on Jan. 15, 2004.

FIELD OF THE INVENTION

The present invention is directed to sulfonamide substituted xanthine derivatives of formula I

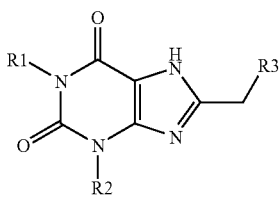

Compounds of formula I and pharmaceutically acceptable salts and prodrugs thereof are modulators of gluconeogenesis and are useful in the treatment of type 2 diabetes.

BACKGROUND OF THE INVENTION

The control of glucose production is one of the key aspects of anti-diabetic therapy. Type 2 diabetics have elevated levels of postprandial and fasting blood glucose (Consoli, A., Nurjhan, N., Capani, F. and Gerich, J. Diabetes 38, 550–7, 1989; Shulman, G I Am. J. Card. 84 (Suppl.1A): 3J–10J, 1999). Excessive hepatic glucose production (HGP) contributes to the fasting hyperglycemia observed in patients with Type 2 diabetes (T2D) (Gastadelli, A., Baldi S., Pettiti M., Toschi, E., Camastra, S., Natali, A., Landau, B. R. & Ferranini, E., Diabetes 49:1367–1373, 2000). Gluconeogenesis is believed to be the major pathway for this increased glucose production (Defronzo, R. A., Bonadonna, R. C. and Ferrannini, E., Diabetes Care 15:318–367, 1992).

Phosphoenolpyruvate carboxykinase (PEPCK) is a key regulatory enzyme in the gluconeogenic pathway. PEPCK is believed to be the flux controlling, rate limiting enzyme for this pathway (Cimbala, A. N., Lamers, W. H., Nelson, J. E., Monahan, J. E., Yoo-Warren, H., and Hanson R. W., J. Biol. Chem. 257:7629–7636, 1982), hence inhibition of this enzyme represents a novel way to improve glucose homeostasis. Previous attempts to control hepatic glucose production through inhibition of gluconeogeneis were limited to biguanides such as metformin, which inhibits HGP (Defronzo, R. A., Diabetes Reviews 6:89–131, 1998). Metformin has side effects such as gastrointestinal (GI) disturbances and lactic acidosis. Inhibition of PEPCK provides superior efficacy and, coupled with reduced side effects, represents a novel treatment for type 2 diabetes.

SUMMARY OF THE INVENTION

The present invention is directed to a compound of formula

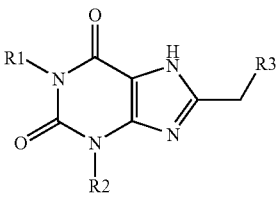

wherein
$R^1$ is selected from the group consisting of
  lower alkyl,
  lower alkyl substituted by phenyl and
  lower alkyl substituted by halogen substituted phenyl;
$R^2$ is selected from the group consisting of
  lower alkyl and
  lower alkyl substituted by lower cycloalkyl;
$R^3$ is selected from the group consisting of

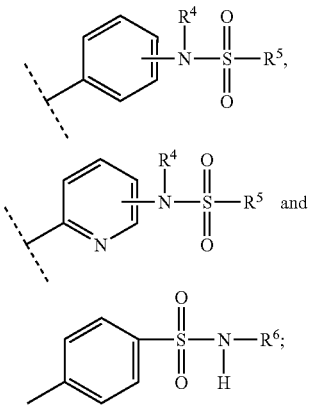

$R^4$ is selected from the group consisting of H and lower alkyl;
$R^5$ is selected from the group consisting of
  lower alkyl,
  amino lower alkyl,
  lower alkyl substituted by phenyl,
  lower alkenyl substituted by phenyl,
  phenyl,
  phenyl substituted by at least one substituent selected from the group consisting of lower alkyl, lower alkyl substituted by halogen, halogen, lower alkoxy, lower alkoxy substituted by halogen, nitro and acetamido,
  a 5-membered heteroaromatic ring having one heteroatom independently selected from the group consisting of N, O and S, the 5-membered heteroaromatic ring being unsubstituted or substituted by at least one substituent selected from the group consisting of lower alkyl, halogen, carboxy lower alkyl, amino, alkyl amino and acetamido,
  a 5-membered heteroaromatic ring having two heteroatoms wherein a first heteroatom is N and a second heteroatom is independently selected from the group consisting of N, O and S, the 5-membered heteroaromatic ring being unsubstituted or substituted by at least one substituent selected from the group consisting of lower alkyl, halogen, carboxy lower alkyl, amino, alkyl amino and acetamido, a 6-membered heteroaromatic ring having one N, the 6-membered heteroaromatic ring being unsubstituted or substituted by at least one substituent selected from the group consisting of lower alkyl, halogen, carboxy lower alkyl, amino, alkyl amino and acetamido,

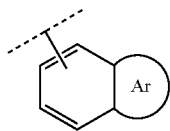

wherein Ar is selected from the group consisting of
a 5-membered heteroaromatic ring fused to the 6-membered ring, having one, two, or three heteroatoms, and wherein a first heteroatom is N, a second heteroatom is N and a third heteroatom is selected from the group consisting of O and S,
a 6-membered aromatic ring fused to the 6-membered ring, having no or one N heteroatoms, the fused 6-membered aromatic ring being unsubstituted or substituted by at least one substituent selected from the group consisting of lower alkyl, halogen, carboxy lower alkyl, amino, alkyl amino and acetamido; and
$R^6$ is selected from the group consisting of H,
a 5-membered aromatic heterocyclic ring with one or two heteroatoms wherein a first heteroatom is N and a second heteroatom is selected from the group consisting of N and S, the 5-membered heterocyclic ring being unsubstituted or substituted by at least one substituent selected from the group consisting of lower alkyl, halogen, carboxy lower alkyl, amino, alkyl amino and acetamido, and
a 6-membered aromatic heterocyclic ring with one or two N heteroatoms, the 6-membered heterocyclic ring being unsubstituted or substituted by at least one substituent selected from the group consisting of lower alkyl, halogen, carboxy lower alkyl, amino, alkyl amino and acetamido, or a pharmaceutically acceptable salt or prodrug thereof.

Phosphoenolpyruvate carboxykinase (PEPCK) is a key regulatory enzyme in the gluconeogenic pathway. As stated above, PEPCK is believed to be the flux controlling, rate limiting enzyme for this pathway, hence inhibition of this enzyme represents a novel way to improve glucose homeostasis. Previous attempts to control hepatic glucose production (HGP) through inhibition of gluconeogenesis were limited to biguanides such as metformin which inhibits HGP, but by an unknown mechanism. Inhibition of HGP by specifically targeting an enzyme, PEPCK, known to be in the gluconeogenic pathway, by administration of a therapeutically effective amount of a compound of formula I or a pharmaceutically effective salt thereof is an alternative therapy. In addition, inhibition of PEPCK by administration of a therapeutically effective amount of a compound of formula I provides superior efficacy and, coupled with reduced side effects, represents a novel treatment for type 2 (non-insulin dependent) diabetes.

The present invention is also directed to pharmaceutical compositions comprising a therapeutically effective amount of one or more compounds of formula I, or a pharmaceutically acceptable salt or prodrug thereof, and a pharmaceutically acceptable carrier or excipient.

The present invention is further directed to a method of treatment of type 2 diabetes comprising administering a therapeutically effective amount of a compound of formula I or a pharmaceutically acceptable salt or prodrug thereof to a patient in need of such treatment.

DETAILED DESCRIPTION OF THE INVENTION

The following definitions of the general terms used in the present description apply irrespective of whether the terms in question appear alone or in combination.

"Lower alkyl" refers to both straight chain and branched chain hydrocarbon groups having from one to seven carbon atoms, such as methyl, ethyl, propyl, butyl, isopropyl, isobutyl and the like. Preferred alkyl groups are methyl, ethyl, butyl and isopropyl. n-Butyl is particularly preferred.

The term "lower alkoxy" denotes a group wherein the alkyl residues are as defined above and which is attached via an oxygen atom.

"Lower alkenyl" refers to a hydrocarbon chain as defined for lower alkyl having at least one olefinic double bond, e.g., vinyl, allyl, butenyl and the like.

"Lower cycloalkyl" refers to cyclic saturated hydrocarbons having between three and seven carbon atoms, such as cyclopropyl, cyclobutyl, cyclopentyl and the like. Cyclopropyl, and cyclobutyl are preferred, with cyclopropyl being more preferred. These cycloalkyl groups may be unsubstituted or substituted with one or more substituents. Preferably, the cycloalkyl groups are unsubstituted. "Carboxy lower alkyl" refers to both straight chain and branched chain hydrocarbon groups having one to seven carbon atoms with at least one carbon possessing a carboxy group.

The term "unsubstituted" denotes that there are no other atoms attached to a chain or ring other than hydrogen. The term "substituted" as in substituted alkyl, substituted phenyl or substituted aromatic heterocycle, means that the substitution can occur at one or more positions and, unless otherwise indicated, that the substituent at each substitution site are independently selected from the specified options. The term "at least one" substituted means one, two, three, four or five substituents.

As used herein, the terms "halogen" means fluorine, chlorine, bromine and iodine. Preferred halogens are fluorine, chlorine and bromine.

Other chemical and structural terms used in the description are to be interpreted with their normal meaning in the art of organic chemistry. The terms "amino" and formula "—$NH_2$" may be used interchangeably.

The term "five-membered heteroaromatic ring" means a 5-membered aromatic ring with one heteroatom independently selected from the group consisting of nitrogen, sulfur and oxygen. Exemplary of these five-membered heteroaromatic ring moieties are furan, pyrrole and thiophen.

The term "6-membered heteroaromatic having one or two N heteroatoms", means pyridin with the ring attachment at the 2, 3, or 4 position or pyridazine, pyrimidine or pyrazine with the attachment point being adjacent to one or two N atoms.

The term "a 5-membered heteroaromatic ring having two heteroatoms wherein a first heteroatom is N and a second heteroatom is independently selected from the group consisting of N, O and S" means an aromatic ring with two heteroatoms, one of which is always N. Exemplary of these 5-membered heteroaromatic rings are oxazole, imidazole, thiazole, isoxazole, pyrazole, isothiazole and the like.

The term "5-membered heteroaromatic ring fused to the 6-membered ring, having one, two or three heteroatoms wherein a first heteroatom is N, a second heteroatom is N and a third heteroatom is selected from the group consisting of O and S. These examples include benzothiadiazole, benzoxadiazole, benzimidazole, benzopyrazole and the like.

The term "a 6-membered aromatic ring fused to the 6-membered ring, having no or one N heteroatoms" encompasses the moieties napthalene, quinoline and isoquinoline.

"Pharmaceutically acceptable salt" refers to conventional acid-addition salts or base-addition salts that retain the biological effectiveness and properties of the compounds of formula I and are formed from suitable non-toxic organic or inorganic acids or organic or inorganic bases. Exemplary acid-addition salts include those derived from inorganic acids such as hydrochloric acid, hydrobromic acid, hydroiodic acid, sulfuric acid, sulfamic acid, phosphoric acid and nitric acid, and those derived from organic acids such as p-toluenesulfonic acid, salicylic acid, trifluoroacetic acid, acetic acid, methanesulfonic acid, oxalic acid, succinic acid, citric acid, malic acid, lactic acid, fumaric acid, and the like. Exemplary base-addition salts include those derived from ammonium, potassium, sodium and, quaternary ammonium hydroxides, such as for example, tetramethylammonium hydroxide. The chemical modification of a pharmaceutical compound (i.e., drug) into a salt is a technique well known to pharmaceutical chemists to obtain improved physical and chemical stability, hygroscopicity, flowability and solubility of compounds. See, e.g., H. Ansel et. al., Pharmaceutical Dosage Forms and Drug Delivery Systems (6th Ed. 1995) at pp. 196 and 1456–1457.

"Prodrug" means a compound that may be converted, under physiological conditions or by solvolysis, to a pharmaceutically active compound. A prodrug may be inactive when administered to a subject but is converted in vivo to an active compound. That is, a prodrug may be an inactive species in in vitro cell based assays, but converted to an active species in vivo in the subject.

"Therapeutically effective amount" means an amount that is effective to prevent, alleviate or ameliorate symptoms of disease or prolong the survival of the subject being treated. Determination of a therapeutically effective amount is within the skill in the art.

In one embodiment, the present invention is directed to a compound of formula

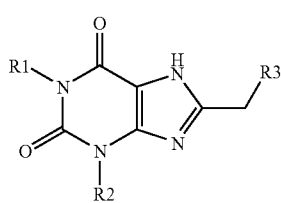

I wherein, $R^1$ is selected from the group consisting of
  lower alkyl,
  lower alkyl substituted by phenyl and
  lower alkyl substituted by halogen substituted phenyl;
$R^2$ is selected from the group consisting of
  lower alkyl and
  lower alkyl substituted by lower cycloalkyl;

$R^3$ is selected from the group consisting of

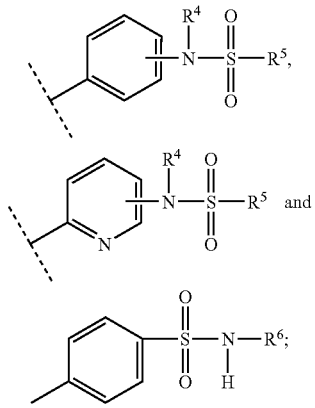

$R^4$ is selected from the group consisting of H and lower alkyl;
$R^5$ is selected from the group consisting of
  lower alkyl,
  amino lower alkyl,
  lower alkyl substituted by phenyl,
  lower alkenyl substituted by phenyl,
  phenyl,
  phenyl substituted by at least one substituent selected from the group consisting of lower alkyl, lower alkyl substituted by halogen, halogen, lower alkoxy, lower alkoxy substituted by halogen, nitro and acetamido,
  a 5-membered heteroaromatic ring having one heteroatom independently selected from the group consisting of N, O and S, the 5-membered heteroaromatic ring being unsubstituted or substituted by at least one substituent selected from the group consisting of lower alkyl, halogen, carboxy lower alkyl, amino, alkyl amino and acetamido,
  a 5-membered heteroaromatic ring having two heteroatoms wherein a first heteroatom is N and a second heteroatom is independently selected from the group consisting of N, O and S, the 5-membered heteroaromatic ring being unsubstituted or substituted by at least one substituent selected from the group consisting of lower alkyl, halogen, carboxy lower alkyl, amino, alkyl amino and acetamido,
  a 6-membered heteroaromatic ring having one N, the 6-membered heteroaromatic ring being unsubstituted or substituted by at least one substituent selected from the group consisting of lower alkyl, halogen, carboxy lower alkyl, amino, alkyl amino and acetamido,

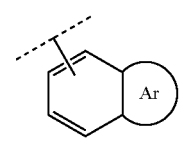

wherein Ar is selected from the group consisting of
    a 5-membered heteroaromatic ring fused to the 6-membered ring, having one, two, or three heteroatoms, and wherein a first heteroatom is N, a second heteroatom is N and a third heteroatom is selected from the group consisting of O and S and
    a 6-membered aromatic ring fused to the 6-membered ring, having no or one N heteroatoms, the fused 6-membered aromatic ring being unsubstituted or substituted by at least one substituent selected from the group consisting of lower alkyl, halogen, carboxy lower alkyl, amino, alkyl amino and acetamido; and $R^6$ is selected from the group consisting of H,
- a 5-membered aromatic heterocyclic ring with one or two heteroatoms wherein a first heteroatom is N and a second heteroatom is selected from the group consisting of N and S, the 5-membered heterocyclic ring being unsubstituted or substituted by at least one substituent selected from the group consisting of lower alkyl, halogen, carboxy lower alkyl, amino, alkyl amino and acetamido, and
- a 6-membered aromatic heterocyclic ring with one or two N heteroatoms, the 6-membered heterocyclic ring being unsubstituted or substituted by at least one substituent selected from the group consisting of lower alkyl, halogen, carboxy lower alkyl, amino, alkyl amino and acetamido, or a pharmaceutically acceptable salt or prodrug thereof.

In one preferred embodiment of a compound of formula I of the present invention, R1 is lower alkyl substituted by phenyl and R2 is lower alkyl. An exemplary compound of this preferred compound of formula I is selected from the group consisting of
4-(1-benzyl-3-butyl-2,6-dioxo-2,3,6,7-tetrahydro-1H-purin-8-ylmethyl)-benzenesulfonamide;
N-[4-(1-benzyl-3-butyl-2,6-dioxo-2,3,6,7-tetrahydro-1H-purin-8-ylmethyl)-phenyl]-4-methyl-benzenesulfonamide; and
N-[4-(1-benzyl-3-butyl-2,6-dioxo-2,3,6,7-tetrahydro-1H-purin-8-ylmethyl)-phenyl]-methanesulfonamide.

Another preferred compound of formula I has the structure

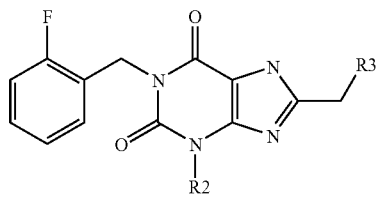

IA

A preferred compound of formula IA is where $R^2$ is lower alkyl. A more preferred compound of formula IA is where $R^2$ is lower alkyl, i.e., n-butyl and $R^3$ is

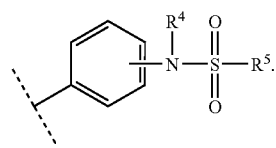

In this embodiment, $R^4$ preferably is H and $R^5$ is a 5-membered heteroaromatic ring having one heteroatom independently selected from the group consisting of N, O and S, with the 5-membered heteroaromatic ring being unsubstituted or substituted by at least one substituent selected from the group consisting of lower alkyl, halogen, carboxy lower alkyl, amino, alkyl amino and acetamido. An exemplary compound of these preferred compounds of formula IA is selected from the group consisting of 1-Methyl-1H-imidazole-4-sulfonic acid {4-[3-butyl-1-(2-fluoro-benzyl)-2,6-dioxo-2,3,6,7-tetrahydro-1H-purin-8-ylmethyl]-phenyl}-amide trifluoroacetic acid salt; and
5-chloro-1,3-dimethyl-1H-pyrazole-4-sulfonic acid {4-[3-butyl-1-(2-fluoro-benzyl)-2,6-dioxo-2,3,6,7-tetrahydro-1H-purin-8-ylmethyl]-phenyl}-amide.

Another preferred compound of formula IA is where $R^2$ is n-butyl and $R^5$ is a 6-membered heteroaromatic ring having one N, with the 6-membered heteroaromatic ring being unsubstituted or substituted by at least one substituent selected from the group consisting of lower alkyl, halogen, carboxy lower alkyl, amino, alkyl amino and acetamido. Exemplary of these compounds of formula IA is 6-chloro-pyridine-3-sulfonic acid {4-[3-butyl-1-(2-fluoro-benzyl)-2,6-dioxo-2,3,6,7-tetrahydro-1H-purin-8-ylmethyl]-phenyl}-amide.

Another preferred compound of formula IA wherein $R^2$ is n-butyl is where $R^5$ is

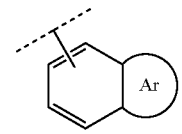

and Ar is selected from the group consisting of
a 5-membered heteroaromatic ring fused to the 6-membered ring, having one, two, or three heteroatoms, and wherein a first heteroatom is N, a second heteroatom is N and a third heteroatom is selected from the group consisting of O and S and
a 6-membered aromatic ring fused to the 6-membered ring, having no or one N heteroatoms, the fused 6-membered aromatic ring being unsubstituted or substituted by at least one substituent selected from the group consisting of lower alkyl, halogen, carboxy lower alkyl, amino, alkyl amino and acetamido.

A compound representative of these preferred compounds is selected from the group consisting of
N-{4-[3-butyl-1-(2-fluoro-benzyl)-2,6-dioxo-2,3,6,7-tetrahydro-1H-purin-8-ylmethyl]-phenyl}-1-naphthalenesulfonamide;
5-dimethylamino-naphthalene-1-sulfonic acid {4-[3-butyl-1-(2-fluoro-benzyl)-2,6-dioxo-2,3,6,7-tetrahydro-1H-purin-8-ylmethyl]-phenyl}-amide;
benzo[1,2,5]thiadiazole-4-sulfonic acid {4-[3-butyl-1-(2-fluoro-benzyl)-2,6-dioxo-2,3,6,7-tetrahydro-1H-purin-8-ylmethyl]-phenyl}-amide; and
benzo[1,2,5]oxadiazole-4-sulfonic acid {4-[3-butyl-1-(2-fluoro-benzyl)-2,6-dioxo-2,3,6,7-tetrahydro-1H-purin-8-ylmethyl]-phenyl}-amide.

Another preferred compound of formula IA is where $R^2$ is n-butyl and $R^5$ is lower alkyl or lower alkyl substituted by phenyl. A compound representative of this preferred compound selected from the group consisting of
propane-2-sulfonic acid {4-[3-butyl-1-(2-fluoro-benzyl)-2,6-dioxo-2,3,6,7-tetrahydro-1H-purin-8-ylmethyl]-phenyl}-amide;
N-{4-[3-butyl-1-(2-fluoro-benzyl)-2,6-dioxo-2,3,6,7-tetrahydro-1H-purin-8-ylmethyl]-phenyl}-C-phenyl-methanesulfonamide; and
ethanesulfonic acid {4-[3-butyl-1-(2-fluoro-benzyl)-2,6-dioxo-2,3,6,7-tetrahydro-1H-purin-8-ylmethyl]-phenyl}-amide.

Yet another preferred compound of formula IA is where $R^2$ is n-butyl and $R^5$ is lower alkenyl substituted by phenyl. A compound representative of this preferred embodiment is 2-phenyl-ethenesulfonic acid {4-[3-butyl-1-(2-fluoro-benzyl)-2,6-dioxo-2,3,6,7-tetrahydro-1H-purin-8-ylmethyl]-phenyl}-amide.

Another preferred compound of formula IA is where $R^2$ is n-butyl and $R^5$ is phenyl. Representative of this compound is N-{4-[3-butyl-1-(2-fluoro-benzyl)-2,6-dioxo-2,3,6,7-tetrahydro-1H-purin-8-ylmethyl]-phenyl}-benzenesulfonamide.

A further preferred compound of formula IA wherein $R^2$ is n-butyl is where $R^5$ is phenyl substituted by at least one substituent selected from the group consisting of lower alkyl, lower alkyl substituted by halogen, halogen, lower alkoxy, lower alkoxy substituted by halogen, nitro and acetamido.

A preferred compound of formula IA is where $R^2$ is n-butyl and $R^5$ is phenyl substituted by one substituent on the phenyl selected from the group consisting of lower alkyl, lower alkyl substituted by halogen, halogen, lower alkoxy, lower alkoxy substituted by halogen, nitro and acetamido.

A more preferred compound of this embodiment is where the one substituent is halogen. A compound representative of the preferred compound wherein the phenyl has one halogen substituent is selected from the group consisting of N-{4-[3-butyl-1-(2-fluoro-benzyl)-2,6-dioxo-2,3,6,7-tetrahydro-1H-purin-8-ylmethyl]-phenyl}-4-chloro-benzenesulfonamide;

N-{4-[3-butyl-1-(2-fluoro-benzyl)-2,6-dioxo-2,3,6,7-tetrahydro-1H-purin-8-ylmethyl]-phenyl}-4-iodo-benzenesulfonamide;

N-{4-[3-butyl-1-(2-fluoro-benzyl)-2,6-dioxo-2,3,6,7-tetrahydro-1H-purin-8-ylmethyl]-phenyl}-2-chloro-benzenesulfonamide;

N-{4-[3-butyl-1-(2-fluoro-benzyl)-2,6-dioxo-2,3,6,7-tetrahydro-1H-purin-8-ylmethyl]-phenyl}-3-chloro-benzenesulfonamide;

N-{4-[3-butyl-1-(2-fluoro-benzyl)-2,6-dioxo-2,3,6,7-tetrahydro-1H-purin-8-ylmethyl]-phenyl}-4-fluoro-benzenesulfonamide;

N-{4-[3-butyl-1-(2-fluoro-benzyl)-2,6-dioxo-2,3,6,7-tetrahydro-1H-purin-8-ylmethyl]-phenyl}-2-fluoro-benzenesulfonamide; and N-{4-[3-butyl-1-(2-fluoro-benzyl)-2,6-dioxo-2,3,6,7-tetrahydro-1H-purin-8-ylmethyl]-phenyl}-4-bromo-benzenesulfonamide.

Another preferred embodiment of formula IA is where $R^2$ is n-butyl and where $R^5$ is phenyl substituted by one substituent selected from the group lower alkyl and lower alkyl substituted by halogen. Representative of this preferred embodiment of formula IA is a compound selected from the group N-{4-[3-butyl-1-(2-fluoro-benzyl)-2,6-dioxo-2,3,6,7-tetrahydro-1H-purin-8-ylmethyl]-phenyl}-3-trifluoromethyl-benzenesulfonamide;

N-{4-[3-butyl-1-(2-fluoro-benzyl)-2,6-dioxo-2,3,6,7-tetrahydro-1H-purin-8-ylmethyl]-phenyl}-4-isopropyl-benzenesulfonamide;

N-{4-[3-butyl-1-(2-fluoro-benzyl)-2,6-dioxo-2,3,6,7-tetrahydro-1H-purin-8-ylmethyl]-phenyl}-3-methyl-benzenesulfonamide;

N-{4-[3-butyl-1-(2-fluoro-benzyl)-2,6-dioxo-2,3,6,7-tetrahydro-1H-purin-8-ylmethyl]-phenyl}-2-trifluoromethyl-benzenesulfonamide;

N-{4-[3-butyl-1-(2-fluoro-benzyl)-2,6-dioxo-2,3,6,7-tetrahydro-1H-purin-8-ylmethyl]-phenyl}-4-ethyl-benzenesulfonamide;

N-{4-[3-butyl-1-(2-fluoro-benzyl)-2,6-dioxo-2,3,6,7-tetrahydro-1H-purin-8-ylmethyl]-phenyl}-2-methyl-benzenesulfonamide; and N-{4-[3-butyl-1-(2-fluoro-benzyl)-2,6-dioxo-2,3,6,7-tetrahydro-1H-purin-8-ylmethyl]-phenyl}-4-trifluoromethyl-benzenesulfonamide.

Another preferred compound of formula IA is where $R^2$ is n-butyl and $R^5$ is phenyl substituted by two substituents selected from the group consisting of lower alkyl, lower alkyl substituted by halogen, halogen, lower alkoxy, lower alkoxy substituted by halogen, nitro and acetamido.

In one more preferred embodiment, these two substituents are halogen. A further more preferred embodiment is when the two halogen substituents are chloro.

Representative of the preferred compound when the two halogen substituents are chloro is a compound selected from the group consisting of N-{4-[3-butyl-1-(2-fluoro-benzyl)-2,6-dioxo-2,3,6,7-tetrahydro-1H-purin-8-ylmethyl]-phenyl}-2,4-dichloro-benzenesulfonamide;

N-{4-[3-butyl-1-(2-fluoro-benzyl)-2,6-dioxo-2,3,6,7-tetrahydro-1H-purin-8-ylmethyl]-phenyl}-2,5-dichloro-benzenesulfonamide;

N-{4-[3-butyl-1-(2-fluoro-benzyl)-2,6-dioxo-2,3,6,7-tetrahydro-1H-purin-8-ylmethyl]-phenyl}-2,6-dichloro-benzenesulfonamide;

N-{4-[3-butyl-1-(2-fluoro-benzyl)-2,6-dioxo-2,3,6,7-tetrahydro-1H-purin-8-ylmethyl]-phenyl}-2,3-dichloro-benzenesulfonamide;

N-{4-[3-butyl-1-(2-fluoro-benzyl)-2,6-dioxo-2,3,6,7-tetrahydro-1H-purin-8-ylmethyl]-phenyl}-3,5-dichloro-benzenesulfonamide; and N-{4-[3-butyl-1-(2-fluoro-benzyl)-2,6-dioxo-2,3,6,7-tetrahydro-1H-purin-8-ylmethyl]-phenyl}-3,4-dichloro-benzenesulfonamide.

Another preferred embodiment of the compound of formula IA is where $R^2$ is n-butyl and $R^5$ is phenyl substituted by two halogen substituents, and particularly when one of the halogen substituents is chloro and the other of the halogen substituents is fluoro. A compound exemplary of this preferred embodiment is selected from the group consisting of N-{4-[3-butyl-1-(2-fluoro-benzyl)-2,6-dioxo-2,3,6,7-tetrahydro-1H-purin-8-ylmethyl]-phenyl}-2-chloro-4-fluoro-benzenesulfonamide; and N-{4-[3-butyl-1-(2-fluoro-benzyl)-2,6-dioxo-2,3,6,7-tetrahydro-1H-purin-8-ylmethyl]-phenyl}-3-chloro-4-fluoro-benzenesulfonamide.

Another preferred compound of formula IA is where $R^2$ is n-butyl and $R^5$ is phenyl substituted by two halogen substituents, particularly when both of the halogen substituents are fluoro. A compound exemplary of this preferred compound is selected from the group consisting of N-{4-[3-butyl-1-(2-fluoro-benzyl)-2,6-dioxo-2,3,6,7-tetrahydro-1H-purin-8-ylmethyl]-phenyl}-2,4-difluoro-benzenesulfonamide;

N-{4-[3-butyl-1-(2-fluoro-benzyl)-2,6-dioxo-2,3,6,7-tetrahydro-1H-purin-8-ylmethyl]-phenyl}-2,6-difluoro-benzenesulfonamide; and N-{4-[3-butyl-1-(2-fluoro-benzyl)-2,6-dioxo-2,3,6,7-tetrahydro-1H-purin-8-ylmethyl]-phenyl}-3,4-difluoro-benzenesulfonamide.

Yet another preferred compound of formula IA is where $R^2$ is n-butyl and $R^5$ is phenyl substituted by two substituents selected from the group consisting of lower alkyl, lower alkyl substituted by halogen, halogen, lower alkoxy, lower alkoxy substituted by halogen, nitro and acetamido, particularly where one of the two phenyl substituents is halogen and the other phenyl substituent is lower alkyl. A compound exemplary of this preferred compound is selected from the group consisting of N-{4-[3-butyl-1-(2-fluoro-benzyl)-2,6-dioxo-2,3,6,7-tetrahydro-1H-purin-8-ylmethyl]-phenyl}-3-chloro-4-methyl-benzenesulfonamide;

N-{4-[3-butyl-1-(2-fluoro-benzyl)-2,6-dioxo-2,3,6,7-tetrahydro-1H-purin-8-ylmethyl]-phenyl}-3-chloro-2-methyl-benzenesulfonamide;

N-{4-[3-butyl-1-(2-fluoro-benzyl)-2,6-dioxo-2,3,6,7-tetrahydro-1H-purin-8-ylmethyl]-phenyl}-2-chloro-6-methyl-benzenesulfonamide; and N-{4-[3-butyl-1-(2-fluoro-benzyl)-2,6-dioxo-2,3,6,7-tetrahydro-1H-purin-8-ylmethyl]-phenyl}-5-fluoro-2-methyl-benzenesulfonamide.

Yet another preferred compound of formula IA is where $R_2$ is n-butyl and $R^5$ is phenyl substituted by two substituents selected from the group consisting of lower alkyl, lower alkyl substituted by halogen, halogen, lower alkoxy, lower alkoxy substituted by halogen, nitro and acetamido, particularly wherein the two phenyl substituents are selected from the group consisting of lower alkyl, lower alkoxyl and nitro. A compound exemplary of this preferred embodiment is selected from the group consisting of N-{4-[3-butyl-1-(2-fluoro-benzyl)-2,6-dioxo-2,3,6,7-tetrahydro-1H-purin-8-ylmethyl]-phenyl}-2,5-dimethoxy-benzenesulfonamide;

N-{4-[3-butyl-1-(2-fluoro-benzyl)-2,6-dioxo-2,3,6,7-tetrahydro-1H-purin-8-ylmethyl]-phenyl}-2-methoxy-5-methyl-benzenesulfonamide;

N-{4-[3-butyl-1-(2-fluoro-benzyl)-2,6-dioxo-2,3,6,7-tetrahydro-1H-purin-8-ylmethyl]-phenyl}-3,4-dimethoxy-benzenesulfonamide;

N-{4-[3-Butyl-1-(2-fluoro-benzyl)-2,6-dioxo-2,3,6,7-tetrahydro-1H-purin-8-ylmethyl]-phenyl}-2,5-dimethyl-benzenesulfonamide; and N-{4-[3-butyl-1-(2-fluoro-benzyl)-2,6-dioxo-2,3,6,7-tetrahydro-1H-purin-8-ylmethyl]-phenyl}-2-methyl-5-nitro-benzenesulfonamide.

A further preferred compound of formula IA is where $R^2$ is n-butyl and $R^5$ is phenyl substituted by three substituents selected from the group consisting of lower alkyl, lower alkyl substituted by halogen, halogen, lower alkoxy, lower alkoxy substituted by halogen, nitro and acetamido. A more preferred compound with three substituents on the phenyl is where the three substituents are selected from lower alkyl and halogen. A compound representative of this preferred compound is selected from the group consisting of N-{4-[3-butyl-1-(2-fluoro-benzyl)-2,6-dioxo-2,3,6,7-tetrahydro-1H-purin-8-ylmethyl]-phenyl}-2,4,6-trimethyl-benzenesulfonamide;

N-{4-[3-butyl-1-(2-fluoro-benzyl)-2,6-dioxo-2,3,6,7-tetrahydro-1H-purin-8-ylmethyl]-phenyl}-4-chloro-2,5-dimethyl-benzenesulfonamide;

N-{4-[3-butyl-1-(2-fluoro-benzyl)-2,6-dioxo-2,3,6,7-tetrahydro-1H-purin-8-ylmethyl]-phenyl}-2,4-dichloro-6-methyl-benzenesulfonamide; and N-{4-[3-butyl-1-(2-fluoro-benzyl)-2,6-dioxo-2,3,6,7-tetrahydro-1H-purin-8-ylmethyl]-phenyl}-C-phenyl-methanesulfonamide.

A further preferred compound of formula IA is where $R^2$ is n-butyl and $R^5$ is phenyl substituted by four substituents selected from the group consisting of lower alkyl, lower alkyl substituted by halogen, halogen, lower alkoxy, lower alkoxy substituted by halogen, nitro and acetamido. A more preferred compound with four substituents on the phenyl is where the four substituents are selected from lower alkyl and halogen. A compound exemplary of this preferred compound is selected from the group consisting of N-{4-[3-butyl-1-(2-fluoro-benzyl)-2,6-dioxo-2,3,6,7-tetrahydro-1H-purin-8-ylmethyl]-phenyl}-2,3,5,6-tetramethyl-benzenesulfonamide; and N-{4-[3-butyl-1-(2-fluoro-benzyl)-2,6-dioxo-2,3,6,7-tetrahydro-1H-purin-8-ylmethyl]-phenyl}-4-methoxy-2,3,6-trimethyl-benzenesulfonamide.

Another preferred compound of formula IA is where $R^2$ is n-butyl, $R^3$ is

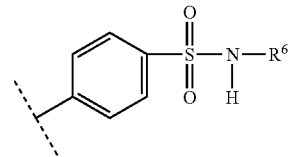

and $R^6$ is a 5-membered aromatic heterocyclic ring with one or two heteroatoms wherein a first heteroatom is N and a second heteroatom is selected from the group consisting of N and S, the 5-membered heterocyclic ring being unsubstituted or substituted by at least one substituent selected from the group consisting of lower alkyl, halogen, carboxy lower alkyl, amino, alkyl amino and acetamido. A compound representative of this preferred compound is selected from the group consisting of 4-[3-butyl-1-(2-fluoro-benzyl)-2,6-dioxo-2,3,6,7-tetrahydro-1H-purin-8-ylmethyl]-N-(1,3,5-trimethyl-1H-pyrazol-4-yl)-benzenesulfonamide; and 4-[3-butyl-1-(2-fluoro-benzyl)-2,6-dioxo-2,3,6,7-tetrahydro-1H-purin-8-ylmethyl]-N-thiazol-2-yl-benzenesulfonamide.

Another preferred compound of formula IA is where $R^2$ is n-butyl, $R^3$ is

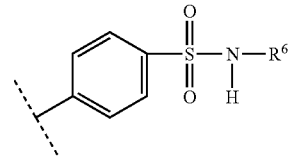

and $R^6$ is a 6-membered aromatic heterocyclic ring with one or two N heteroatoms, the 6-membered heterocyclic ring being unsubstituted or substituted by at least one substituent selected from the group consisting of lower alkyl, halogen, carboxy lower alkyl, amino, alkyl amino and acetamido. A compound exemplary of this preferred compound is selected from the group consisting of 4-[3-butyl-1-(2-fluoro-benzyl)-2,6-dioxo-2,3,6,7-tetrahydro-1H-purin-8-ylmethyl]-N-pyridin-2-yl-benzenesulfonamide;

4-[3-butyl-1-(2-fluoro-benzyl)-2,6-dioxo-2,3,6,7-tetrahydro-1H-purin-8-ylmethyl]-N-pyridin-3-yl-benzenesulfonamide;

4-[3-butyl-1-(2-fluoro-benzyl)-2,6-dioxo-2,3,6,7-tetrahydro-1H-purin-8-ylmethyl]-N-pyridin-4-yl-benzenesulfonamide;

4-[3-butyl-1-(2-fluoro-benzyl)-2,6-dioxo-2,3,6,7-tetrahydro-1H-purin-8-ylmethyl]-N-pyrimidin-2-yl-benzenesulfonamide; and 4-[3-butyl-1-(2-fluoro-benzyl)-2,6-dioxo-2,3,6,7-tetrahydro-1H-purin-8-ylmethyl]-N-(1,3,5-trimethyl-1H-pyrazol-4-yl)-benzenesulfonamide.

Another preferred compound of formula 1A is where $R^2$ is n-butyl, $R^3$ is

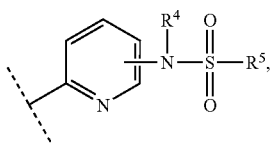

$R^4$ is H and $R^5$ is a 5-membered aromatic heterocyclic ring with one or two heteroatoms where a first heteroatom is N and a second heteroatom is selected from the group consisting of N and S, the 5-membered heterocyclic ring being unsubstituted or substituted by at least one substituent selected from the group consisting of lower alkyl, halogen, carboxy lower alkyl, amino, alkyl amino and acetamido. Representative of this preferred compound is 5-chloro-1,3-dimethyl-1H-pyrazole-4-sulfonic acid {6-[3-butyl-1-(2-fluoro-benzyl)-2,6-dioxo-2,3,6,7-tetrahydro-1H-purin-8-ylmethyl]-pyridin-3-yl}-amide.

Another preferred compound of formula 1A is where $R^2$ is lower alkylsusbstituted by cyclobutyl, $R^3$ is

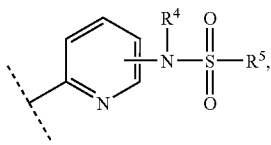

$R^4$ is H and $R^5$ is a 5-membered aromatic heterocyclic ring with one or two heteroatoms wherein a first heteroatom is N and a second heteroatom is selected from the group consisting of N and S, the 5-membered heterocyclic ring being unsubstituted or substituted by at least one substituent selected from the group consisting of lower alkyl, halogen, carboxy lower alkyl, amino, alkyl amino and acetamido. Representative of this preferred compound is 5-chloro-1,3-dimethyl-1H-pyrazole-4-sulfonic acid {6-[3-cyclobutylmethyl-1-(2-fluoro-benzyl)-2,6-dioxo-2,3,6,7-tetrahydro-1H-purin-8-ylmethyl]-pyridin-3-yl}-amide.

Another preferred compound of formula 1 has the formula

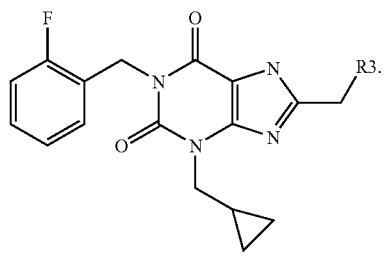

A preferred compound of formula IB is wherein $R^3$ is

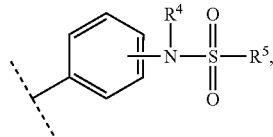

$R^4$ is H and $R^5$ is a 5-membered heteroaromatic ring having two heteroatoms wherein a first heteroatom is N, and a second heteroatom is independently selected from the group consisting of N, O and S, the 5-membered heteroaromatic ring being unsubstituted or substituted by at least one substituent selected from the group consisting of lower alkyl, halogen, carboxy lower alkyl, amino, alkyl amino and acetamido.

A further preferred compound of formula IB is where the 5-membered heteroaromatic ring with two heteroatoms has two lower alkyl substituents. Exemplary of this preferred compound is a compound selected from the group consisting of 1,2-Dimethyl-1H-imidazole-4-sulfonic acid {4-[3-cyclopropylmethyl-1-(2-fluoro-benzyl)-2,6-dioxo-2,3,6,7-tetrahydro-1H-purin-8-ylmethyl]-phenyl}-amide;

3,5-dimethyl-isoxazole-4-sulfonic acid {4-[3-cyclopropylmethyl-1-(2-fluoro-benzyl)-2,6-dioxo-2,3,6,7-tetrahydro-1H-purin-8-ylmethyl]-phenyl}-amide; and 1,3-dimethyl-1H-pyrazole-4-sulfonic acid {4-[3-cyclopropylmethyl-1-(2-fluoro-benzyl)-2,6-dioxo-2,3,6,7-tetrahydro-1H-purin-8-ylmethyl]-phenyl}-amide.

An additional preferred compound of formula IB is where the 5-membered heteroaromatic ring with two heteroatoms has one lower alkyl substituent. Representative of this preferred compound is a compound selected from the group consisting of 1-methyl-1H-pyrazole-4-sulfonic acid {4-[3-cyclopropylmethyl-1-(2-fluoro-benzyl)-2,6-dioxo-2,3,6,7-tetrahydro-1H-purin-8-ylmethyl]-phenyl}-amide, and 1-methyl-1H-imidazole-4-sulfonic acid {4-[3-cyclopropylmethyl-1-(2-fluoro-benzyl)-2,6-dioxo-2,3,6,7-tetrahydro-1H-purin-8-ylmethyl]-phenyl}-amide.

A further preferred compound of formula IB is where the 5-membered heteroaromatic ring with two heteroatoms has one lower alkyl substituent and one amino substituent. Exemplary of this preferred compound is the compound 2-amino-4-methyl-thiazole-5-sulfonic acid {4-[3-cyclopropylmethyl-1-(2-fluoro-benzyl)-2,6-dioxo-2,3,6,7-tetrahydro-1H-purin-8-ylmethyl]-phenyl}-amide trifluoro-acetic acid salt.

A further preferred compound of formula IB is where the 5-membered heteroaromatic ring with two heteroatoms has one lower alkyl substituent and one acetamido substituent. Exemplary of this preferred compound is N-(5-{4-[3-cyclopropylmethyl-1-(2-fluoro-benzyl)-2,6-dioxo-2,3,6,7-tetrahydro-1H-purin-8-ylmethyl]-phenylsulfamoyl}-4-methyl-thiazol-2-yl)-acetamide.

Another preferred compound of formula IB is where the 5-membered heteroaromatic ring with two heteroatoms has one lower alkyl substituent and one halogen substituent. Exemplary of this preferred compound is 5-Chloro-1,3-dimethyl-1H-pyrazole-4-sulfonic acid {4-[3-cyclopropylmethyl-1-(2-fluoro-benzyl)-2,6-dioxo-2,3,6,7-tetrahydro-1H-purin-8-ylmethyl]-phenyl}-amide.

Another preferred compound of formula IB is where the 5-membered heteroaromatic ring with two heteroatoms has three substituents selected from the group lower alkyl, halogen, carboxy lower alkyl, amino, alkyl amino and acetamido. Exemplary of this preferred compound is 5-chloro-1,3-dimethyl-1H-pyrazole-4-sulfonic acid {3-[3-cyclopropylmethyl-1-(2-fluoro-benzyl)-2,6-dioxo-2,3,6,7-tetrahydro-1H-purin-8-ylmethyl]-phenyl}-amide.

Another preferred compound of formula IB is where $R^3$ is

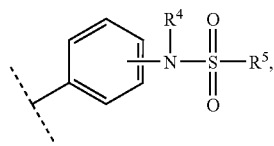

$R^4$ is H and $R^5$ is phenyl substituted by at least one substituent selected from the group consisting of lower alkyl, lower alkyl substituted by halogen, halogen, lower alkoxy, lower alkoxy substituted by halogen, nitro and acetamido.

A further preferred compound of formula IB is where $R^4$ is H and $R^5$ is phenyl substituted by one halogen. Exemplary of this preferred compound is N-{4-[3-cyclopropylmethyl-1-(2-fluoro-benzyl)-2,6-dioxo-2,3,6,7-tetrahydro-1H-purin-8-ylmethyl]-phenyl}-3-fluoro-benzenesulfonamide.

A further preferred compound of formula IB is where $R^4$ is H and $R^5$ is phenyl substituted by one alkoxy. Exemplary of this preferred compound is N-{4-[3-cyclopropylmethyl-1-(2-fluoro-benzyl)-2,6-dioxo-2,3,6,7-tetrahydro-1H-purin-8-ylmethyl]-phenyl}-3-methoxy-benzenesulfonamide.

A further preferred compound of formula IB is where $R^4$ is H and $R^5$ is phenyl substituted by one acetamido. Exemplary of this preferred compound is N-(4-{4-[3-cyclopropylmethyl-1-(2-fluoro-benzyl)-2,6-dioxo-2,3,6,7-tetrahydro-1H-purin-8-ylmethyl]-phenylsulfamoyl}-phenyl)-acetamide.

Another preferred compound of formula IB is where $R^4$ is H and $R^5$ is a 6-membered heteroaromatic ring having one N, the 6-membered heteroaromatic ring being unsubstituted or substituted by at least one substituent selected from the group consisting of lower alkyl, halogen, carboxy lower alkyl, amino, alkyl amino and acetamido.

A preferred compound of formula IB is where $R^4$ is H and $R^5$ is an unsubstituted 6-membered heteroaromatic ring having one N. Exemplary of this preferred compound is pyridine-3-sulfonic acid {4-[3-cyclopropylmethyl-1-(2-fluoro-benzyl)-2,6-dioxo-2,3,6,7-tetrahydro-1H-purin-8-ylmethyl]-phenyl}-amide trifluoro-acetic acid salt.

Another preferred compound of IB is where $R^4$ is H and $R^5$ is a 6-membered heteroaromatic ring having one N is substituted by two halogen substituents. Exemplary of this preferred compound is 5-bromo-6-chloro-pyridine-3-sulfonic acid {4-[3-cyclopropylmethyl-1-(2-fluoro-benzyl)-2,6-dioxo-2,3,6,7-tetrahydro-1H-purin-8-ylmethyl]-phenyl}-amide.

Another preferred compound of formula IB is where $R^3$ is

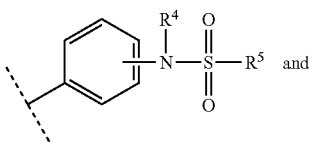 and $R^4$ is H is wherein $R^5$ is lower alkyl. Exemplary of this preferred compound is N-{4-[3-cyclopropylmethyl-1-(2-fluoro-benzyl)-2,6-dioxo-2,3,6,7-tetrahydro-1H-purin-8-ylmethyl]-phenyl}-methanesulfonamide.

Another preferred compound of formula IB is where $R^3$ is

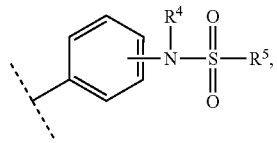

$R^4$ is H, and where $R^5$ is amino lower alkyl. Exemplary of this preferred compound is N-{4-[3-cyclopropylmethyl-1-(2-fluoro-benzyl)-2,6-dioxo-2,3,6,7-tetrahydro-1H-purin-8-ylmethyl]-phenyl}-N,N-dimethylsulfamide.

Another preferred compound of formula IB is where $R^3$ is

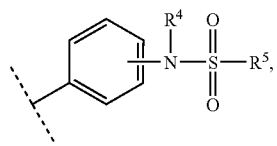

$R^4$ is H, and $R^5$ is

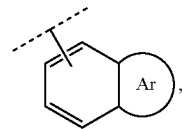

wherein Ar is selected from the group consisting of a 5-membered heteroaromatic ring fused to the 6-membered ring, having one, two, or three heteroatoms, and wherein a first heteroatom is N, a second heteroatom is N and a third heteroatom is selected from the group consisting of O and S, the 5-membered heteroaromatic ring being unsubstituted or substituted by at least one substituent selected from the group consisting of lower alkyl, halogen, carboxy lower alkyl, amino, alkyl amino and acetamido. Exemplary of this preferred compound is quinoline-8-sulfonic acid {4-[3-cyclopropylmethyl-1-(2-fluoro-benzyl)-2,6-dioxo-2,3,6,7-tetrahydro-1H-purin-8-ylmethyl]-phenyl}-amide.

Another preferred compound of formula 1B is where $R^3$ is

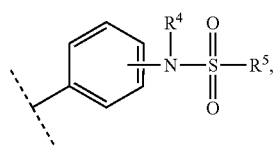

$R^4$ is lower alkyl and $R^5$ is a 5-membered heteroaromatic ring having two heteroatoms wherein a first heteroatom is N and a second heteroatom is independently selected from the group consisting of N, O and S, the 5-membered heteroaromatic ring being unsubstituted or substituted by at least one substituent selected from the group consisting of lower alkyl, halogen, carboxy lower alkyl, amino, alkyl amino and acetamido. Exemplary of this preferred compound is a compound selected from the group consisting of 1,3-dimethyl-1H-pyrazole-4-sulfonic acid {4-[3-cyclopropylmethyl-1-(2-fluoro-benzyl)-2,6-dioxo-2,3,6,7-tetrahydro-1H-purin-8-ylmethyl]-phenyl}-methyl-amide; and 5-chloro-1,3-dimethyl-1H-pyrazole-4-sulfonic acid {4-[3-cyclopropylmethyl-1-(2-fluoro-benzyl)-2,6-dioxo-2,3,6,7-tetrahydro-1H-purin-8-ylmethyl]-phenyl}-methyl-amide.

The prodrugs of the compounds of this invention are preferred embodiments of this invention. As defined above, a prodrug is a compound that may be converted, under physiological conditions or by solvolysis, to a pharmaceutically active compound. Prodders are generally known in the art. See, for example, Design of Prodrugs, Bundgaard, Hans, ed., Neth (1985), 360 pp., Elsevier, Amsterdam, Neth. In accordance therefore, the compounds of this invention further includes its prodrug form.

Purification of GST-PEPCK

*E. coli* cells expressing GST-PEPCK were suspended in 5 volumes of lysis buffer (50 mM Tris-hydroxymethyl aminomethyl (TRIS), 150 mM sodium chloride (NaCl), 10 mM ethylene-diametetraacetic acid (EDTA), 5 mM dithiothreitol (DTT), 1% Nonidet P-40, pH 7.4) in the presence of protease inhibitors, incubated with lysozyme at 200 micrograms/ml for 30 min. at room temperature, and sonicated 4×30 seconds at 4 degrees C. After centrifugation at 12,000×g for 20 min. to remove insoluble material, the supernatant was loaded onto glutathione Sepharose (Pharmacia), washed with lysis buffer followed by washing with lysis buffer in the absence of NP-40. GST-PEPCK was eluted with the same buffer containing 20 mM glutathione. The eluted protein was concentrated and dialyzed against 25 mM Hepes(N-[2-hydroxyethyl]piperazine-N'[2-ethanesulfonic acid), 150 mM NaCl, 2.5 mM EDTA, 5 mM DTT, 30% glycerol, pH 7.4, and stored at −20° C.

PEPCK Enzyme Assay

The inhibitory effect of the compounds of the present invention on PEPCK enzymatic activity was determined using recombinant human cytosolic PEPCK, expressed and purified from *E.coli* as a GST-fusion. Guanosine triphosphate (GTP) and manganese dependent PEPCK enzyme activity catalyzed the decarboxylation of oxalacetate leading to the formation of guanosine diphosphate (GDP) and phosphoenol pyruvate (PEP). This reaction is coupled to pyruvate kinase and lactate dehydrogenase catalyzed reactions and the overall reaction rate determined by measuring the change in absorbance at 340 nM (Chang, H. C. and Lane M. D., J. Biol. Chem. 241:2413–2420, 1966). The following modifications were made to the protocol: 2.5 μg of recombinant, human cytosolic glutathione-S-transferase (GST)-PEPCK was added to a reaction mixture at room temperature which contained 0.3 mM GTP, 0.3 mM oxaloacetate (OAA), 3 mM magnesium chloride ($MgCl_2$), 0.075 mM manganese chloride ($MnCl_2$), 30 mM potassium phosphates ($KPO_4$), pH 7.6, 1 mM dithiothreitol (DTT), 0.2 mM adenosine diphosphate (ADP), 1 mM nicotinamide adenine dinucleotide, reduced form (NADH), 0.9 Units/ml each of pyruvate kinase and lactate dehydrogenase and 1 mg/ml bovine serum albumin (BSA). Test compounds were added such that final concentration of DMSO was 10%. Reactions were run for twenty minutes.

$K_m$ values for GTP and OAA were determined according to Michelis-Menton conditions as described in Comish-Bowden (Fundamentals of Enzyme Kinetics, 1995) in essentially the coupled assay conditions described above. To determine the concentrations at which test compounds inhibited the enzyme 50% ($IC_{50}$), reaction mixtures containing 3 fold and 10 fold the calculated $K_m$ values for GTP and OAA, respectively, were employed. Test compounds were added to reactions over a range of concentrations and $IC_{50}$'s were calculated from plots of inhibitor concentration versus enzyme rate. This method of determination of $IC_{50}$ values is equally applicable to calculations based on PEPCK cellular assay.

General Description of Synthetic Pathways

PEPCK Sulfonamide Derivatives—

Compounds with the general formula provided herein may be prepared by application of the appropriate transformations as outlined in schemes 1 through 7 inclusive. The typical strategy employed was to prepare an aniline bearing derivative of a 1,3,8-trisubstituted xanthine which were then reacted with a sulfonyl chloride to form the desired sulfonamide derivative. If the resulting sulfonamide derivatives also contain reactive functional groups, further derivatization was possible by application of standard chemical techniques. In cases where it was not possible to assemble the desired sulfonamide derivatives by reaction of an 1,3,8-trisubstituted xanthine containing an appropriately substituted aniline with a sulfonyl chloride, the desired derivatives were prepared by pre-assembling the sulfonamide component and incorporating this component into the synthetic scheme in place of the protected aniline or aniline precursor.

One method used for preparing some of the 1,3,8-trisubstituted xanthine derivatives bearing an aniline substituent which were subsequently used for preparation of sulfonamide derivatives is shown in scheme 1. Starting from commercially available 6-amino-1H-pyrimidine-2,4-dione 2, alkylation of the nitrogen at position 3 to give compounds of general structure 3 was achieved using the procedure of Müller as described in Tetrahedron Lett. 1991, 32(45), 6539. Compounds of general formula 2 were converted to their per-silylated derivatives by heating in commercially available 1,1,1,3,3,3-hexamethyldisilazane (HMDS) in the presence of a catalytic amount of commercially available ammonium sulfate. The intermediate per-silylated derivatives of compounds of general formula 2 were isolated by concentration under high vacuum and reacted immediately with the desired commercially available alkylating agent and a catalytic amount of commercially available elemental iodine at reflux. The reaction was judged complete when a good level of conversion to the 3-substituted derivatives of general formula 3 had been achieved (as judged by thin layer chromatography) and prior to the formation of significant amounts of undesired by-products.

Scheme 1

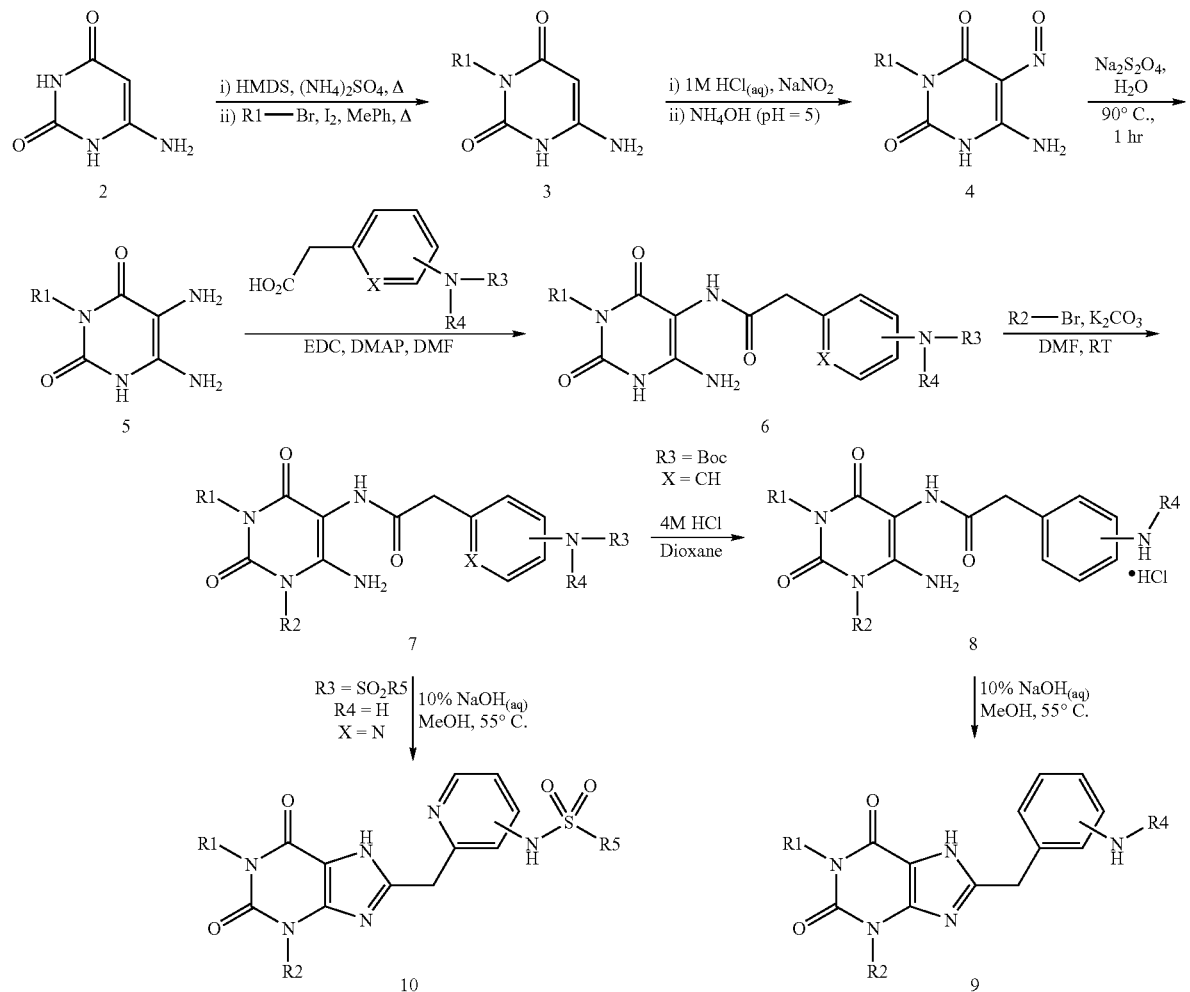

Nitrosylation of 3-substituted-6-amino-1H-pyrimidine-2,4-diones of general formula 3 was performed by use of a procedure similar to that of Müller et al. as described in J. Med. Chem. 1993, 36, 3341. Compounds of general formula 3 were heated in aqueous 1 Molar hydrochloric acid and treated with commercially available sodium nitrite to form the orange to red colored 6-amino-5-nitroso-1H-pyrimidine-2,4-diones of general formula 4 which were isolated as solids after treating the reaction mixture with 1 Molar aqueous ammonium hydroxide until the reaction mixture was at pH=5. The crude products were precipitated, isolated by filtration and used without further purification. The 6-amino-5-nitroso-1H-pyrimidine-2,4-diones of general formula 4 were reduced to the 5,6-diamino-1H-pyrimidine-2,4-diones of general formula 5 by use of a procedure similar to that of Müller et al. as described in J. Med. Chem. 1993, 36, 3341.

Commercially available sodium dihydrosulfite was added portionwise to a suspension of the nitroso derivatives of general formula 4 in water at approximately 90° C. The reaction was judged complete when the color of the nitroso compounds had been fully discharged. The 5,6-diamino-1H-pyrimidine-2,4-diones of general formula 5 were relatively unstable and were used immediately in the next step in the synthetic pathway without additional purification.

Acylation of the 5,6-diamino-1H-pyrimidine-2,4-diones of general formula 5 was performed according to the procedure of Jacobson et al. as described in J. Med. Chem. 1993, 36(10), 1333. Treatment of a mixture of a diamine of general formula 5 with an appropriately substituted aryl or hetero-aryl acetic acid derivative and commercially available 1-(3-dimethylaminopropyl)-3-ethylcarbodiimide hydrochloride (EDC) resulted in amide formation selectively at the 5-position of the 1H-pyrimidine-2,4-dione ring to give amide derivatives of general formula 6. The aryl and hetero-aryl acetic acids used in this step were either commercially available or were prepared by the routes outlined in schemes 6 and 7.

5-Acetamido-6-amino uracil derivatives of general formula 6 were selectively alkylated at the 1 position of the 1H-pyrimidine-2,4-dione to give compounds of general structure 7 by use of the appropriate alkylating agent with anhydrous potassium carbonate in DMF by analogy with the procedure of Müller et al. as described in Synthesis 1995, 1295. In the case where R3 in compounds of general formula 7 was a Boc-protecting group and the ring atom X was carbon with an attached hydrogen, the Boc-protecting group was removed by treatment with commercially available 4 Molar hydrogen chloride in p-dioxane solution. The crude hydrochloride salts of general formula 8 precipitated from the reaction mixture and were isolated by filtration and used without further purification. 5-Acetamido-6-amino derivatives of general formula 8 were cyclized to form the 1,3,8-trisubstituted xanthines of general formula 9 by heating to approximately 50° C. in methanol containing 10% aqueous sodium hydroxide solution in a manner similar to that described by Müller et al. in Synthesis 1995, 1295. The reactions were monitored by TLC until all of the starting 5-acetamido-6-amino derivative of general formula 8 had been consumed. The aniline bearing 1,3,8-trisubstituted xanthine derivative of general formula 9 were isolated from the reaction mixture with sufficient purity for subsequent chemical modification by extraction and concentration.

In the case where in compounds of general formula 7, $R^3$ was a sulfonyl group and the ring atom X was nitrogen, cyclization to compounds of general formula 10 was also be achieved by heating to approximately 50° C. in methanol containing 10% aqueous sodium hydroxide solution as described previously.

Another route which was used for the preparation of 1,3,8-trisubstituted xanthine derivatives which either bear an aniline substituent suitable for subsequent derivatization into a sulfonamide group or a pre-formed sulfonamide group is shown in scheme 2. Commercially available ethyl cyanoacetate 12 and an appropriately substituted commercially available mono-substituted urea 11 were condensed in the presence of sodium ethoxide in refluxing ethanol according to the procedure of Papesch and Schroeder as described in J. Org. Chem. 1951, 16, 1879 to give 1-substituted-6-amino-1H-pyrimidine-2,4-diones of general formula 13.

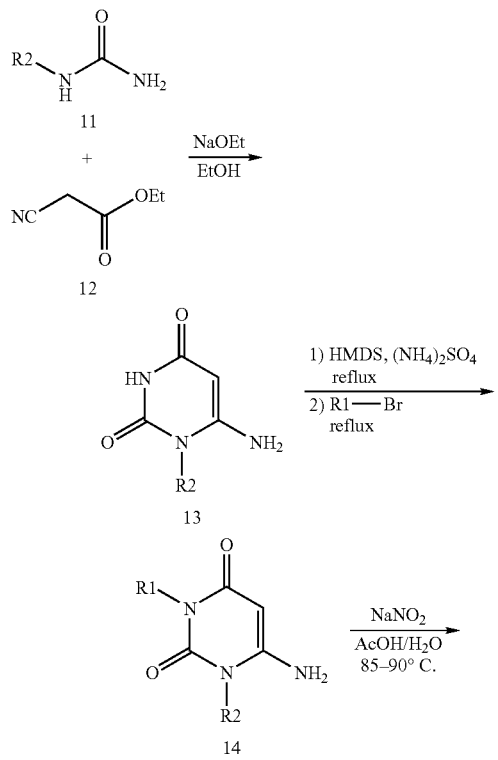

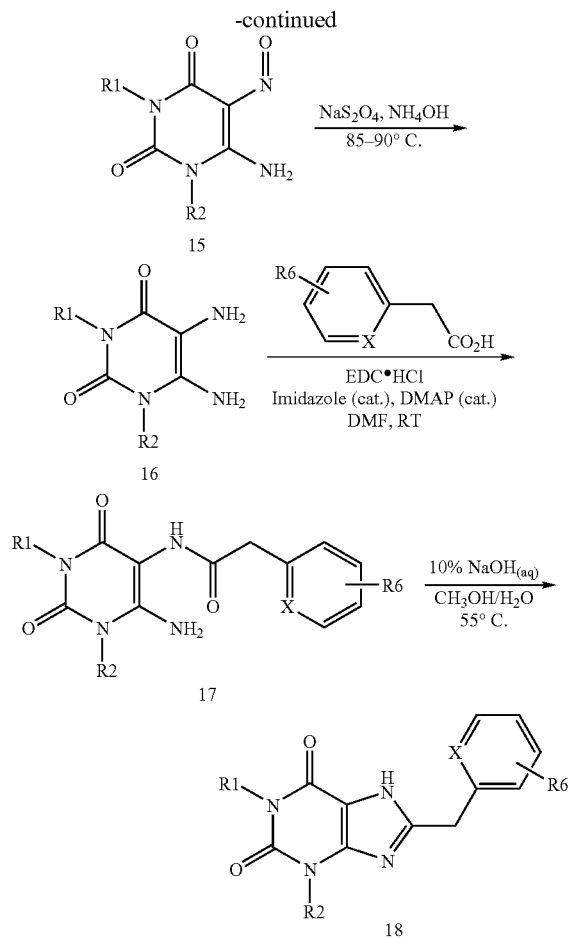

1-Substituted-6-amino-1H-pyrimidine-2,4-diones of general formula 13 were then alkylated at the 3-position by application of the method of Müller et al. as described in J. Med. Chem. 1993, 36, 3341. This method is similar to that described above for scheme 1 wherein compounds of general formula 2 are converted into compounds of general formula 3 and involved the mono-alkylation of the per-silylated derivatives of compounds of general formula 13 with an appropriate alkylating agent to give the 1,3-dialkylated compounds of general formula 14.

Nitrosylation of 1,3-disubstituted-6-amino-1H-pyrimidine-2,4-diones of general formula 14 was performed according to the procedure of Müller et al. as described in J. Med. Chem. 1993, 36, 3341. Compounds of general formula 14 were heated in aqueous acetic acid and treated with commercially available sodium nitrite to form the orange to red colored 6-amino-5-nitroso-1H-pyrimidine-2,4-diones of general formula 15 which were isolated by filtration as solids after cooling to 0° C.

The 6-amino-5-nitroso-1H-pyrimidine-2,4-diones 15 were reduced to the 5,6-diamino-1H-pyrimidine-2,4-diones of general formula 16 with commercially available sodium dihydrosulfite in 10% aqueous ammonium hydroxide at approximately 90° C. This method is based on the method described by Müller et al. in J. Med. Chem. 1993, 36, 3341. The reaction was judged complete when the color of the nitroso compounds had been fully discharged. The 5,6-diamino-1H-pyrimidine-2,4-diones of general formula 16 were relatively unstable and were used immediately in the next step in the synthetic pathway without additional purification.

Acylation of the 5,6-diamino-1H-pyrimidine-2,4-diones of general formula 16 was performed according to the procedure of Jacobson et al. as described in J. Med. Chem. 1993, 36(10), 1333. Treatment of a mixture of a diamine of general formula 16 and the appropriately substituted phenyl or heterocyclic acetic acid derivative with commercially available 1-(3-dimethylaminopropyl)-3-ethylcarbodiimide hydrochloride (EDC) resulted in amide formation selectively at the 5-position of the 1H-pyrimidine-2,4-dione ring to give compounds of general formula 17. Amide derivatives of general formula 17 were stable products which were typically not purified following isolation of the crude reaction product. In the case where $R^6$=—$NR^3R^4$, compounds of general formula 17 were identical with compounds of general formula 7 and could be derivatized in a similar fashion (as shown in scheme 1). In the case where $R^6$=—N(Boc)$R^4$, the protected aniline was carried through the xanthine cyclization step to form compounds of general formula 18 and removed subsequently (see scheme 4). $R^6$ could also be a sulfonamide group which was attached to the aryl or hetero-aryl ring via nitrogen. In addition, $R^6$ could be a sulfonamide group which was attached to the phenyl ring (X=CH) through sulfur. The requisite sulfonamide substituted aryl acetic acids were prepared as outlined in scheme 6. 5-Acetamido-6-amino derivatives of general formula 17 were cyclized to form the 1,3,8-trisubstituted xanthines of general formula 18 by heating to approximately 50° C. in methanol containing 10% aqueous sodium hydroxide solution in a manner similar to that described by Müller et al. in Synthesis 1995, 1295. The reactions were monitored by TLC until all of the starting 5-acetamido-6-amino derivatives of general formula 17 had been consumed. Pure products were obtained using standard chemical purification techniques such as chromatography, crystallization or trituration.

A third route which was used to prepare some of the 1,3,8-trisubstituted xanthine derivatives claimed in this patent application is shown in scheme 3. Starting from commercially available 6-chloro-1H-pyrimidine-2,4-dione 19, selective alkylation of the nitrogen at the 1-position of the pyrimidine ring was achieved with the appropriate alkylating agent to give compounds of general formula 20 by use of a method similar to that of Ishikawa et al. as described in Heterocycles 1990, 31(9), 1641. Using the same reaction conditions and a second alkylating agent (or a second equivalent of the first alkylating agent) a substituent was then introduced at the 3-position of the pyrimidine ring to furnish compounds of general formula 21.

Scheme 3

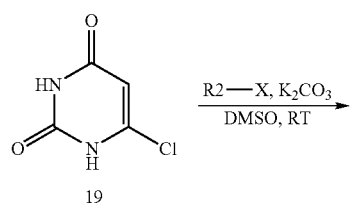

19

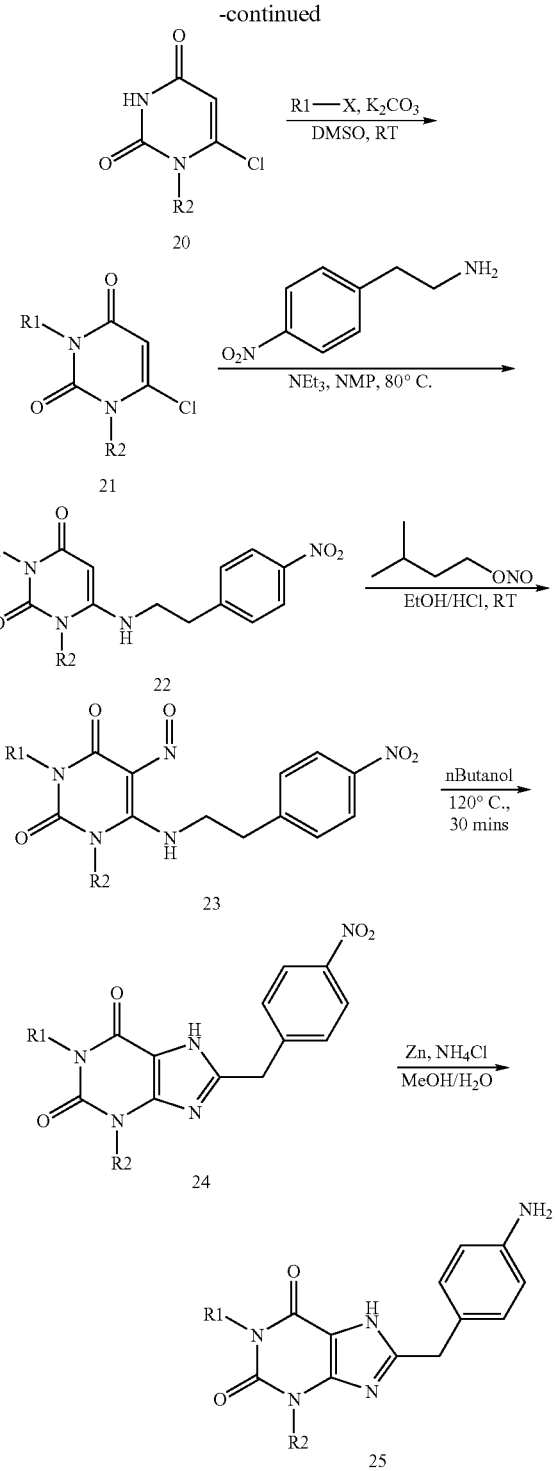

Displacement of chloride from compounds of general formula 21 with 2-(4-nitro-phenyl)-ethylamine hydrochloride salt and triethylamine in N-methylpyrrolidinone (NMP) at 75° C. results in formation of compounds of general formula 22. These procedures were similar in nature to those previously described by Müller et al. in J. Med. Chem. 1993, 36, 3341 and by Shamin et al. in J. Med. Chem. 1989, 32(6), 1231 wherein similar transformations are performed on N1-unsubstituted uracils.

Treatment of compounds of general formula 22 with commercially available isoamyl nitrite resulted in introduction of a nitroso group at the 5-position of the uracil ring as in compounds of general formula 23.

Cyclization of the 5-nitroso-6-amino substituted uracil derivatives of general formula 23 to the trisubstituted xanthines of general formula 24 was effected in refluxing nbutanol as shown in scheme 3. Compounds of general formula 24 were then reduced to the corresponding anilines of general formula 25 with zinc powder and ammonium chloride in aqueous methanol.

In the case where the final product from scheme 2, compounds of general formula 18, was a Boc-protected aniline, the protecting group had to be removed prior to further functionalization of the aniline nitrogen. As shown in scheme 4, when the protecting group was Boc as in compounds of general formula 26, the aniline was liberated by treatment with commercially available 4M hydrogen chloride in p-dioxane solution to give anilines of general formula 27 (which were isolated as the hydrochloride salts). Anilines of general formula 27 were equivalent with anilines of general formula 9 and 25 prepared as shown in schemes 1 and 3 respectively. Reaction of anilines prepared by either of these 3 routes with a sulfonyl chloride resulted in formation of sulfonamide derivatives of general formula 28. In the case where $R^5$ contained chemically reactive groups further modification of this residue was possible by application of appropriate standard chemical techniques.

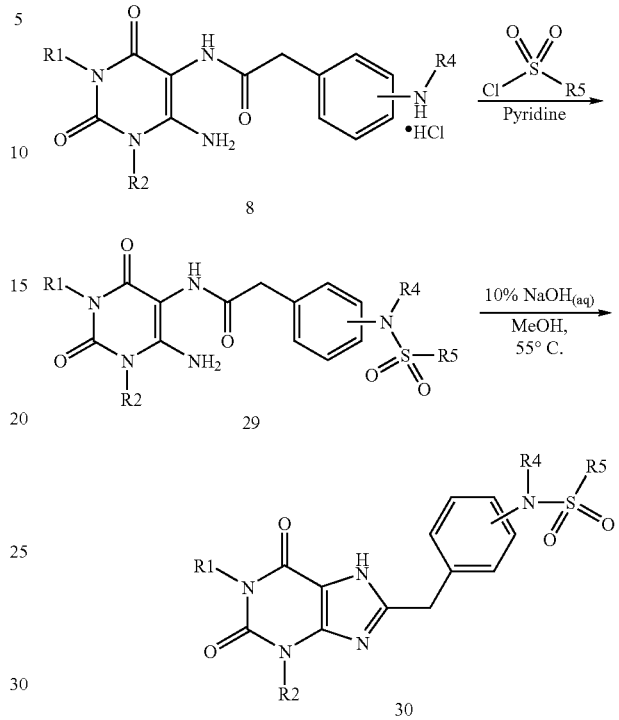

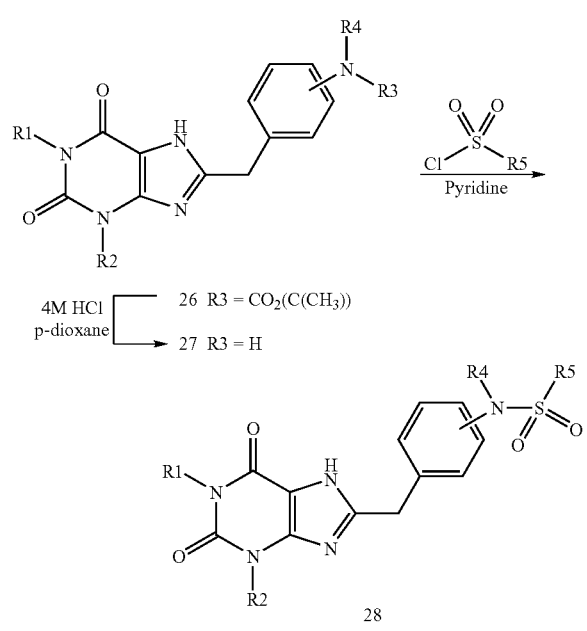

It was also possible to form a sulfonamide with anilines of general formula 8 prior to cyclization to the xanthine as shown in scheme 5. The sulfonamide containing 5-acetamido-6-amino uracil derivatives of general formula 29 were cyclized to the sulfonamide containing xanthine derivatives of general formula 30 using the standard conditions described previously.

In scheme 2, when the aryl acetic acid component used to acylate diamines of general formula 16 contained a sulfonamide group which was attached to the aryl ring through sulfur, the aryl acetic acid components were prepared as shown in scheme 6. (4-Chlorosulfonyl-phenyl)-acetic acid ethyl ester (compound 32) was prepared from commercially available phenylacetic acid ethyl ester with commercially available chlorosulfonic acid according to the procedure of Kawashima et al. as described in Chem. Pharm. Bull. 1995, 43(7), 1132. Sulfonyl chlorides of general formula 32 were condensed with amine derivatives to give sulfonamides of general formula 33 in pyridine either between 0° C. and room temperature or by warming to 50° C. The ethyl ester was removed by heating with potassium hydroxide in ethanol followed by treatment with aqueous hydrochloric acid to form carboxylic acids of general formula 34.

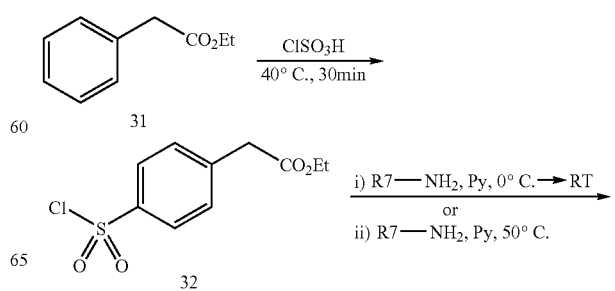

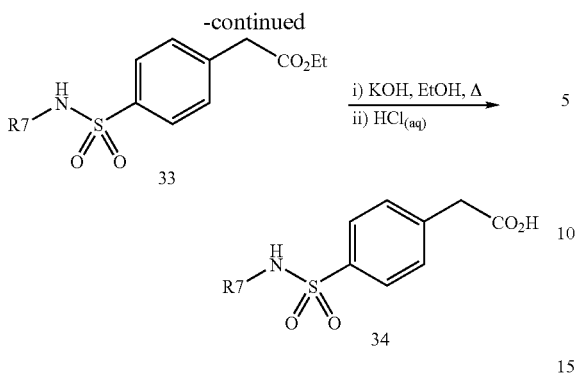

In schemes 1 and 2, when the acetic acid component used to acylate diamines of general formula 5 and 16 respectively was attached to a sulfonamide substituted pyridine ring, the heteroaryl acetic acid component was prepared by application of the procedures outlined in scheme 7. The potassium salt of dibenzyl malonate was used to displace chloride from commercially available 2-chloro-5-nitro-pyridine in dimethylsulfoxide solution at 95° C. Reduction of the nitro group in compounds of general formula 36 was achieved using zinc powder and ammonium chloride in aqueous methanol to give the 5-amino-pyridines of general formula 37. 5-Amino-pyridines of general formula 37 were then condensed with sulfonyl chloride derivatives under standard conditions to give sulfonamides of general formula 38. When subjected to hydrogenolysis using 1 atmosphere pressure of hydrogen and 10% palladium on carbon catalyst the dibenzyl malonates of general formula 38 are converted into sulfonamide substituted 2-pyridylacetic acid derivatives of general formula 39.

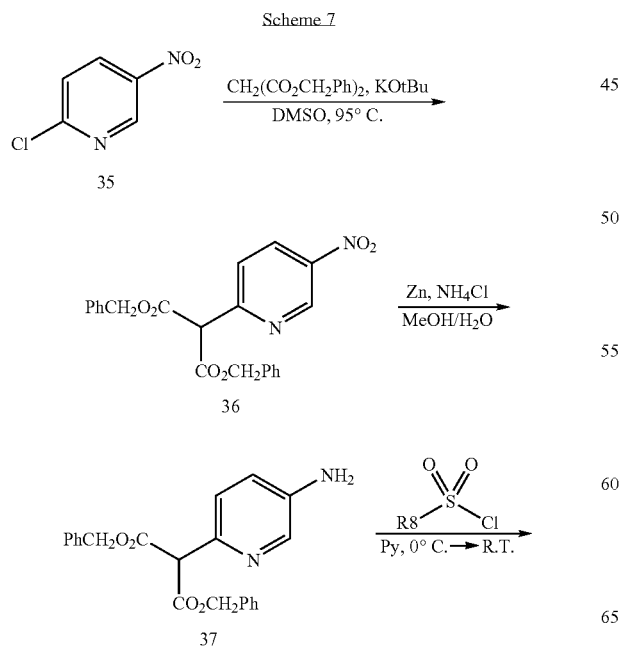

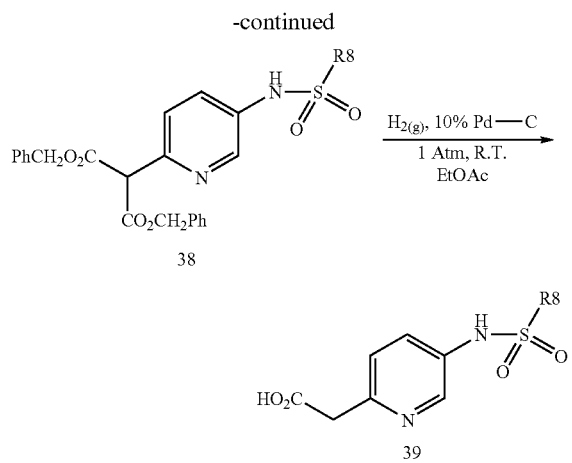

EXPERIMENTAL DETAILS-EXAMPLES

Example 1

5-Chloro-1,3-dimethyl-1H-pyrazole-4-sulfonic acid {4-[3-cyclopropylmethyl-1-(2-fluoro-benzyl)-2,6-dioxo-2,3,6,7-tetrahydro-1H-purin-8-ylmethyl]-phenyl}-amide

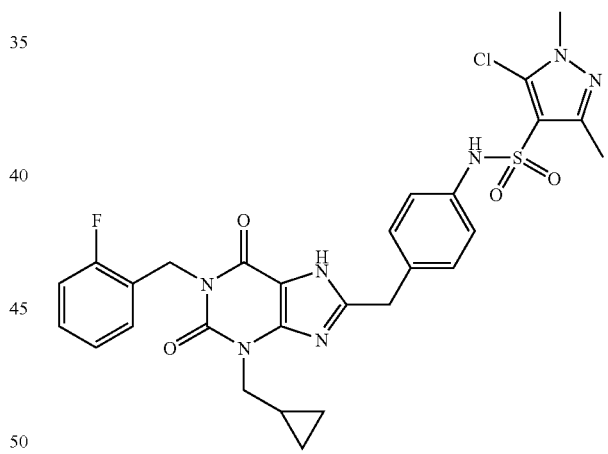

This compound was prepared by the routes outlined in schemes 1 and 4.

Step 1: Preparation of 6-amino-3-(2-fluoro-benzyl)-1H-pyrimidine-2,4-dione.

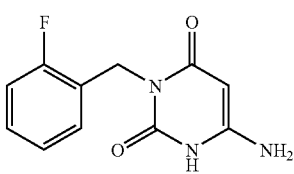

A mixture of 4-amino-2,6-dihydroxypyrimidine (10 g, 79.0 mmol), ammonium sulfate (570 mg, 3.95 mmol), and hexamethyldisilizane (60 mL, 292.3 mmol) was heated to reflux for 3.25 h. At this time, the reaction was cooled to 25° C. and concentrated in vacuo to afford a white solid. The solid was mixed with toluene (12 mL) under argon and then treated with 2-fluorobenzyl bromide (12.6 mL, 102.7 mmol) and iodine (470 mg, 1.58 mmol). This mixture was heated to reflux for 2 h. A brown suspension was formed. The reaction was stirred at 25° C. overnight. At this time, the reaction mixture was cooled to 0° C. and then treated with a solution of sodium thiosulfate (2.47 g in 40 mL of water). A very thick suspension formed which needed to be stirred by hand. The solids were broken up with a spatula. The mixture was then treated with a saturated aqueous sodium bicarbonate solution (300 mL) and was stirred at 0° C. for 30 min. The resulting solid was collected by filtration and washed well with water, toluene, and then ether. The solid was then dried in vacuo to afford 6-amino-3-(2-fluoro-benzyl)-1H-pyrimidine-2,4-dione (20.80 g, quant.) as a tan solid; LRMS for $C_{11}H_{10}FN_3O_2S(M+H)^+$ at m/z=236.

Step 2: Preparation of 6-amino-3-(2-fluoro-benzyl)-5-nitroso-1H-pyrimidine-2,4-dione.

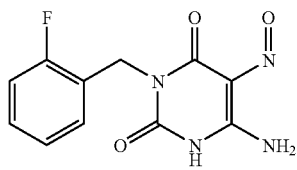

A mixture of 6-amino-3-(2-fluoro-benzyl)-1H-pyrimidine-2,4-dione (2.4 g, 10.6 mmol) in a 1.0N aqueous hydrochloric acid solution at 25° C. was treated with a solution of sodium nitrite (0.95 g, 13.78 mmol) in water (10 mL). The mixture was stirred at 25° C. for 3 h. At this time, the reaction was brought to pH=5 through treatment with a 1.0N aqueous ammonium hydroxide solution. The resulting solid was collected by filtration and washed with cold water to afford 6-amino-3-(2-fluoro-benzyl)-5-nitroso-1H-pyrimidine-2,4-dione (2.58 g, 92%); LRMS for $C_{11}H_9FN_4O_3$ $(M+H)^+$ at m/z=265.

Step 3: Preparation of 5,6-diamino-3-(2-fluoro-benzyl)-1H-pyrimidine-2,4-dione.

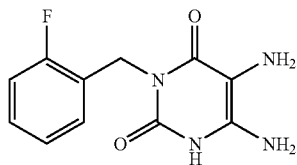

A mixture of 6-amino-3-(2-fluoro-benzyl)-5-nitroso-1H-pyrimidine-2,4-dione in water at 80° C. was treated with sodium hydrosulfite (5.94 g, 34.16 mmol). The reaction was stirred at 80° C. for 30 min. At this time, the reaction mixture was cooled to 0° C. for 10 min. The resulting solids were collected by filtration, rinsed with cold water and cold ether, and dried in vacuo to afford 5,6-diamino-3-(2-fluoro-benzyl)-1H-pyrimidine-2,4-dione (2.34 g, 96%); LRMS for $C_{11}H_{11}FN_4O_2$ $(M+H)^+$ at m/z=251.

Step 4: Preparation of (4-{[6-amino-3-(2-fluoro-benzyl)-2,4-dioxo-1,2,3,4-tetrahydro-pyrimidin-5-ylcarbamoyl]-methyl}-phenyl)-carbamic acid tert-butyl ester.

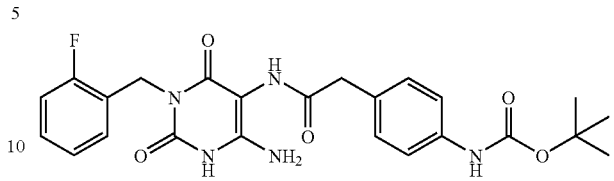

A solution of (4-tert-butoxycarbonylamino-phenyl)-acetic acid in N,N-dimethylformamide under argon at 25° C. was treated with 1-(3-dimethylaminopropyl)-3-ethylcarbodiimide hydrochloride. The reaction was stirred at 25° C. for 5 min. At this time, the reaction was treated with 5,6-diamino-3-(2-fluoro-benzyl)-1H-pyrimidine-2,4-dione and 4-dimethylarninopyridine. The reaction was stirred at 25° C. for 18 h. At this time, the reaction was concentrated in vacuo. The residue was diluted with water (75 mL) and then acidified to pH=5 with a 1.0N aqueous hydrochloric acid solution. The resulting solid was collected by filtration, rinsed well with water and cold ether, and dried in vacuo to afford (4-{[6-amino-3-(2-fluoro-benzyl)-2,4-dioxo-1,2,3,4-tetrahydro-pyrimidin-5-ylcarbamoyl]-methyl}-phenyl)-carbamic acid tert-butyl ester (4.10 g, 91%) as a yellow solid; LRMS for $C_{28}H_{32}FN_5O_5$ $(M+H)^+$ at m/z=538.

Step 5: Preparation of (4-{[6-amino-1-cyclopropylmethyl-3-(2-fluoro-benzyl)-2,4-dioxo-1,2,3,4-tetrahydro-pyrimidin-5-ylcarbamoyl]-methyl}-phenyl)-carbamic acid tert-butyl ester.

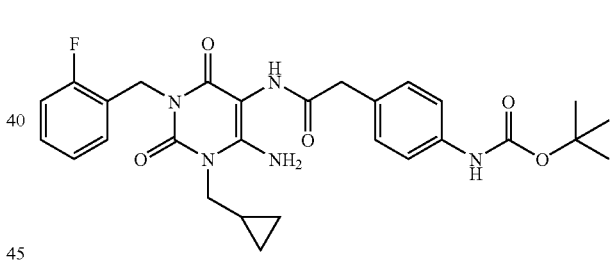

A solution of (4-{[6-amino-3-(2-fluoro-benzyl)-2,4-dioxo-1,2,3,4-tetrahydro-pyrimidin-5-ylcarbamoyl]-methyl}-phenyl)-carbamic acid tert-butyl ester in N,N-dimethylformamide (2.5 g, 5.17 mmol) at 25° C. under argon was treated with potassium carbonate (6.43 g, 46.53 mmol) followed by cyclopropyl methyl bromide (752 mg, 7.76 mmol). The suspension was stirred at 25° C. overnight. At this time, the reaction was concentrated in vacuo. The residue was diluted with a solution of water (100 mL) and a 1.0N aqueous hydrochloric acid solution (31 mL). The resulting suspension was diluted with chloroform and neutralized with a 1.0N aqueous hydrochloric acid solution. The layers were separated. The aqueous layer was extracted with chloroform. The organics layers were washed with a saturated aqueous sodium chloride solution, dried over magnesium sulfate, filtered, and concentrated in vacuo. Flash chromatography (Merck Silica gel 60, 230–400 mesh, 97/3 methylene chloride/methanol) afforded (4-{[6-amino-1-cyclopropylmethyl-3-(2-fluoro-benzyl)-2,4-dioxo-1,2,3,4-tetrahydro-pyrimidin-5-ylcarbamoyl]-methyl}-phenyl)-carbamic acid tert-butyl ester (1.45 g, 52%) as an orange foam; EI-HRMS m/e calculated for $C_{28}H_{32}FN_5O_5$ (M+) 537.2387. found 537.2387.

Step 6: Preparation of N-[6-amino-1-cyclopropylmethyl-3-(2-fluoro-benzyl)-2,4-dioxo-1,2,3,4-tetrahydro-pyrimidin-5-yl]-2-(4-amino-phenyl)-acetamide, hydrochloride salt.

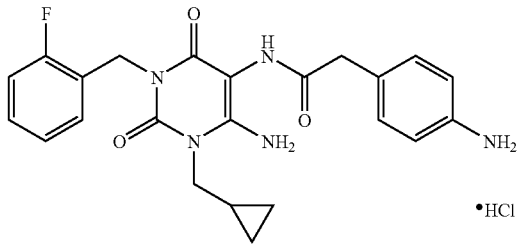

A solution of (4-{[6-amino-1-cyclopropylmethyl-3-(2-fluoro-benzyl)-2,4-dioxo-1,2,3,4-tetrahydro-pyrimidin-5-ylcarbamoyl]-methyl}-phenyl)-carbamic acid tert-butyl ester (2.20 g, 4.10 mmol) in a solution of a 4.0N aqueous hydrochloric acid solution in dioxane (37.0 mL) was stirred at 25° C. for 1 h. A suspension formed during this time. The reaction mixture was cooled to 0° C. The resulting solid was collected by filtration, washed with dioxane and cold diethyl ether, and dried in vacuo to afford N-[6-amino-1-cyclopropylmethyl-3-(2-fluoro-benzyl)-2,4-dioxo-1,2,3,4-tetrahydro-pyrimidin-5-yl]-2-(4-amino-phenyl)-acetamide, hydrochloride salt (1.73 g, 89%); LRMS for $C_{23}H_{23}FN_5O_3$ (M+H)+ at m/z=438.

Step 7: Preparation of 8-(4-amino-benzyl)-3-cyclopropylmethyl-1-(2-fluoro-benzyl)-3,4,5,7-tetrahydro-purine-2,6-dione.

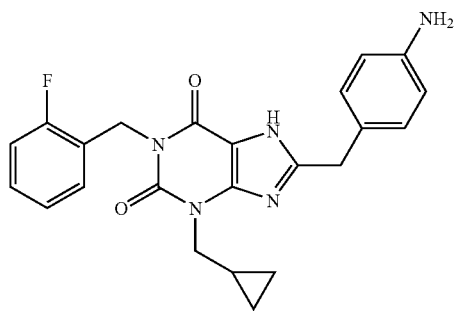

A solution of N-[6-amino-1-cyclopropylmethyl-3-(2-fluoro-benzyl)-2,4-dioxo-1,2,3,4-tetrahydro-pyrimidin-5-yl]-2-(4-amino-phenyl)-acetamide (850 mg, 1.79 mmol) in methanol (20 mL) at 25° C. was treated with a 10% aqueous sodium hydroxide solution (10.7 mL). The reaction mixture was heated to 55° C. for 4.5 h.

At this time, reaction was diluted with chloroform (100 mL) and a saturated aqueous sodium chloride solution (15 mL). The layers were separated. The aqueous layer was extracted with chloroform, neutralized with a 1.0N aqueous hydrochloric acid solution, and then re-extracted with chloroform. The organic layers were combined and washed with a saturated aqueous sodium chloride solution, dried over magnesium sulfate, filtered, and concentrated in vacuo to afford 8-(4-amino-benzyl)-3-cyclopropylmethyl-1-(2-fluoro-benzyl)-3,4,5,7-tetrahydro-purine-2,6-dione (607 mg, 81%) as a pale yellow solid; LRMS for $C_{28}H_{29}FN_7O_5S$ (M+H)+ at m/z=630.

Step 8: Preparation of 5-chloro-1,3-dimethyl-1H-pyrazole-4-sulfonic acid {4-[3-cyclopropylmethyl-1-(2-fluoro-benzyl)-2,6-dioxo-2,3,6,7-tetrahydro-1H-purin-8-ylmethyl]-phenyl}-amide.

A solution of 8-(4-amino-benzyl)-3-cyclopropylmethyl-1-(2-fluoro-benzyl)-3,7-dihydro-purine-2,6-dione (2.0 g, 4.77 mmol) in pyridine (30 mL) under argon at 25° C. was treated with 5-chloro-1,3-dimethyl-pyrazole-4-sulfonyl chloride (1.31 g, 5.72 mmol). The reaction mixture was stirred at 25° C. for 24 h. The reaction mixture was then diluted with methylene chloride (500 mL) and washed with a 1.0N aqueous hydrochloric acid solution (3×100 mL). The combined water layers were extracted with methylene chloride (1×250 mL). The combined organics were washed with a saturated aqueous sodium chloride solution (1×100 mL), dried over magnesium sulfate, filtered, and concentrated in vacuo. The resulting solid was stirred in acetonitrile (25 mL) for 20 min and then placed in the freezer for 1 h. The solids were collected by filtration, washed with cold acetonitrile, and dried in vacuo to afford 5-chloro-1,3-dimethyl-1H-pyrazole-4-sulfonic acid {4-[3-cyclopropylmethyl-1-(2-fluoro-benzyl)-2,6-dioxo-2,3,6,7-tetrahydro-1H-purin-8-ylmethyl]-phenyl}-amide (2.53 g, 87%) as a yellow solid; FAB-HRMS m/e calculated for $C_{28}H_{27}ClFN_7O_4S$ (M+H)+ 612.1596, found 612.1585.

The compounds cited in examples 2 to 6 were obtained in an analogous manner to that described in Example 1.

Example 2

1-Methyl-1H-pyrazole-4-sulfonic acid {4-[3-cyclopropylmethyl-1-(2-fluoro-benzyl)-2,6-dioxo-2,3,6,7-tetrahydro-1H-purin-8-ylmethyl]-phenyl}-amide

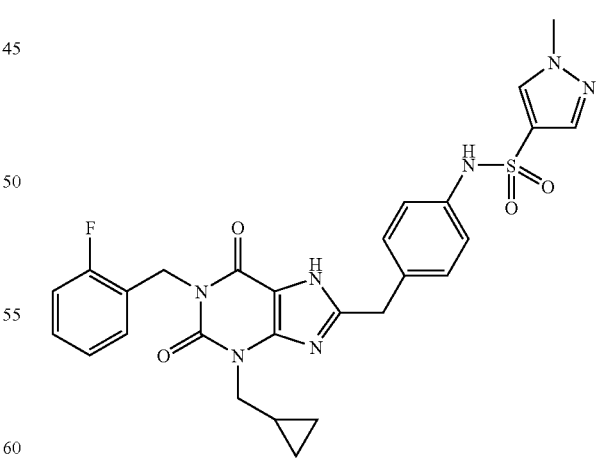

Prepared from 8-(4-amino-benzyl)-3-cyclopropylmethyl-1-(2-fluoro-benzyl)-3,7-dihydro-purine-2,6-dione and 1-methyl-1H-pyrazole-4-sulfonyl chloride. Off-white solid; EI-HRMS m/e calculated for $C_{27}H_{26}FN_7O_4S$ (M+) 563.1751, found 563.1752.

Example 3

N-{4-[3-Cyclopropylmethyl-1-(2-fluoro-benzyl)-2,6-dioxo-2,3,6,7-tetrahydro-1H-purin-8-ylmethyl]-phenyl}-3-methoxy-benzenesulfonamide

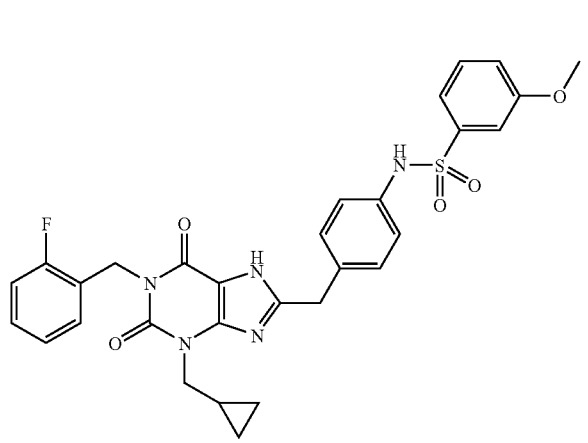

Prepared from 8-(4-amino-benzyl)-3-cyclopropylmethyl-1-(2-fluoro-benzyl)-3,7-dihydro-purine-2,6-dione and 3-methoxy-benzenesulfonyl chloride. White solid; EI-HRMS m/e calculated for $C_{30}H_{28}FN_5O_5S$ (M$^+$) 589.1795, found 589.1801.

Example 4

N-{4-[3-Cyclopropylmethyl-1-(2-fluoro-benzyl)-2,6-dioxo-2,3,6,7-tetrahydro-1H-purin-8-ylmethyl]-phenyl}-3-fluoro-benzenesulfonamide

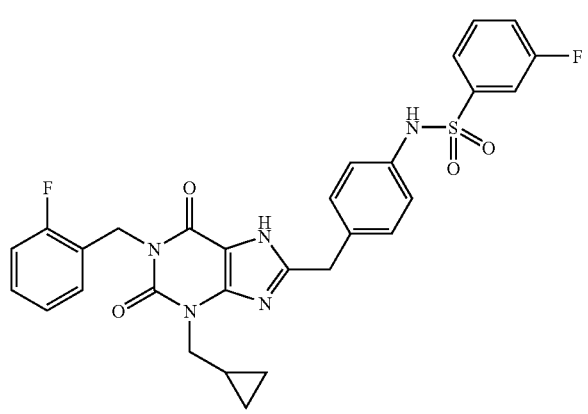

Prepared from 8-(4-amino-benzyl)-3-cyclopropylmethyl-1-(2-fluoro-benzyl)-3,7-dihydro-purine-2,6-dione and 3-fluoro-benzenesulfonyl chloride. Tan solid; EI-HRMS m/e calculated for $C_{29}H_{25}F_2N_5O_4S$ (M$^+$) 577.1595, found 577.1599.

Example 5

5-Bromo-6-chloro-pyridine-3-sulfonic acid {4-[3-cyclopropylmethyl-1-(2-fluoro-benzyl)-2,6-dioxo-2,3,6,7-tetrahydro-1H-purin-8-ylmethyl]-phenyl}-amide

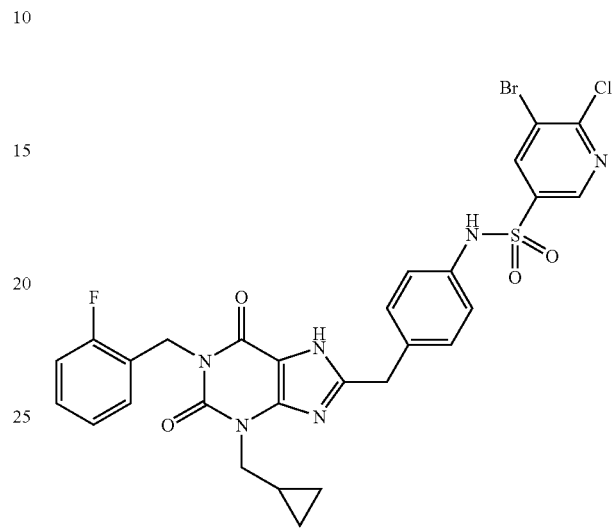

Prepared from 8-(4-amino-benzyl)-3-cyclopropylmethyl-1-(2-fluoro-benzyl)-3,7-dihydro-purine-2,6-dione and 3-fluoro-benzenesulfonyl chloride. Pink solid; EI-HRMS m/e calculated for $C_{28}H_{23}BrClFN_6O_4S$ (M+H)$^+$ 673.0430, found 673.0439.

Example 6

5-Chloro-1,3-dimethyl-1H-pyrazole-4-sulfonic acid {3-[3-cyclopropylmethyl-1-(2-fluoro-benzyl)-2,6-dioxo-2,3,6,7-tetrahydro-1H-purin-8-ylmethyl]-phenyl}-amide

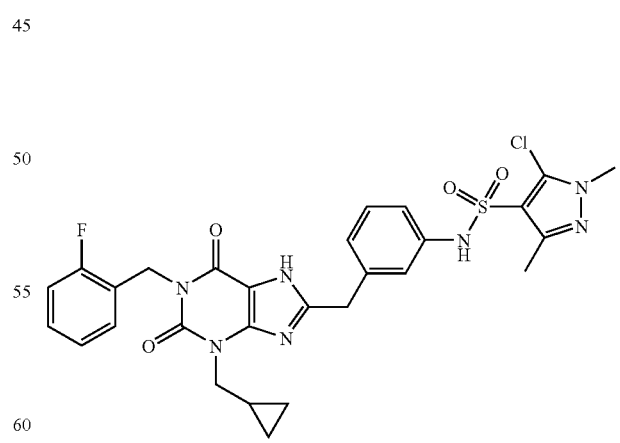

Prepared from 8-(3-amino-benzyl)-3-cyclopropylmethyl-1-(2-fluoro-benzyl)-3,7-dihydro-purine-2,6-dione and 5-chloro-1,3-dimethyl-1H-pyrazole-4-sulfonyl chloride. Light yellow solid; (ES)$^+$-HRMS m/e calculated for $C_{28}H_{27}ClFN_7O_4S$ (M+Na)$^+$ 634.1411, found 634.1410.

Example 7

1,3-Dimethyl-1H-pyrazole-4-sulfonic acid {4-[3-cyclopropylmethyl-1-(2-fluoro-benzyl)-2,6-dioxo-2,3,6,7-tetrahydro-1H-purin-8-ylmethyl]-phenyl}-amide

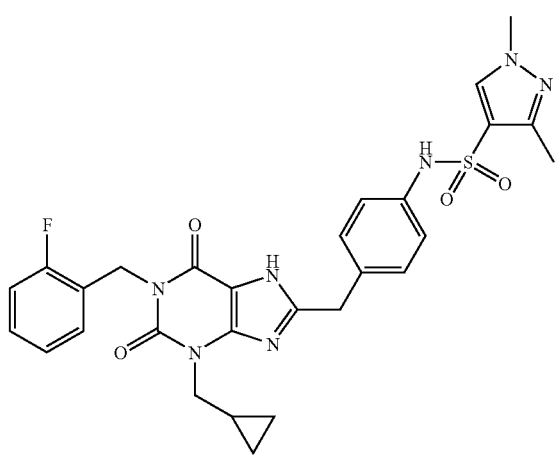

A mixture of 5-chloro-1,3-dimethyl-1H-pyrazole-4-sulfonic acid {4-[3-cyclopropylmethyl-1-(2-fluoro-benzyl)-2,6-dioxo-2,3,6,7-tetrahydro-1H-purin-8-ylmethyl]-phenyl}-amide (300 mg, 0.49 mmol) in methylene chloride (125 mL) and methanol (125 mL) at 25° C. was treated with 10% Pd/C (1.0 g) and sodium acetate (134 mg, 1.22 mmol). The resulting mixture was hydrogenated in a Parr bomb at 50 psi for 24 h. At this time, the reaction was filtered through a pad of celite and was washed with an 8/2 methylene chloride/methanol solution (200 mL). The filtrate was concentrated in vacuo to afford a white solid. This solid was dissolved in a 5/95 methanol/methylene chloride solution. The organics were washed with water (1×25 mL). The aqueous layer was then back-extracted with chloroform (1×50 mL). The combined organics were dried over magnesium sulfate, filtered, and concentrated in vacuo to afford 1,3-dimethyl-1H-pyrazole-4-sulfonic acid {4-[3-cyclopropylmethyl-1-(2-fluoro-benzyl)-2,6-dioxo-2,3,6,7-tetrahydro-1H-purin-8-ylmethyl]-phenyl}-amide (184 mg 65%) as a white solid; (ES)$^+$-HRMS m/e calculated for $C_{28}H_{28}FN_7O_4S$ $(M+H)^+$ 578.1980, found 578.1987.

Example 8

5-Chloro-1,3-dimethyl-1H-pyrazole-4-sulfonic acid {4-[1,3-dimethyl-2,6-dioxo-2,3,6,7-tetrahydro-1H-purin-8-ylmethyl]-phenyl}-amide

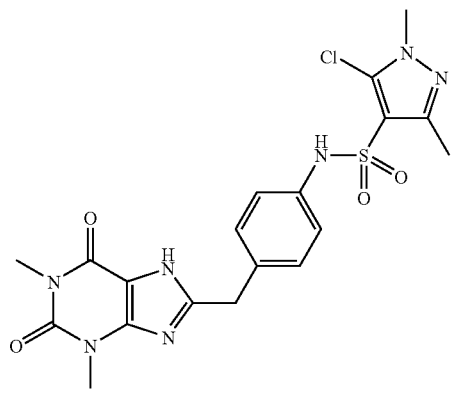

This compound was prepared by a combination of the routes outlined in schemes 1,2 and 4.

Step 1: Preparation of 6-amino-1,3-dimethyl-5-nitroso-1H-pyrimidine-2,4-dione.

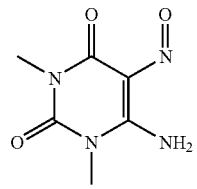

Commercially available 6-amino-1,3-dimethyl-1H-pyrimidine-2,4-dione (10 mmol) was dissolved in 1:1 water/glacial acetic acid (50 mL total volume) at 80° C. and sodium nitrite (20 mmol) added in portions. After the addition was complete the reaction mixture was stirred at 80° C. for 1 hr. Cooled in ice for 30 mins then filtered and washed with water. The precipitate was dried in vacuo to give crude 6-amino-1,3-dimethyl-5-nitroso-1H-pyrimidine-2,4-dione as a red-violet colored solid which was of sufficient purity for subsequent use without additional purification (89%).

Step 2: Preparation of 5,6-diamino-1,3-dimethyl-1H-pyrimidine-2,4-dione.

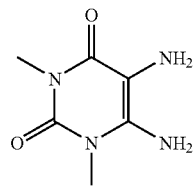

Crude 6-amino-1,3-dimethyl-5-nitroso-1H-pyrimidine-2,4-dione (5 mmol) was suspended in water (7 mL) at 40° C. and treated with sodium dithionite (17.5 mmol). After 20 minutes at 40° C. the reaction mixture was warmed to 80° C. for 30 mins and then cooled in ice for 30 mins. The precipitate was isolated by filtration, washed with cold water and dried in vacuo to give crude 5,6-diamino-1,3-dimethyl-1H-pyrimidine-2,4-dione as a light beige solid which was of sufficient purity for subsequent use without additional purification (80%).

Step 3: Preparation of {4-[(6-amino-1,3-dimethyl-2,4-dioxo-1,2,3,4-tetrahydro-pyrimidin-5-ylcarbamoyl)-methyl]-phenyl}-carbamic acid tert-butyl ester.

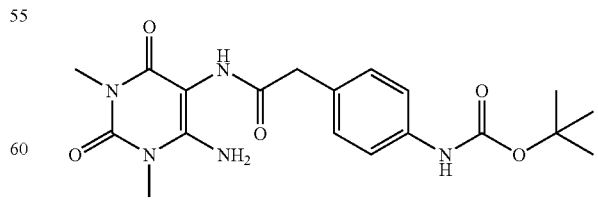

To a solution of (4-tert-butoxycarbonylamino-phenyl)-acetic acid (0.825 mmol) and crude 5,6-diamino-1,3-dimethyl-1H-pyrimidine-2,4-dione (0.75 mmol) in N,N-dimethylformamide (3 mL) under argon at 25° C. was added 1-(3-dimethylaminopropyl)-3-ethylcarbodiimide hydrochloride(0.825 mmol) and 4-dimethylaminopyridine (0.15 mmol). The reaction was stirred at 25° C. for 18 h. At this time, the reaction was concentrated in vacuo. The residue was triturated with water and the resulting solid collected by filtration, washed well with water and dried in vacuo to afford crude {4-[(6-amino-1,3-dimethyl-2,4-dioxo-1,2,3,4-tetrahydro-pyrimidin-5-ylcarbamoyl)-methyl]-phenyl}-carbamic acid tert-butyl ester as a light beige solid which was of sufficient purity for subsequent use without additional purification (87%).

Step 4: Preparation of N-(6-amino-1,3-dimethyl-2,4-dioxo-1,2,3,4-tetrahydro-pyrimidin-5-yl)-2-(4-amino-phenyl)-acetamide hydrochloride salt.

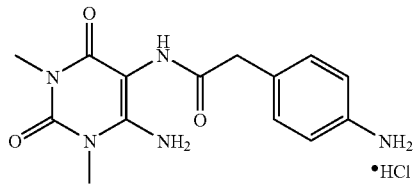

Crude {4-[(6-amino-1,3-dimethyl-2,4-dioxo-1,2,3,4-tetrahydro-pyrimidin-5-ylcarbamoyl)-methyl]-phenyl}-carbamic acid tert-butyl ester (0.65 mmol) was added to a 4M solution of hydrogen chloride in p-dioxane (10 mL) and the mixture stirred at ambient temperature for 2 hrs. The precipitate was isolated by filtration, washed with p-dioxane and ether then dried in vacuo to give crude N-(6-amino-1,3-dimethyl-2,4-dioxo-1,2,3,4-tetrahydro-pyrimidin-5-yl)-2-(4-amino-phenyl)-acetamide hydrochloride salt as a light beige solid which was of sufficient purity for subsequent use without additional purification (quantitative).

Step 5: Preparation of 8-(4-amino-benzyl)-1,3-dimethyl-3,7-dihydro-purine-2,6-dione.

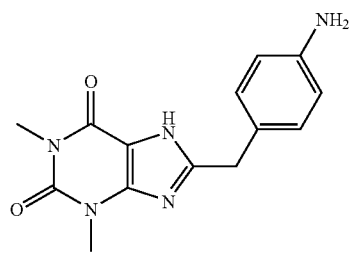

To a solution of crude N-(6-amino-1,3-dimethyl-2,4-dioxo-1,2,3,4-tetrahydro-pyrimidin-5-yl)-2-(4-amino-phenyl)-acetamide hydrochloride salt (0.68 mmol) in methanol (35 mL) was added 10% w/v aqueous sodium hydroxide (3.4 mL) and the mixture heated to 50° C. for 7 hrs. The reaction mixture was concentrated in vacuo to dryness and the residue triturated with warm tetrahydrofuran and filtered to remove insoluble inorganic material. The filtrate was concentrated in vacuo to give crude 8-(4-amino-benzyl)-1,3-dimethyl-3,7-dihydro-purine-2,6-dione which was of sufficient purity for subsequent use without additional purification (58%).

Step 6: Preparation of 5-chloro-1,3-dimethyl-1H-pyrazole-4-sulfonic acid {4-[1,3-dimethyl-2,6-dioxo-2,3,6,7-tetrahydro-1H-purin-8-ylmethyl]-phenyl}-amide.

To a solution of crude 8-(4-amino-benzyl)-1,3-dimethyl-3,7-dihydro-purine-2,6-dione (0.2 mmol) in pyridine (2 mL) at 0° C. was added 5-chloro-1,3-dimethyl-1H-pyrazole-4-sulfonyl chloride (0.2 mmol) and the mixture left to stir and warm slowly to ambient temperature overnight. The reaction mixture was poured into ethyl acetate, washed with 1M aqueous hydrochloric acid until all pyridine was removed from the organic phase and the combined aqueous washings back extracted with ethyl acetate. The combined organic layers were dried and concentrated in vacuo to give an orange solid. Purified by trituration with warm acetonitrile to give 5-chloro-1,3-dimethyl-1H-pyrazole-4-sulfonic acid {4-[1,3-dimethyl-2,6-dioxo-2,3,6,7-tetrahydro-1H-purin-8-ylmethyl]-phenyl}-amide as a pale orange solid (51%); EI-HRMS m/e calculated for $C_{19}H_{20}ClN_7O_4S$ (M$^+$) 477.0986, found 477.0994.

Example 9

1,3-Dimethyl-1H-pyrazole-4-sulfonic acid [4-(1,3-dimethyl-2,6-dioxo-2,3,6,7-tetrahydro-1H-purin-8-ylmethyl)-phenyl]-amide

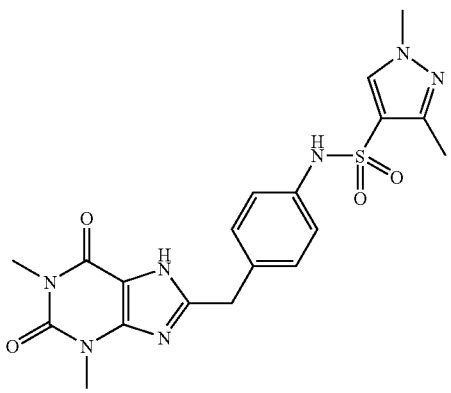

5-Chloro-1,3-dimethyl-1H-pyrazole-4-sulfonic acid {4-[1,3-dimethyl-2,6-dioxo-2,3,6,7-tetrahydro-1H-purin-8-ylmethyl]-phenyl}-amide (0.082 mmol) was dissolved in methanol (70 mL) and dichloromethane (10 mL) and the reaction vessel flushed with argon before adding 10% palladium on carbon (100 mg). The reaction vessel was charged with hydrogen gas at 50 psi pressure and shaken for 24 hrs. Additional 10% palladium on carbon (50 mg) was added and hydrogenolysis continued at 50 psi pressure of hydrogen gas for an additional 24 hrs. At this time no starting material remained. The reaction mixture was filtered through celite and concentrated in vacuo. The crude product was purified by chromatography using silica eluted with 10% v/v methanol in chloroform to give after concentration in vacuo 1,3-dimethyl-1H-pyrazole-4-sulfonic acid [4-(1,3-dimethyl-2,6-dioxo-2,3,6,7-tetrahydro-1H-purin-8-ylmethyl)-phenyl]-amide as a colorless solid (38%); EI-HRMS m/e calculated for $C_{19}H_{21}N_7O_4S$ (M$^+$) 443.1376, found 443.1364.

Example 10

N-(5-{4-[3-Cyclopropylmethyl-1-(2-fluoro-benzyl)-2,6-dioxo-2,3,6,7-tetrahydro-1H-purin-8-ylmethyl]-phenylsulfamoyl}-4-methyl-thiazol-2-yl)-acetamide

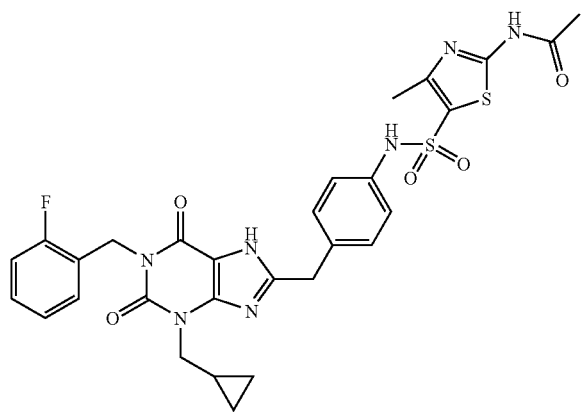

Step 1: Preparation of 2-[4-(2-acetylamino-4-methyl-thiazole-5-sulfonylamino)-phenyl]-N-[6-amino-1-cyclopropylmethyl-3-(2-fluoro-benzyl)-2,4-dioxo-1,2,3,4-tetrahydro-pyrimidin-5-yl]-acetamide.

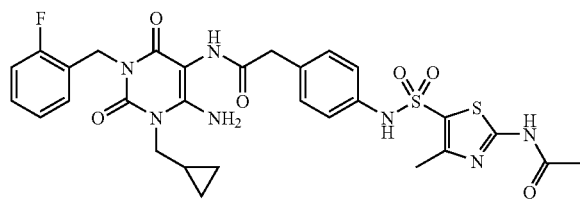

A solution of N-[6-amino-1-cyclopropylmethyl-3-(2-fluoro-benzyl)-2,4-dioxo-1,2,3,4-tetrahydro-pyrimidin-5-yl]-2-(4-amino-phenyl)-acetamide (prepared as in Example 1, 75 mg, 0.16 mmol) in pyridine (1.6 mL) was stirred at 25° C. for 5 min. This solution was then treated with 2-acetylamino-4-methyl-thiazole-5-sulfonyl chloride (44 mg, 0.17 mmol). The reaction mixture was stirred at 25° C. for 24 h. The reaction mixture was then poured into a mixture of methylene chloride (50 mL) and a 1.0N aqueous hydrochloric acid solution (10 mL). This mixture was extracted with a 1/9 methanol/methylene chloride solution (1×50 mL). The organics were dried over magnesium sulfate, filtered, and concentrated in vacuo. Flash chromatography (Merck Silica gel 60, 230–400 mesh, 7/93 methanol/methylene chloride) afforded 2-[4-(2-acetylamino-4-methyl-thiazole-5-sulfonylamino)-phenyl]-N-[6-amino-1-cyclopropylmethyl-3-(2-fluoro-benzyl)-2,4-dioxo-1,2,3,4-tetrahydro-pyrimidin-5-yl]-acetamide (56.4 mg, 54%) as an off-white solid; FAB-HRMS m/e calculated for $C_{29}H_{30}FN_7O_6S_2$ (M+) 655.1683, found 655.1679

Step 2: Preparation of N-(5-{4-[3-cyclopropylmethyl-1-(2-fluoro-benzyl)-2,6-dioxo-2,3,6,7-tetrahydro-1H-purin-8-ylmethyl]-phenylsulfamoyl}-4-methyl-thiazol-2-yl)-acetamide.

A solution of 2-[4-(2-acetylamino-4-methyl-thiazole-5-sulfonylamino)-phenyl]-N-[6-amino-1-cyclopropylmethyl-3-(2-fluoro-benzyl)-2,4-dioxo-1,2,3,4-tetrahydro-pyrimidin-5-yl]-acetamide (56 mg, 0.085 mmol) in methanol warmed to 50° C. was treated with a 10% aqueous sodium hydroxide solution (0.34 mL, 0.085 mmol). The reaction was stirred at 50° C. for 6 h. At this time, the reaction was concentrated in vacuo, diluted with water, and acidified to pH=2 with a 1.0N aqueous hydrochloric acid solution (0.9 mL). This mixture was cooled in an ice-bath. The resulting solids were collected by filtration, washed with water, and dried in vacuo. HPLC (20–80% acetonitrile/water) afforded N-(5-{4-[3-cyclopropylmethyl-1-(2-fluoro-benzyl)-2,6-dioxo-2,3,6,7-tetrahydro-1H-purin-8-ylmethyl]-phenylsulfamoyl}-4-methyl-thiazol-2-yl)-acetamide (16.1 mg, 29.7%) as a white solid; FAB-HRMS m/e calculated for $C_{29}H_{28}FN_7O_5S_2$ (M+H)+ 638.1656, found 638.1641; and 2-amino-4-methyl-thiazole-5-sulfonic acid {4-[3-cyclopropylmethyl-1-(2-fluoro-benzyl)-2,6-dioxo-2,3,6,7-tetrahydro-1H-purin-8-ylmethyl]-phenyl}-amide trifluoro-acetic acid salt (5.4 mg, 10%) as a white solid; FAB-HRMS m/e calculated for $C_{27}H_{26}FN_7O_4S_2$ (M+H)+ 596.1550, found 596.1547.

The compounds cited in examples 11 to 18 were obtained in an analogous manner to that described in example 10.

Example 11

2-Amino-4-methyl-thiazole-5-sulfonic acid {4-[3-cyclopropylmethyl-1-(2-fluoro-benzyl)-2,6-dioxo-2,3,6,7-tetrahydro-1H-purin-8-ylmethyl]-phenyl}-amide trifluoro-acetic acid salt

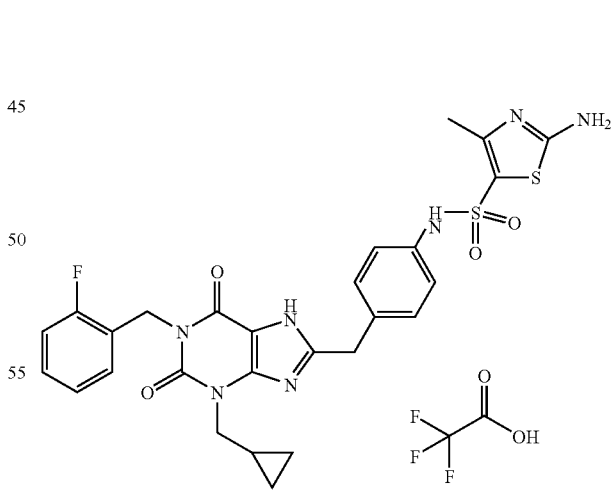

Prepared from 2-[4-(2-acetylamino-4-methyl-thiazole-5-sulfonylamino)-phenyl]-N-[6-amino-1-cyclopropylmethyl-3-(2-fluoro-benzyl)-2,4-dioxo-1,2,3,4-tetrahydro-pyrimidin-5-yl]-acetamide. White solid; FAB-HRMS m/e calculated for $C_{27}H_{26}FN_7O_4S_2$ (M+H)+ 596.1550, found 596.1547.

Example 12

3,5-Dimethyl-isoxazole-4-sulfonic acid {4-[3-cyclopropylmethyl-1-(2-fluoro-benzyl)-2,6-dioxo-2,3,6,7-tetrahydro-1H-purin-8-ylmethyl]-phenyl}-amide

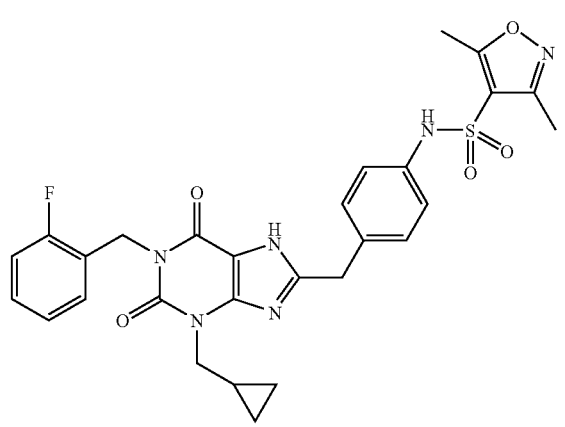

Prepared from N-[6-Amino-1-cyclopropylmethyl-3-(2-fluoro-benzyl)-2,4-dioxo-1,2,3,4-tetrahydro-pyrimidin-5-yl]-2-[4-(3,5-dimethyl-isoxazole-4-sulfonylamino)-phenyl]-acetamide. White solid; FAB-HRMS m/e calculated for $C_{28}H_{27}FN_6O_5S$ (M+H)$^+$ 579.1826, found 579.1822.

Example 13

1,2-Dimethyl-1H-imidazole-4-sulfonic acid {4-[3-cyclopropylmethyl-1-(2-fluoro-benzyl)-2,6-dioxo-2,3,6,7-tetrahydro-1H-purin-8-ylmethyl]-phenyl}-amide

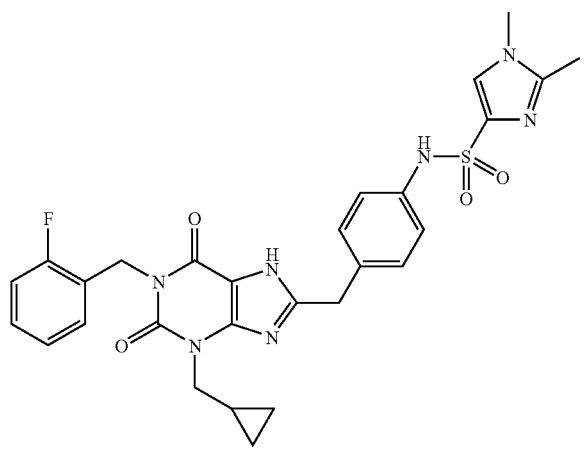

Prepared from N-[6-Amino-1-cyclopropylmethyl-3-(2-fluoro-benzyl)-2,4-dioxo-1,2,3,4-tetrahydro-pyrimidin-5-yl]-2-[4-(1,2-dimethyl-1H-imidazole-4-sulfonylamino)-phenyl]-acetamide. White solid; FAB-HRMS m/e calculated for $C_{28}H_{28}FN_7O_4S$ (M+H)$^+$ 578.1986, found 578.1976.

Example 14

1-Methyl-1H-imidazole-4-sulfonic acid {4-[3-cyclopropylmethyl-1-(2-fluoro-benzyl)-2,6-dioxo-2,3,6,7-tetrahydro-1H-purin-8-ylmethyl]-phenyl}-amide

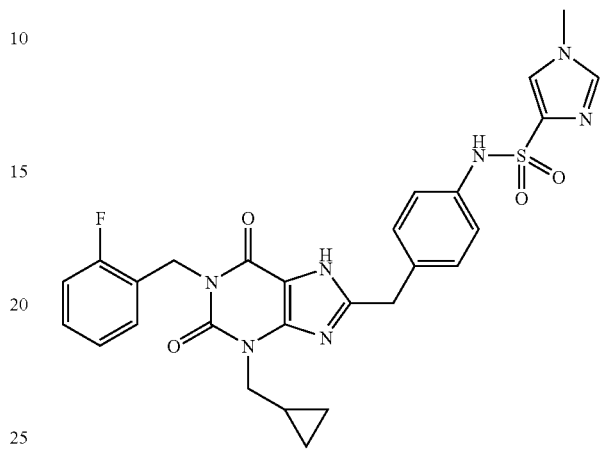

Prepared from N-[6-Amino-1-cyclopropylmethyl-3-(2-fluoro-benzyl)-2,4-dioxo-1,2,3,4-tetrahydro-pyrimidin-5-yl]-2-[4-(1-methyl-1H-imidazole-4-sulfonylamino)-phenyl]-acetamide. White solid; LRMS for $C_{27}H_{26}FN_7O_4S$ (M+H)$^+$ at m/z=564.

Example 15

1-Methyl-1H-imidazole-4-sulfonic acid {4-[3-butyl-1-(2-fluoro-benzyl)-2,6-dioxo-2,3,6,7-tetrahydro-1H-purin-8-ylmethyl]-phenyl}-amide hydrochloride salt

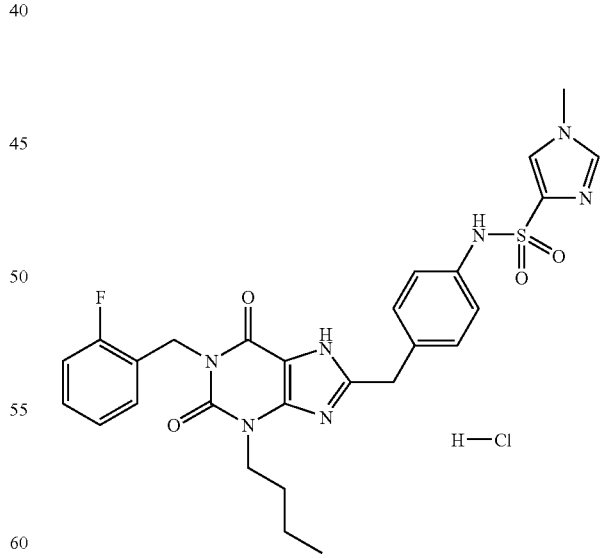

Prepared from N-[6-Amino-1-butyl-3-(2-fluoro-benzyl)-2,4-dioxo-1,2,3,4-tetrahydro-pyrimidin-5-yl]-2-[4-(1-methyl-1H-imidazole-4-sulfonylamino)-phenyl]-acetamide. White solid; FAB-HRMS m/e calculated for $C_{27}H_{28}FN_7O_4S$ (M+H)$^+$ 566.1986, found 566.1971.

Example 16

1-Methyl-1H-imidazole-4-sulfonic acid {4-[3-butyl-1-(2-fluoro-benzyl)-2,6-dioxo-2,3,6,7-tetrahydro-1H-purin-8-ylmethyl]-phenyl}-amide trifluoroacetic acid salt

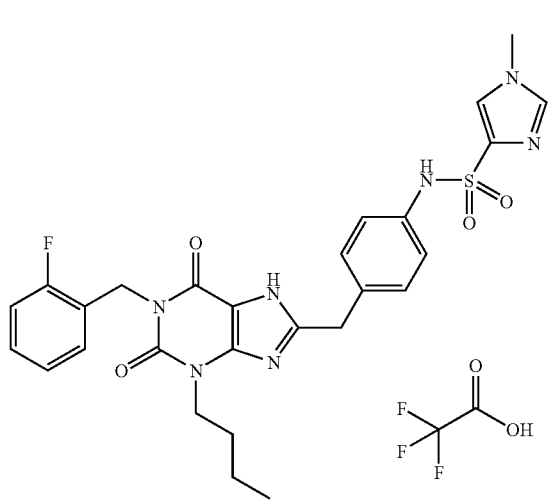

Prepared from N-[6-Amino-1-butyl-3-(2-fluoro-benzyl)-2,4-dioxo-1,2,3,4-tetrahydro-pyrimidin-5-yl]-2-[4-(1-methyl-1H-imidazole-4-sulfonylamino)-phenyl]-acetamide. White solid; LRMS for $C_{27}H_{28}FN_7O_4S$ $(M+H)^+$ at m/z=566.

Example 17

N-{4-[3-Cyclopropylmethyl-1-(2-fluoro-benzyl)-2,6-dioxo-2,3,6,7-tetrahydro-1H-purin-8-ylmethyl]-phenyl}-N,N-dimethylsulfamide

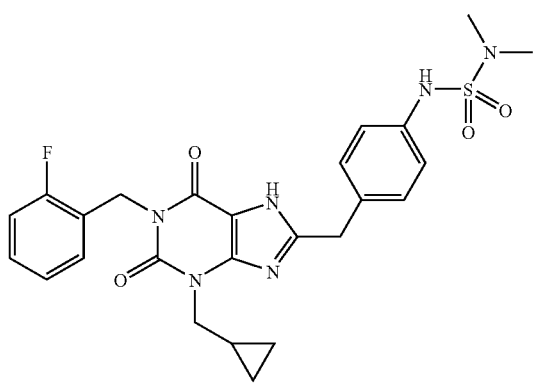

Prepared from N-[6-Amino-1-cyclopropylmethyl-3-(2-fluoro-benzyl)-2,4-dioxo-1,2,3,4-tetrahydro-pyrimidin-5-yl]-2-[4-(3,5-dimethyl-isoxazole-4-sulfonylamino)-phenyl]-acetamide. Off-white solid; FAB-HRMS m/e calculated for $C_{25}H_{27}FN_6O_4S$ $(M+H)^+$ 527.1877, found 527.1858.

Example 18

5-Chloro-1,3-dimethyl-1H-pyrazole-4-sulfonic acid {4-[3-cyclopropylmethyl-1-(2-fluoro-benzyl)-2,6-dioxo-2,3,6,7-tetrahydro-1H-purin-8-ylmethyl]-phenyl}-methyl-amide

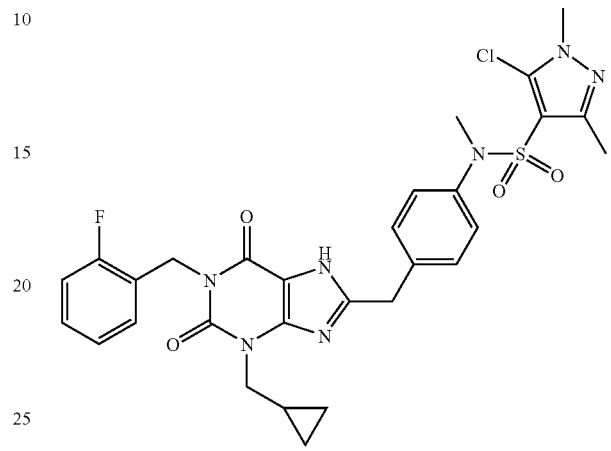

Step 1: Preparation of [4-(tert-butoxycarbonyl-methyl-amino)-phenyl]-acetic acid.

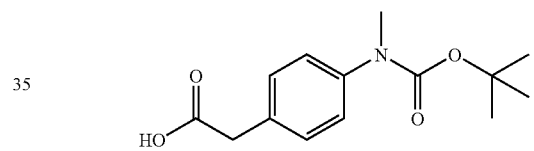

To a solution of [4-(tert-butoxycarbonyl-methyl-amino)-phenyl]-acetic acid methyl ester (prepared according to the procedure of Hay et al. as described in *J. Chem. Soc. Perkin Trans I.* 1999, 19, 2759) (2.68 mmol) in methanol (10 mL) was added 1.0M aqueous lithium hydroxide solution (13.7 mL) and the mixture heated to 50° C. for 35 mins. The reaction mixture was cooled in an ice bath then washed with ether (25 mL), acidified with 3.0M aqueous hydrochloric acid to pH=4 while stirring and cooling in an ice bath. The precipitate was isolated by filtration, washed with water and dried in vacuo to give [4-(tert-butoxycarbonyl-methyl-amino)-phenyl]-acetic acid as a colorless solid (70%).

Step 2: Preparation of (4-{[6-amino-3-(2-fluoro-benzyl)-2,4-dioxo-1,2,3,4-tetrahydro-pyrimidin-5-ylcarbamoyl]-methyl}-phenyl)-methyl-carbamic acid tert-butyl ester.

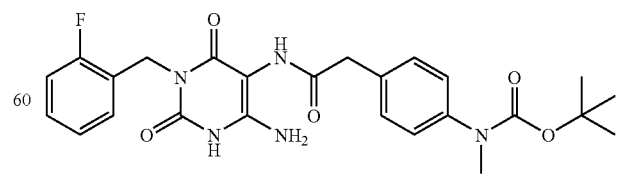

Prepared by the same procedure as described for the preparation of (4-{[6-amino-3-(2-fluoro-benzyl)-2,4-dioxo-1,2,3,4-tetrahydro-pyrimidin-5-ylcarbamoyl]-methyl}-phenyl)-carbamic acid tert-butyl ester (example 1, step 4) except that [4-(tert-butoxycarbonyl-methyl-amino)-phenyl]-acetic acid was used in place of (4-tert-butoxycarbonylamino-phenyl)-acetic acid. Crude (4-{[6-amino-3-(2-fluoro-benzyl)-2,4-dioxo-1,2,3,4-tetrahydro-pyrimidin-5-ylcarbamoyl]-methyl}-phenyl)-methyl-carbamic acid tert-butyl ester was obtained as a yellow solid which was of sufficient purity for subsequent used without additional purification.

Step 3: Preparation of (4-{[6-amino-1-cyclopropylmethyl-3-(2-fluoro-benzyl)-2,4-dioxo-1,2,3,4-tetrahydro-pyrimidin-5-ylcarbamoyl]-methyl}-phenyl)-methyl-carbamic acid tert-butyl ester.

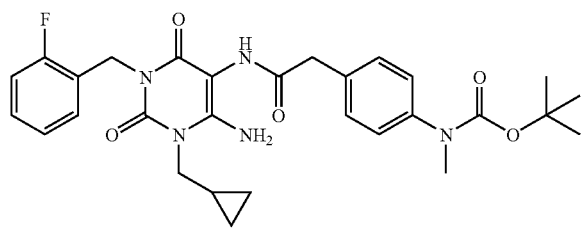

Prepared by the same procedure as described for the preparation of (4-{[6-amino-1-cyclopropylmethyl-3-(2-fluoro-benzyl)-2,4-dioxo-1,2,3,4-tetrahydro-pyrimidin-5-ylcarbamoyl]-methyl}-phenyl)-carbamic acid tert-butyl ester (example 1, step 5) except that (4-{[6-amino-3-(2-fluoro-benzyl)-2,4-dioxo-1,2,3,4-tetrahydro-pyrimidin-5-ylcarbamoyl]-methyl}-phenyl)-methyl-carbamic acid tert-butyl ester was used in place of (4-{[6-amino-1-cyclopropylmethyl-3-(2-fluoro-benzyl)-2,4-dioxo-1,2,3,4-tetrahydro-pyrimidin-5-ylcarbamoyl]-methyl}-phenyl)-carbamic acid tert-butyl ester. Purified by chromatography using silica eluted with 3% v/v methanol in chloroform to give (4-{[6-amino-1-cyclopropylmethyl-3-(2-fluoro-benzyl)-2,4-dioxo-1,2,3,4-tetrahydro-pyrimidin-5-ylcarbamoyl]-methyl}-phenyl)-methyl-carbamic acid tert-butyl ester as a colorless solid foam (63% yield from [4-(tert-butoxycarbonyl-methyl-amino)-phenyl]-acetic acid).

Step 4: Preparation of N-[6-amino-1-cyclopropylmethyl-3-(2-fluoro-benzyl)-2,4-dioxo-1,2,3,4-tetrahydro-pyrimidin-5-yl]-2-(4-methylamino-phenyl)-acetamide, hydrochloride.

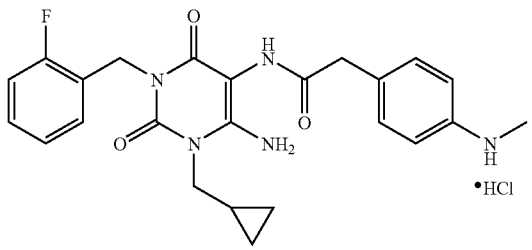

Prepared by the same method as described for the preparation of N-[6-amino-1-cyclopropylmethyl-3-(2-fluoro-benzyl)-2,4-dioxo-1,2,3,4-tetrahydro-pyrimidin-5-yl]-2-(4-amino-phenyl)-acetamide, hydrochloride salt (example 1, step 6) except that (4-{[6-amino-1-cyclopropylmethyl-3-(2-fluoro-benzyl)-2,4-dioxo-1,2,3,4-tetrahydro-pyrimidin-5-ylcarbamoyl]-methyl}-phenyl)-methyl-carbamic acid tert-butyl ester was used in place of (4-{[6-amino-1-cyclopropylmethyl-3-(2-fluoro-benzyl)-2,4-dioxo-1,2,3,4-tetrahydro-pyrimidin-5-ylcarbamoyl]-methyl}-phenyl)-carbamic acid tert-butyl ester. N-[6-Amino-1-cyclopropylmethyl-3-(2-fluoro-benzyl)-2,4-dioxo-1,2,3,4-tetrahydro-pyrimidin-5-yl]-2-(4-methylamino-phenyl)-acetamide; hydrochloride was obtained as a green solid which was of sufficient purity for subsequent used without additional purification.

Step 5: Preparation of N-[6-amino-1-cyclopropylmethyl-3-(2-fluoro-benzyl)-2,4-dioxo-1,2,3,4-tetrahydro-pyrimidin-5-yl]-2-{4-[(5-chloro-1,3-dimethyl-1H-pyrazole-4-sulfonyl)-methyl-amino]-phenyl}-acetamide.

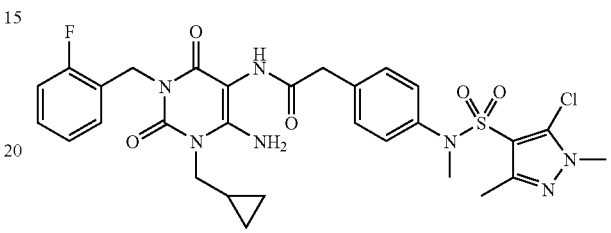

To a solution of N-[6-amino-1-cyclopropylmethyl-3-(2-fluoro-benzyl)-2,4-dioxo-1,2,3,4-tetrahydro-pyrimidin-5-yl]-2-(4-methylamino-phenyl)-acetamide;

hydrochloride (0.246 mmol) in pyridine (2.5 mL) was added 5-chloro-1,3-dimethyl-pyrazole-4-sulfonyl chloride (0.295 mmol) and the mixture stirred at ambient temperature for 48 hrs. The reaction mixture was poured into dichloromethane and washed twice with 1.0M aqueous hydrochloric acid, washed with brine, dried with magnesium sulfate, filtered and concentrated in vacuo. Purified by chromatography using silica eluted with 3% v/v methanol in dichloromethane to give N-[6-amino-1-cyclopropylmethyl-3-(2-fluoro-benzyl)-2,4-dioxo-1,2,3,4-tetrahydro-pyrimidin-5-yl]-2-{4-[(5-chloro-1,3-dimethyl-1H-pyrazole-4-sulfonyl)-methyl-amino]-phenyl}-acetamide as an off white solid (53%).

Step 6: Preparation of 5-chloro-1,3-dimethyl-1H-pyrazole-4-sulfonic acid {4-[3-cyclopropylmethyl-1-(2-fluoro-benzyl)-2,6-dioxo-2,3,6,7-tetrahydro-1H-purin-8-ylmethyl]-phenyl}-methyl-amide.

To a solution of N-[6-amino-1-cyclopropylmethyl-3-(2-fluoro-benzyl)-2,4-dioxo-1,2,3,4-tetrahydro-pyrimidin-5-yl]-2-{4-[(5-chloro-1,3-dimethyl-1H-pyrazole-4-sulfonyl)-methyl-amino]-phenyl}-acetamide (0.119 mmol) in methanol (2 mL) was added 10% w/v aqueous sodium hydroxide solution (1 mL) and the mixture heated to 50° C. for 1.5 hrs. The methanol was removed in vacuo and the aqueous residue acidified to pH=4 with 1.0M aqueous hydrochloric acid. The aqueous suspension was extracted with chloroform, the combined chloroform extracts washed with brine, dried with magnesium sulfate, filtered and concentrated in vacuo. the residue was triturated with acetonitrile to give 5-chloro-1,3-dimethyl-1H-pyrazole-4-sulfonic acid {4-[3-cyclopropylmethyl-1-(2-fluoro-benzyl)-2,6-dioxo-2,3,6,7-tetrahydro-1H-purin-8-ylmethyl]-phenyl}-methyl-amide as a colorless solid (50%); (ES)$^+$-HRMS m/e calculated for $C_{29}H_{29}ClFN_7O_4S$ (M+Na)$^+$ 648.1566, found 648.1566.

Example 19

Quinoline-8-sulfonic acid {4-[3-cyclopropylmethyl-1-(2-fluoro-benzyl)-2,6-dioxo-2,3,6,7-tetrahydro-1H-purin-8-ylmethyl]-phenyl}-amide

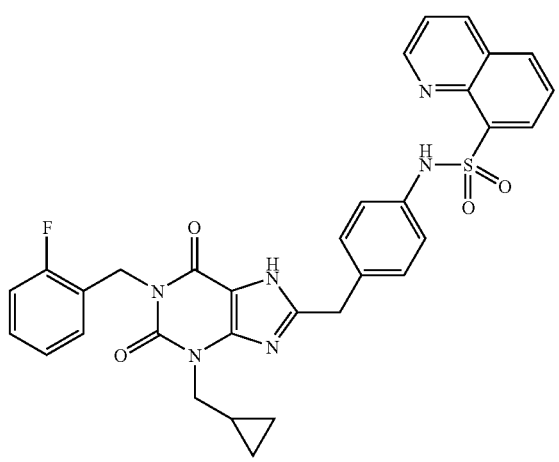

This compound was prepared by the routes shown in schemes 2 and 4. 8-(4-Amino-benzyl)-3-cyclopropylmethyl-1-(2-fluoro-benzyl)-3,7-dihydro-purine-2,6-dione was condensed with 8-quinolinesulfonyl chloride under standard conditions to give the stated sulfonamide. Recrystallization from acetonitrile gave the pure product as an off white solid (53%); $^1$H NMR(DMSO-d$_6$, 300 MHz) $\delta_H$13.45 (s, 1H), 10.12 (s, 1H), 9.21 (dd, J=4.2, 1.1 Hz, 1H), 8.59 (dd, J=8.4, 1.8 Hz, 1H), 8.41 (dd, J=7.3, 1.5 Hz, 1H), 8.33 (dd, J=7.7, 1.5 Hz, 1H), 7.82–7.73 (m, 2H), 7.45–7.00 (m, 8H), 5.16 (s, 2H), 3.93 (s, 2H), 3.86 (d, J=7.3 Hz, 2H), 1.30–1.10 (m, 1H) and 0.50–0.30 (m, 4H); EI-HRMS m/e calculated for C$_{32}$H$_{27}$FN$_6$O$_4$S (M$^+$) 610.1798, found 610.1804.

Example 20

N-(4-{4-[3-Cyclopropylmethyl-1-(2-fluoro-benzyl)-2,6-dioxo-2,3,6,7-tetrahydro-1H-purin-8-ylmethyl]-phenylsulfamoyl}-phenyl)-acetamide

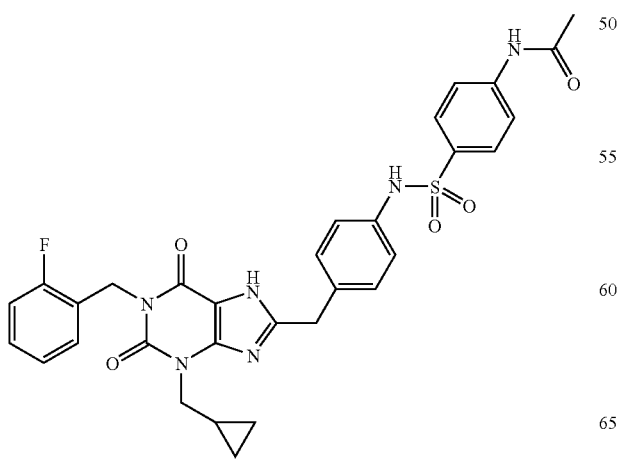

8-(4-Amino-benzyl)-3-cyclopropylmethyl-1-(2-fluoro-benzyl)-3,7-dihydro-purine-2,6-dione was condensed with 4-acetamidobenzenesulfonyl chloride under the conditions previously described to give the stated sulfonamide. Recrystallized from acetonitrile to give the pure product as an off-white solid (68%); $^1$H NMR (DMSO-d$_6$, 300 MHz) $\delta_H$13.53 (s, 1H), 10.36 (s, 1H), 10.23 (s, 1H), 7.75 (s, 4H), 7.40–7.05 (m, 8H), 5.19 (s, 2H), 4.02 (s, 2H), 3.91 (d, J=7.0 Hz, 2H), 2.13 (s, 3H), 1.35–1.15 (m, 1H) and 0.55–0.35 (m, 4H); EI-HRMS m/e calculated for C$_{31}$H$_{29}$FN$_6$O$_5$S (M$^+$) 616.1904, found 616.1922.

Example 21

N-[4-(1-Benzyl-3-butyl-2,6-dioxo-2,3,6,7-tetrahydro-1H-purin-8-ylmethyl)-phenyl]-4-methyl-benzenesulfonamide

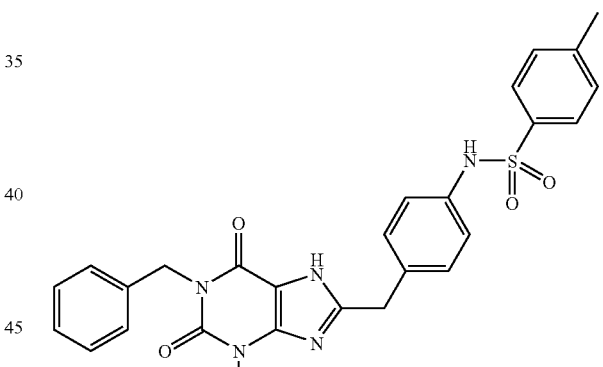

8-(4-Amino-benzyl)-3-cyclopropylmethyl-1-(2-fluoro-benzyl)-3,7-dihydro-purine-2,6-dione was condensed with 4-toluenesulfonyl chloride under the conditions previously described to give the stated sulfonamide as an off white solid (59%); $^1$H NMR(DMSO-d$_6$, 300 MHz) $\delta$13.49 (s, 1H), 10.28 (s, 1H), 7.70 (d, J=8.1 Hz, 2H), 7.45–7.25 (m, 7H), 7.21 (d, J=8.4 Hz, 2H), 7.09 (d, J=8.4 Hz, 2H), 5.12 (s, 2H), 4.02 (s, 2H), 4.01 (t, J=7.0 Hz, 2H), 2.39 (s, 3H), 1.75–1.60 (m, 2H), 1.40–1.25 (m, 2H), 0.94 (t, J=7.5 Hz, 3H); EI-HRMS m/e calculated for C$_{30}$H$_{31}$N$_5$O$_4$S (M$^+$) 557.2097, found 557.2090.

Example 22

Pyridine-3-sulfonic acid {4-[3-cyclopropylmethyl-1-(2-fluoro-benzyl)-2,6-dioxo-2,3,6,7-tetrahydro-1H-purin-8-ylmethyl]-phenyl}-amide trifluoro-acetic acid salt

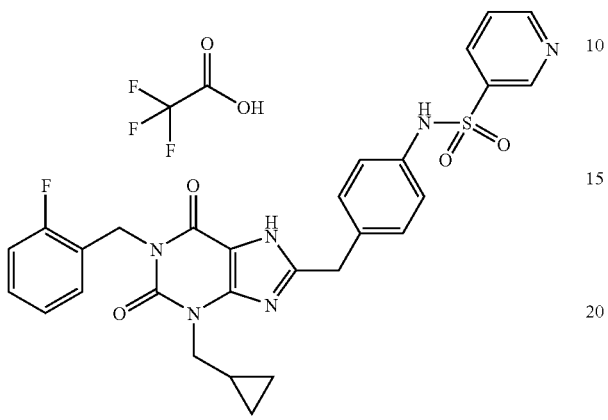

A solution of 5-bromo-6-chloro-pyridine-3-sulfonic acid {4-[3-cyclopropylmethyl-1-(2-fluoro-benzyl)-2,6-dioxo-2,3,6,7-tetrahydro-1H-purin-8-ylmethyl]-phenyl}-amide (prepared as in Example 5, 37.5 mg, 0.056 mmol) in ethanol (50 mL) at 25° C. was treated with 10% Pd/C (4.0 mg). The reaction mixture was submitted to hydrogenation conditions in a Parr bomb at 48 psi for 1 h. At this time, the reaction mixture was filtered through a pad of celite and washed with ethanol followed by a warm solution of 90/10 methylene chloride/ethanol. The filtrated was concentrated in vacuo. The residue was resubmitted to the reaction conditions with triethylamine (0.015 mL, 0.11 mmol) and was hydrogenated for 4 d. At this time, the reaction was filtered through a pad of celite and washed with solvent. The filtrate was concentrated in vacuo.

The resulting residue was purified by HPLC (20–70% acetonitrile/water) to afford pyridine-3-sulfonic acid {4-[3-cyclopropylmethyl-1-(2-fluoro-benzyl)-2,6-dioxo-2,3,6,7-tetrahydro-1H-purin-8-ylmethyl]-phenyl}-amide trifluoro-acetic acid salt (5.2 mg, 13.8%); LRMS for $C_{28}H_{25}FN_6O_4S$ $(M+H)^+$ at m/z=561.

Example 23

N-{4-[3-Cyclopropylmethyl-1-(2-fluoro-benzyl)-2,6-dioxo-2,3,6,7-tetrahydro-1H-purin-8-ylmethyl]-phenyl}-methanesulfonamide

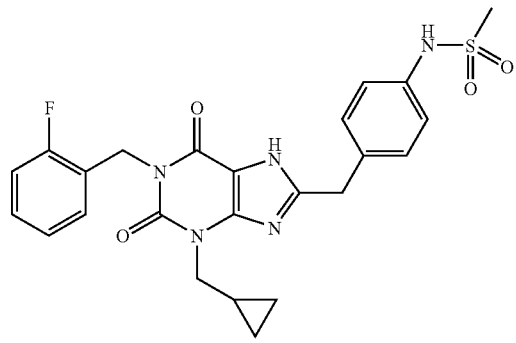

8-(4-Amino-benzyl)-3-cyclopropylmethyl-1-(2-fluoro-benzyl)-3,7-dihydro-purine-2,6-dione was condensed with methanesulfonyl chloride under the conditions previously described to give the stated sulfonamide as an off-white solid (28%); $^1$H NMR(DMSO-d$_6$, 300 MHz) $\delta_H$ 13.42 (s, 1H), 9.61 (s, 1H), 7.30–6.90 (m, 8H), 5.04 (s, 2H), 3.94 (s, 2H), 3.77 (d, J=6.6 Hz, 2H), 2.87 (s, 3H), 1.25–1.05 (m, 1H), 0.40–0.25 (m, 4H); EI-HRMS m/e calculated for $C_{24}H_{24}FN_5O_4S$ (M$^+$) 497.1533, found 497.1528.

Example 24

N-[4-(1-Benzyl-3-butyl-2,6-dioxo-2,3,6,7-tetrahydro-1H-purin-8-ylmethyl)-phenyl]-methanesulfonamide

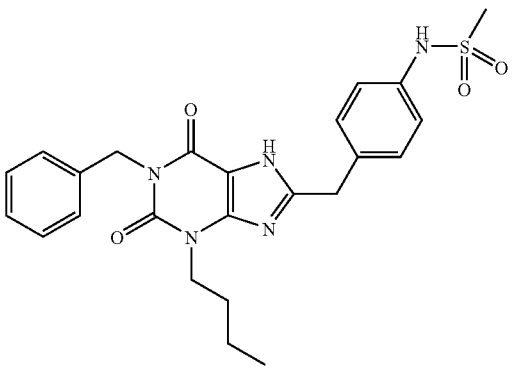

8-(4-Amino-benzyl)-1-benzyl-3-butyl-3,7-dihydro-purine-2,6-dione was condensed with methanesulfonyl chloride under the conditions previously described to give the stated sulfonamide as a pale brown solid (35%); $^1$H NMR (DMSO-d$_6$, 300 MHz) $\delta_H$13.54 (s, 1H), 9.76 (s, 1H), 7.45–7.25 (m, 7H), 7.22 (d, J=8.4 Hz, 2H), 5.14 (s, 2H), 4.10 (s, 2H), 4.04 (t, J=7.1 Hz, 2H), 3.03 (s, 3H), 1.80–1.65 (m, 2H), 1.40–1.25 (m, 2H), 0.96 (t, J=7.3 Hz, 3H); EI-HRMS m/e calculated for $C_{24}H_{27}N_5O_4S$ (M$^+$) 481.1784, found 481.1781.

Example 25

5-Chloro-1,3-dimethyl-1H-pyrazole-4-sulfonic acid {6-[3-butyl-1-(2-fluoro-benzyl)-2,6-dioxo-2,3,6,7-tetrahydro-1H-purin-8-ylmethyl]-pyridin-3-yl}-amide

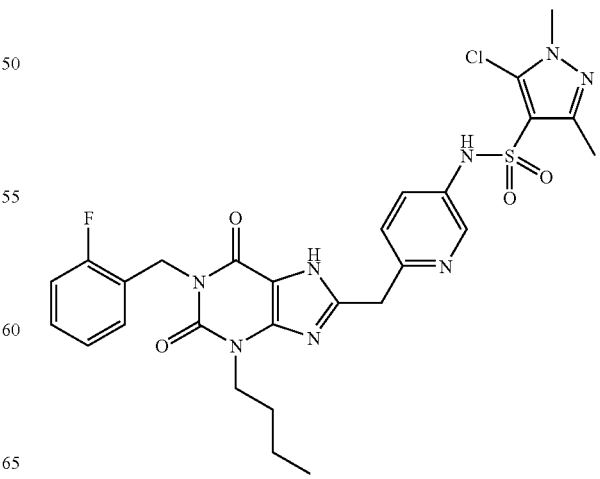

This compound was prepared by the route outlined in schemes 1 and 7.

Step 1: Preparation of 2-(5-nitro-pyridin-2-yl)-malonic acid dibenzyl ester.

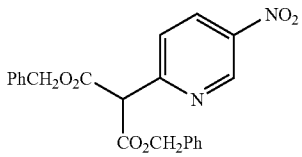

A solution of potassium tert-butoxide in dimethylsulfoxide was treated with dibenzyl malonate. This mixture was stirred at 95° C. for 10 min. At this time, the reaction was treated with a solution of 2-chloro-5-nitropyridine. The resulting mixture was stirred at 95° C. for 1.5 h. At this time, the reaction mixture was poured into ice/water and extracted with ethyl acetate. The organics were washed with a saturated aqueous sodium chloride solution, dried over sodium sulfate, filtered, and concentrated in vacuo. Flash chromatography (Merck Silica gel 60, 230–400 mesh, 20/80 ethyl acetate/hexanes) afforded 2-(5-nitro-pyridin-2-yl)-malonic acid dibenzyl ester (45%) as a bright yellow solid; LRMS for $C_{22}H_{18}N_2O_6$ (M–H)$^+$ at m/z=405.

Step 2: Preparation of 2-(5-amino-pyridin-2-yl)-malonic acid dibenzyl ester.

A solution of 2-(5-nitro-pyridin-2-yl)-malonic acid dibenzyl ester in a mixture of methanol, tetrahydrofuran, and water was treated with ammonium chloride (25 eq.) and zinc dust (>10 micron,10 eq.). The mixture was stirred at 25° C. for 40 min. At this time, the reaction was filtered through celite. The filtrate was concentrated in vacuo. The aqueous residue was extracted with ethyl acetate. The organics were washed with a saturated aqueous sodium chloride solution, dried over sodium sulfate, filtered, and concentrated in vacuo to afford 2-(5-amino-pyridin-2-yl)-malonic acid dibenzyl ester as a yellow viscous oil (89%); LRMS for $C_{22}H_{20}N_2O_4$ (M+H)$^+$ at m/z=377.

Step 3: Preparation of 2-[5-(5-chloro-1,3-dimethyl-1H-pyrazole-4-sulfonylamino)-pyridin-2-yl]-malonic acid dibenzyl ester

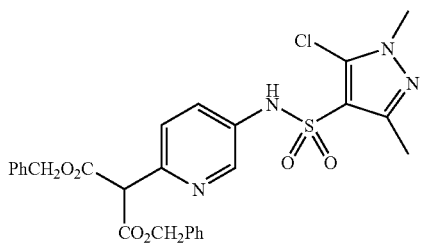

A solution of 2-(5-amino-pyridin-2-yl)-malonic acid dibenzyl ester in pyridine cooled to 0° C. was treated with 5-chloro-1,3-dimethyl-1H-pyrazole-4-sulfonyl chloride. The reaction mixture was allowed to slowly warm to 25° C. and was stirred at 25° C. for 24 h. At this time, the reaction mixture was cooled to 0° C. and acidified to pH=1 with 3.0M aqueous hydrochloric acid solution. The resulting mixture was extracted with ethyl acetate. The organics were washed with a 1.0M aqueous hydrochloric acid solution, water, and a saturated aqueous sodium chloride solution, dried over sodium sulfate, filtered, and concentrated in vacuo. Flash chromatography (Merck Silica gel 60, 230–400 mesh, 65/35 ethyl acetate/hexanes) afforded 2-[5-(5-chloro-1,3-dimethyl-1H-pyrazole-4-sulfonylamino)-pyridin-2-yl]-malonic acid dibenzyl ester (55%) as a colorless solid; LRMS for $C_{27}H_{25}ClN_4O_6S$ (M+H)$^+$ at m/z=569/571.

Step 4: Preparation of [5-(5-chloro-1,3-dimethyl-1H-pyrazole-4-sulfonylamino)-pyridin-2-yl]-acetic acid

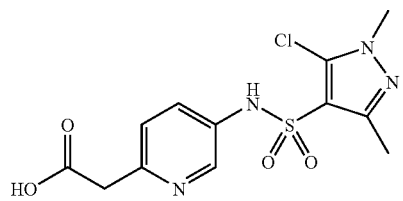

A solution of 2-[5-(5-chloro-1,3-dimethyl-1H-pyrazole-4-sulfonylamino)-pyridin-2-yl]-malonic acid dibenzyl ester in ethyl acetate was treated with 10% palladium on carbon. The mixture was hydrogenolyzed at 25° C. under hydrogen at 1 atmosphere until no starting material remained. At this time, the reaction mixture was filtered through celite. The filtrate was concentrated in vacuo to afford [5-(5-chloro-1,3-dimethyl-1H-pyrazole-4-sulfonylamino)-pyridin-2-yl]-acetic acid (94%) as a colorless solid; LRMS for $C_{12}H_{13}ClN_4O_4S$ (M+H)$^+$ at m/z=345/347.

Step 5: Preparation of N-[6-amino-1-butyl-3-(2-fluoro-benzyl)-2,4-dioxo-1,2,3,4-tetrahydro-pyrimidin-5-yl]-2-[5-(5-chloro-1,3-dimethyl-1H-pyrazole-4-sulfonylamino)-pyridin-2-yl]-acetamide.

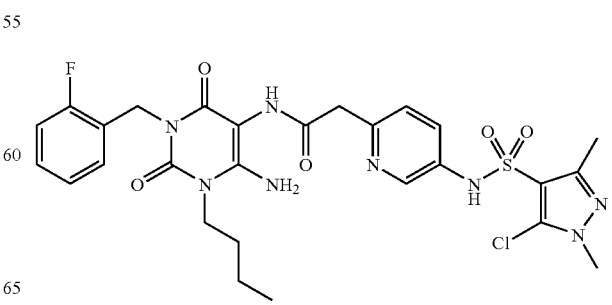

Prepared as for 2-[4-(2-acetylamino-4-methyl-thiazole-5-sulfonylamino)-phenyl]-N-[6-amino-1-cyclopropylmethyl-3-(2-fluoro-benzyl)-2,4-dioxo-1,2,3,4-tetrahydro-pyrimidin-5-yl]-acetamide (example 10, step 1) except using [5-(5-chloro-1,3-dimethyl-1H-pyrazole-4-sulfonylamino)-pyridin-2-yl]-acetic acid and 5,6-diamino-1-butyl-3-(2-fluoro-benzyl)-1H-pyrimidine-2,4-dione. N-[6-amino-1-butyl-3-(2-fluoro-benzyl)-2,4-dioxo-1,2,3,4-tetrahydro-pyrimidin-5-yl]-2-[5-(5-chloro-1,3-dimethyl-1H-pyrazole-4-sulfonylamino)-pyridin-2-yl]-acetamide was used without purification (91%); LRMS for $C_{27}H_{30}ClFN_8O_5S$ (M+H)$^+$ at m/z=633/635.

Step 6: Preparation of 5-chloro-1,3-dimethyl-1H-pyrazole-4-sulfonic acid {6-[3-butyl-1-(2-fluoro-benzyl)-2,6-dioxo-2,3,6,7-tetrahydro-1H-purin-8-ylmethyl]-pyridin-3-yl}-amide.

Prepared as for N-(5-{4-[3-cyclopropylmethyl-1-(2-fluoro-benzyl)-2,6-dioxo-2,3,6,7-tetrahydro-1H-purin-8-ylmethyl]-phenylsulfamoyl}-4-methyl-thiazol-2-yl)-acetamide (example 10, step 2) except using the 5-chloro-1,3-dimethyl-1H-pyrazole-4-sulfonic acid 6-pyridin-3-yl-amide analog. Flash chromatography (Merck Silica gel 60, 230–400 mesh, 5/95 methanol/methylene chloride) afforded 5-chloro-1,3-dimethyl-1H-pyrazole-4-sulfonic acid {6-[3-butyl-1-(2-fluoro-benzyl)-2,6-dioxo-2,3,6,7-tetrahydro-1H-purin-8-ylmethyl]-pyridin-3-yl}-amide (49%) as an off-white solid; FAB-HRMS m/e calculated for $C_{27}H_{28}ClFN_8O_4S$ (M+H)$^+$ 615.1705, found 615.1691.

Example 26

5-Chloro-1,3-dimethyl-1H-pyrazole-4-sulfonic acid {6-[3-cyclobutylmethyl-1-(2-fluoro-benzyl)-2,6-dioxo-2,3,6,7-tetrahydro-1H-purin-8-ylmethyl]-pyridin-3-yl}-amide This compound was prepared by the route shown in scheme 1.

Step 1: Preparation of N-[6-amino-3-(2-fluoro-benzyl)-2,4-dioxo-1,2,3,4-tetrahydro-pyrimidin-5-yl]-2-[5-(5-chloro-1,3-dimethyl-1H-pyrazole-4-sulfonylamino)-pyridin-2-yl]-acetamide

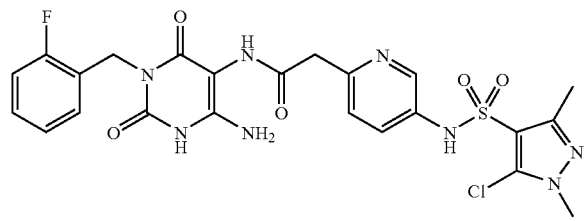

Prepared as for 2-[4-(2-acetylamino-4-methyl-thiazole-5-sulfonylamino)-phenyl]-N-[6-amino-1-cyclopropylmethyl-3-(2-fluoro-benzyl)-2,4-dioxo-1,2,3,4-tetrahydro-pyrimidin-5-yl]-acetamide (example 10, step 1) except that the coupling was performed using 1 [3-(dimethylamino)propyl]-3-ethylcarbodiimide hydrochloride as the coupling reagent and [5-(5-chloro-1,3-dimethyl-1H-pyrazole-4-sulfonylamino)-pyridin-2-yl]-acetic acid and 5,6-diamino-3-(2-fluoro-benzyl)-1H-pyrimidine-2,4-dione were used as the coupling partners. Flash chromatography (Merck Silica gel 60, 230–400 mesh, 10/90 methanol/chloroform) afforded N-[6-amino-3-(2-fluoro-benzyl)-2,4-dioxo-1,2,3,4-tetrahydro-pyrimidin-5-yl]-2-[5-(5-chloro-1,3-dimethyl-1H-pyrazole-4-sulfonylamino)-pyridin-2-yl]-acetamide (42%) as an off white solid; LRMS for $C_{29}H_{29}ClFN_7O_4S$ (M+H)$^+$ at m/z=577/579.

Step 2: Preparation of N-[6-amino-1-cyclobutylmethyl-3-(2-fluoro-benzyl)-2,4-dioxo-1,2,3,4-tetrahydro-pyrimidin-5-yl]-2-[5-(5-chloro-1,3-dimethyl-1H-pyrazole-4-sulfonylamino)-pyridin-2-yl]-acetamide.

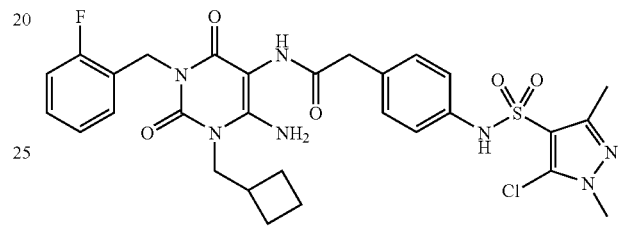

A solution of N-[6-amino-3-(2-fluoro-benzyl)-2,4-dioxo-1,2,3,4-tetrahydro-pyrimidin-5-yl]-2-[5-(5-chloro-1,3-dimethyl-1H-pyrazole-4-sulfonylamino)-pyridin-2-yl]-acetamide in N,N-dimethylformamide was treated with potassium carbonate (4.0 eq.) and (bromomethyl)cyclobutane (2.0 eq.). The reaction mixture was heated to 40° C. for 16 h. At this time, the N,N,-dimethylformamide was removed in vacuo. The residue was triturated with chloroform and then methanol to remove impurities. Flash chromatography (Merck Silica gel 60, 230–400 mesh, 10/90 methanol/chloroform) afforded N-[6-amino-1-cyclobutylmethyl-3-(2-fluoro-benzyl)-2,4-dioxo-1,2,3,4-tetrahydro-pyrimidin-5-yl]-2-[5-(5-chloro-1,3-dimethyl-1H-pyrazole-4-sulfonylamino)-pyridin-2-yl]-acetamide (15%) as a light brown solid; LRMS for $C_{29}H_{31}ClFN_7O_5S$ (M+H)$^+$ at m/z=645.

Step 3: Preparation of 5-chloro-1,3-dimethyl-1H-pyrazole-4-sulfonic acid {6-[3-cyclobutylmethyl-1-(2-fluoro-benzyl)-2,6-dioxo-2,3,6,7-tetrahydro-1H-purin-8-ylmethyl]-pyridin-3-yl}-amide.

Prepared as for N-(5-{4-[3-cyclopropylmethyl-1-(2-fluoro-benzyl)-2,6-dioxo-2,3,6,7-tetrahydro-1H-purin-8-ylmethyl]-phenylsulfamoyl}-4-methyl-thiazol-2-yl)-acetanide (example 10, step 2) except using the 5-chloro-1,3-dimethyl-1H-pyrazole-4-sulfonic acid 6-pyridin-3-yl-amide analog. Flash chromatography (Merck Silica gel 60, 230–400 mesh, 10/90 methanol/chloroform) afforded 5-chloro-1,3-dimethyl-1H-pyrazole-4-sulfonic acid {6-[3-cyclobutylmethyl-1-(2-fluoro-benzyl)-2,6-dioxo-2,3,6,7-tetrahydro-1H-purin-8-ylmethyl]-pyridin-3-yl}-amide (62%) as an off-white solid; EI-HRMS m/e calculated for $C_{28}H_{28}ClFN_8O_4S$ (M+H)$^+$ 627.1700, found 627.1707.

Example 27

1,3-Dimethyl-1H-pyrazole-4-sulfonic acid {4-[3-cyclopropylmethyl-1-(2-fluoro-benzyl)-2,6-dioxo-2,3,6,7-tetrahydro-1H-purin-8-ylmethyl]-phenyl}-methyl-amide

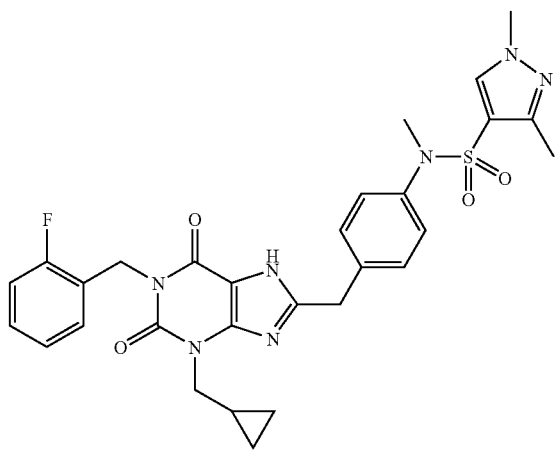

A solution of 5-chloro-1,3-dimethyl-1H-pyrazole-4-sulfonic acid {4-[3-cyclopropylmethyl-1-(2-fluoro-benzyl)-2,6-dioxo-2,3,6,7-tetrahydro-1H-purin-8-ylmethyl]-phenyl}-methyl-amide (prepared as described in Example 18, 20 mg, 0.032 mmol) in methanol (20 mL) at 25° C. was treated with 10% Pd/C (100 mg). The reaction mixture was submitted to hydrogenation conditions in a Parr bomb at 48 psi for 2 d. At this time, the reaction mixture was filtered through a pad of celite and washed with 90/10 methylene chloride/methanol solution (75 mL). The filtrated was concentrated in vacuo. The resulting residue was purified by HPLC (20–60% acetonitrile/water) to afford 1,3-dimethyl-1H-pyrazole-4-sulfonic acid {4-[3-cyclopropylmethyl-1-(2-fluoro-benzyl)-2,6-dioxo-2,3,6,7-tetrahydro-1H-purin-8-ylmethyl]-phenyl}-methyl-amide (7.0 mg, 37%) as white solid; (ES)$^+$-HRMS m/e calculated for $C_{29}H_{30}FN_7O_4S$ (M+Na)$^+$ 614.1956, found 614.1955.

Example 28

4-[3-Butyl-1-(2-fluoro-benzyl)-2,6-dioxo-2,3,6,7-tetrahydro-1H-purin-8-ylmethyl]-N-pyridin-2-yl-benzenesulfonamide

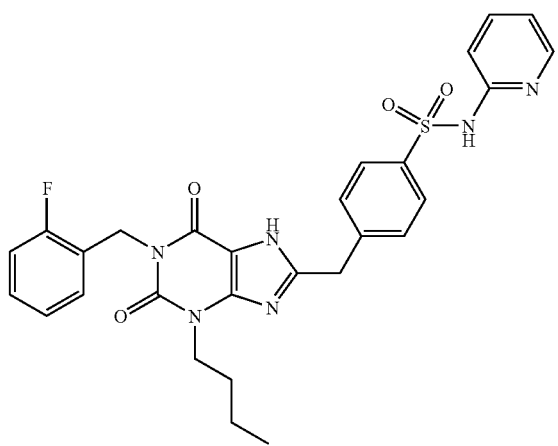

This compound was prepared according to the general procedures outlined in schemes 2 and 6.

Step 1: Preparation of [4-(pyridin-2-ylsulfamoyl)-phenyl]-acetic acid ethyl ester.

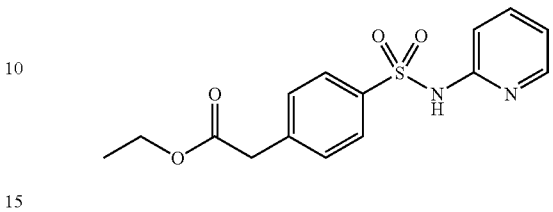

A stirred solution of 2-aminopyridine (282 mg, 3.0 mmol) in dry pyridine (5.0 mL) was treated with (4-chlorosulfonyl-phenyl)-acetic acid ethyl ester (prepared according to the procedure of Kawashima et. al, as described in *Chem. Pharm. Bull.* 1995, 43(7), 1132) dropwise at 0–5° C. under argon. Upon completion of addition, the reaction was slowly warmed to 25° C. The reaction was stirred at 25° C. until no starting materials remained. At this time, the reaction was cooled to 0° C. and was acidified to pH=5 with a 1.0M aqueous hydrochloric acid solution. The reaction mixture was poured into water and was extracted with ethyl acetate. The combined organic extracts were washed with water and a saturated aqueous sodium chloride solution, dried over magnesium sulfate, filtered, and concentrated in vacuo. Flash chromatography (Merck Silica gel 60, 230–400 mesh, 3/97 methanol/methylene chloride) afforded [4-(pyridin-2-ylsulfamoyl)-phenyl]-acetic acid ethyl ester (0.26 g, 27%) as a colorless solid; $^1$H NMR (CDCl$_3$, 300 MHz) $\delta_H$ 13.67 (broad s, 1H), 8.30 (dd, J=5.9, 1.1 Hz, 1H), 7.86 (d, J=8.4 Hz, 2H), 7.65 (tt, J=8.1, 1.7 Hz, 1H), 7.50–7.30 (m, 3H), 6.77 (t, J=6.3 Hz, 1H), 4.12 (q, J=7.0 Hz, 2H), 3.63 (s, 2H), 1.22 (t, J=7.0 Hz, 3H); LRMS for $C_{15}H_{16}N_2O_4S$ (M+H)$^+$ at m/z=321.

Step 2: Preparation of [4-(pyridin-2-ylsulfamoyl)-phenyl]-acetic acid.

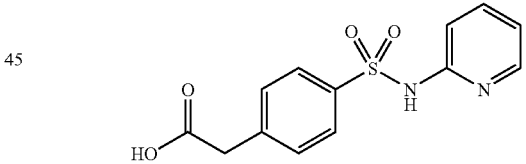

A solution of [4-(pyridin-2-ylsulfamoyl)-phenyl]-acetic acid ethyl ester (0.26 g, 0.813 mmol) in absolute ethanol (10 mL) was treated with a 1.0M ethanolic potassium hydroxide solution (2.0 mL, 2.0 mmol). The reaction mixture was heated to reflux under argon for 3.5 h. The reaction mixture was then concentrated in vacuo. The residue was dissolved in water and filtered through celite. The filtrate was acidified to pH=4.5 with a 1.0M aqueous hydrochloric acid solution. The resulting precipitate was collected by filtration, washed with water, and dried in vacuo to afford [4-(pyridin-2-ylsulfamoyl)-phenyl]-acetic acid (155 mg, 65%) as an off white solid; $^1$H NMR (DMSO-d$_6$, 300 MHz) $\delta_H$ 12.26 (broad s, 1H), 7.96 (d, J=4.4 Hz, 1H), 7.77 (d, J=7.7 Hz, 2H), 7.80 (t, J=7.5 Hz, 1H), 7.37 (d, J=7.7 Hz, 2H), 7.13 (d, J=8.8 Hz, 1H), 6.82 (broad s, 1H), 3.62 (s, 2H); LRMS for $C_{13}H_{12}N_2O_4S$ (M+H)$^+$ at m/z=293.

Step 3: Preparation of N-[1-Butyl-3-(2-fluoro-benzyl)-2,4-dioxo-1,2,3,4-tetrahydro-pyrimidin-5-yl]-2-[4-(pyridin-2-ylsulfamoyl)-phenyl]-acetamide.

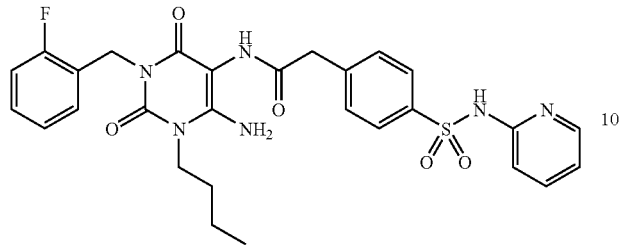

A solution of 5,6-diamino-1-butyl-3-(2-fluoro-benzyl)-1H-pyrimidine-2,4-dione (30.6 mg, 0.1 mmol) and [4-(pyridin-2-ylsulfamoyl)-phenyl]-acetic acid (29.2 mg, 0.1 mmol) in dry N,N-dimethylformamide (1 mL) was treated with N,N-diisopropylethylamine (61 mL, 0.35 mmol) and O-benzotriazol-1-yl-N,N,N',N'-tetramethyluronium tetrafluoroborate (37.9 mg, 0.1 mmol). The mixture was stirred at 25° C. for 16 h. The reaction mixture was diluted with water and acidified to pH=5.0 with a 0.01M aqueous hydrochloric acid solution. The reaction mixture was extracted with ethyl acetate. The combined organic extracts were washed with water and a saturated aqueous sodium chloride solution, dried over magnesium sulfate, filtered, and concentrated in vacuo to afford N-[1-butyl-3-(2-fluoro-benzyl)-2,4-dioxo-1,2,3,4-tetrahydro-pyrimidin-5-yl]-2-[4-(pyridin-2-ylsulfamoyl)-phenyl]-acetamide (86%); $^1$H NMR(CDCl$_3$, 300 MHz) $\delta_H$ 8.20–6.65 (m, 13H), 5.21 (broad s, 2H), 5.02 (s, 2H), 3.79 (t, J=7 Hz, 2H), 3.60 (s, 2H), 1.65–1.20 (m, 4H), 0.85 (t, J=7 Hz, 3H); LRMS for $C_{28}H_{29}FN_6O_5S$ (M+H)$^+$ at m/z=581.

Step 4: Preparation of 4-[3-butyl-1-(2-fluoro-benzyl)-2,6-dioxo-2,3,6,7-tetrahydro-1H-purin-8-ylmethyl]-N-pyridin-2-yl-benzenesulfonamide.

A solution of crude N-[6-amino-1-butyl-3-(2-fluoro-benzyl)-2,4-dioxo-1,2,3,4-tetrahydro-pyrimidin-5-yl]-2-[4-(pyridin-2-ylsulfamoyl)-phenyl]-acetamide (50 mg, 0.86 mmol) in methanol (5 mL) was treated with a 10% w/v aqueous sodium hydroxide solution (0.1 mL, 0.25 mmol). The resulting solution was heated to reflux for until all of the starting material had been consumed. At this time, the reaction mixture was concentrated in vacuo. Flash chromatography (Merck Silica gel 60, 230–400 mesh, 5/95 methanol/methylene chloride) followed by trituration with cold methanol afforded 4-[3-butyl-1-(2-fluoro-benzyl)-2,6-dioxo-2,3,6,7-tetrahydro-1H-purin-8-ylmethyl]-N-pyridin-2-yl-benzenesulfonamide (14.7 mg, 26% from [4-(pyridin-2-ylsulfamoyl)-phenyl]-acetic acid) as a colorless solid; $^1$H NMR(DMSO-d$_6$, 300 MHz) $\delta_H$ 13.50 (broad s, 1H), 7.90 (broad s, 1H), 7.74 (d, J=8.1 Hz, 2H), 7.63 (t, J=7.3 Hz, 1H), 7.37 (d, J=7.7 Hz, 2H), 7.30–6.95 (m, 5H), 6.77 (broad s, 1H), 5.02 (s, 2H), 4.06 (s, 2H), 3.87 (t, J=7.1 Hz, 2H), 1.54 (t, J=7.0 Hz, 2H), 1.17 (q, J=7.5 Hz, 2H), 0.77 (t, J=7.3 Hz, 3H); FAB-HRMS m/e calculated for $C_{28}H_{27}FN_6O_4S$ (M+H)$^+$ 563.1877, found 563.1860.

The compounds cited in examples 29 to 33 were obtained in an analogous manner to that described in example 28.

Example 29

4-[3-Butyl-1-(2-fluoro-benzyl)-2,6-dioxo-2,3,6,7-tetrahydro-1H-purin-8-ylmethyl]-N-pyridin-4-yl-benzenesulfonamide

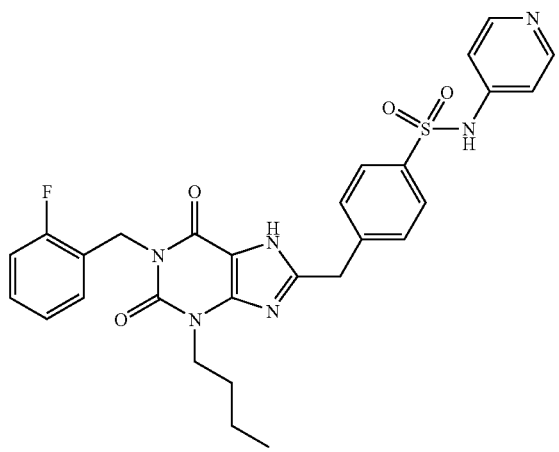

Prepared from 5,6-diamino-1-butyl-3-(2-fluoro-benzyl)-1H-pyrimidine-2,4-dione (30.6 mg, 0.1 mmol) and [4-(pyridin-4-ylsulfamoyl)-phenyl]-acetic acid. 4-[3-Butyl-1-(2-fluoro-benzyl)-2,6-dioxo-2,3,6,7-tetrahydro-1H-purin-8-ylmethyl]-N-pyridin-4-yl-benzenesulfonamide was obtained as a colorless solid; $^1$H NMR (DMSO-d$_6$, 300 MHz) $\delta_H$ 13.50 (s, 1H), 12.65 (broad s, 1H), 8.00–7.80 (m, 2H), 7.75–7.60 (m, 2H), 7.55–7.35 (m, 2H), 7.30–6.80 (m, 6H), 5.08 (s, 2H), 4.11 (s, 2H), 3.93 (t, J=7.3 Hz, 2H), 1.70–1.50 (m, 2H), 1.35–1.15 (m, 2H), 0.83 (t, J=7.1 Hz, 3H); FAB-HRMS m/e calculated for $C_{28}H_{27}FN_6O_4S$ (M+H)$^+$ 563.1877, found 563.1858.

Example 30

4-[3-Butyl-1-(2-fluoro-benzyl)-2,6-dioxo-2,3,6,7-tetrahydro-1H-purin-8-ylmethyl]-N-pyridin-3-yl-benzenesulfonamide

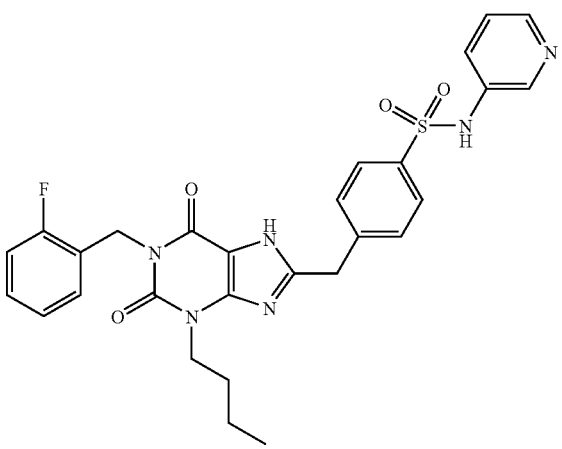

Prepared from 5,6-diamino-1-butyl-3-(2-fluoro-benzyl)-1H-pyrimidine-2,4-dione (30.6 mg, 0.1 mmol) and [4-(pyridin-3-ylsulfamoyl)-phenyl]-acetic acid. 4-[3-Butyl-1-(2-fluoro-benzyl)-2,6-dioxo-2,3,6,7-tetrahydro-1H-purin-8-ylmethyl]-N-pyridin-3-yl-benzenesulfonamide was obtained as a colorless solid; $^1$H NMR (DMSO-d$_6$, 300 MHz) $\delta_H$ 13.50 (s, 1H), 10.54 (s, 1H), 8.23 (d, J=14.3 Hz, 2H), 7.71 (d, J=8.1 Hz, 2H), 7.55–7.40 (m, 3H), 7.35–6.95 (m, 5H), 5.08 (s, 2H), 4.13 (s, 2H), 3.92 (t, J=7.3 Hz, 2H), 1.59 (t, J=7.1 Hz, 2H), 1.23 (q, J=7.3 Hz, 2H), 0.83 (t, J=7.5 Hz, 3H); FAB-HRMS m/e calculated for $C_{28}H_{27}FN_6O_4S$ (M+H)$^+$ 563.1877, found 563.1860.

Example 31

4-[3-Butyl-1-(2-fluoro-benzyl)-2,6-dioxo-2,3,6,7-tetrahydro-1H-purin-8-ylmethyl]-N-pyrimidin-2-yl-benzenesulfonamide

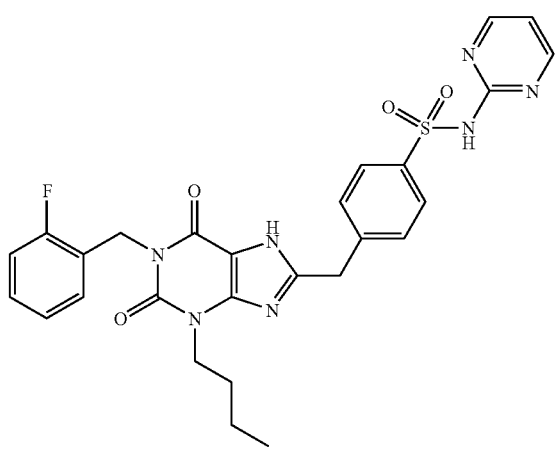

Prepared from 5,6-diamino-1-butyl-3-(2-fluoro-benzyl)-1H-pyrimidine-2,4-dione (30.6 mg, 0.1 mmol) and [4-(pyrimidine-2-sulfonylamino)-phenyl]-acetic acid. 4-[3-Butyl-1-(2-fluoro-benzyl)-2,6-dioxo-2,3,6,7-tetrahydro-1H-purin-8-ylmethyl]-N-pyrimidin-2-yl-benzenesulfonamide was obtained as a colorless solid; $^1$H NMR (DMSO-d$_6$, 300 MHz) $\delta_H$ 13.64 (s, 1H), 11.85 (broad s, 1H), 8.57 (d, J=5.1 Hz, 2H), 8.02 (d, J=8.4 Hz, 2H), 7.57 (d, J=8.4 Hz, 2H), 7.40–7.00 (m, 5H), 5.18 (s, 2H), 4.25 (s, 2H), 4.03 (t, J=7.1 Hz, 2H), 1.75–1.60 (m, 2H), 1.40–1.25 (m, 2H), 0.93 (t, J=7.3 Hz, 3H); FAB-HRMS m/e calculated for $C_{27}H_{26}FN_7O_4S$ (M+H)$^+$ 564.1829, found 564.1835.

Example 32

4-[3-Butyl-1-(2-fluoro-benzyl)-2,6-dioxo-2,3,6,7-tetrahydro-1H-purin-8-ylmethyl]-N-(1,3,5-trimethyl-1H-pyrazol-4-yl)-benzenesulfonamide

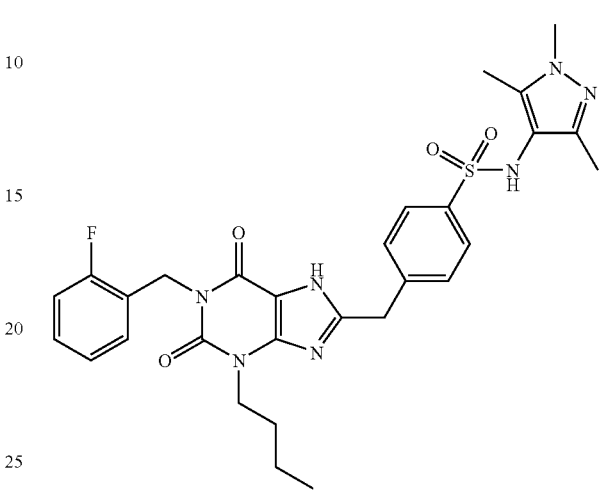

Prepared from 5,6-diamino-1-butyl-3-(2-fluoro-benzyl)-1H-pyrimidine-2,4-dione (30.6 mg, 0.1 mmol) and [4-(1,3,5-trimethyl-1H-pyrazol-4-ylsulfamoyl)-phenyl]-acetic acid. 4-[3-Butyl-1-(2-fluoro-benzyl)-2,6-dioxo-2,3,6,7-tetrahydro-1H-purin-8-ylmethyl]-N-(1,3,5-trimethyl-1H-pyrazol-4-yl)-benzenesulfonamide was obtained as a colorless solid; $^1$H NMR (DMSO-d$_6$, 300 MHz) $\delta_H$ 13.48 (s, 1H), 8.94 (s, 1H), 7.49 (d, J=8.4 Hz, 2H), 7.38 (d, J=7.7 Hz, 2H), 7.30–6.90 (m, 4H), 5.03 (s, 2H), 4.10 (s, 2H), 3.88 (t, J=7.1 Hz, 2H), 3.45 (s, 3H), 1.71 (s, 3H), 1.60–1.45 (m, 2H), 1.42 (s, 3H), 1.25–1.10 (m, 2H), 0.79 (t, J=7.5 Hz, 3H); FAB-HRMS m/e calculated for $C_{29}H_{32}FN_7O_4S$ (M+H)$^+$ 594.2299, found 594.2281.

Example 33

4-[3-Butyl-1-(2-fluoro-benzyl)-2,6-dioxo-2,3,6,7-tetrahydro-1H-purin-8-ylmethyl]-N-thiazol-2-yl-benzenesulfonamide

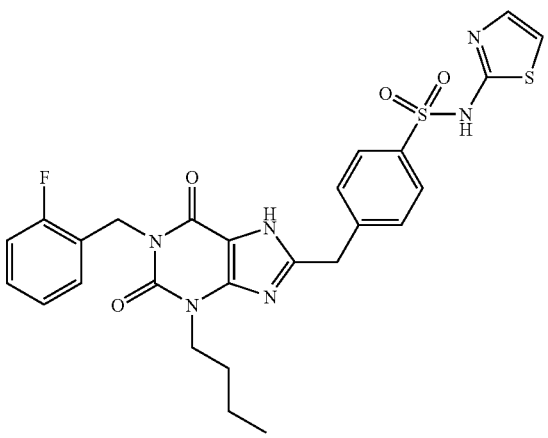

Prepared from 5,6-diamnino-1-butyl-3-(2-fluoro-benzyl)-1H-pyrimidine-2,4-dione (30.6 mg, 0.1 mmol) and [4-(thiazol-2-ylsulfamoyl)-phenyl]-acetic acid. 4-[3-Butyl-1-(2-fluoro-benzyl)-2,6-dioxo-2,3,6,7-tetrahydro-1H-purin-8-ylmethyl]-N-thiazol-2-yl-benzenesulfonamide was obtained as a colorless solid; $^1$H NMR (DMSO-d$_{6, 300}$ MHz) $\delta_H$ 13.53 (s, 1H), 12.70 (s, 1H), 7.73 (d, J=8.1 Hz, 2H), 7.43 (d, J=8.1 Hz, 2H), 7.35–6.95 (m, 5H), 6.80 (d, J=4.8 Hz, 1H), 5.08 (s, 2H), 4.13 (s, 2H), 3.93 (t, J=7.1 Hz, 2H), 1.70–1.50 (m, 2H), 1.30–1.15 (m, 2H), 0.84 (t, J=7.3 Hz, 3H); FAB-HRMS m/e calculated for $C_{26}H_{25}FN_6O_4S_2$ (M+H)$^+$ 569.144 1, found 569.1431.

Example 34

5-Chloro-1,3-dimethyl-1H-pyrazole-4-sulfonic acid {4-[3-butyl-1-(2-fluoro-benzyl)-2,6-dioxo-2,3,6,7-tetrahydro-1H-purin-8-ylmethyl]-phenyl}-amide

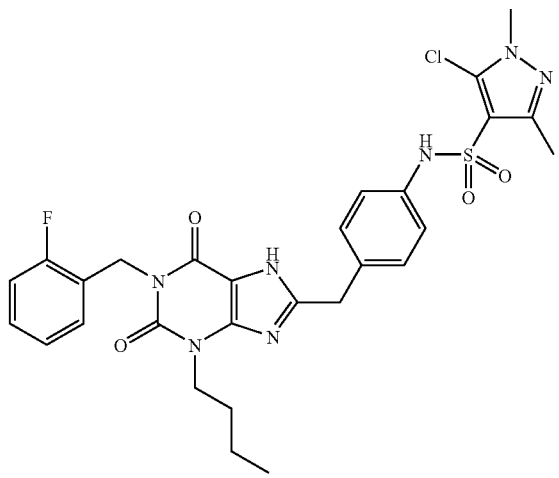

This compound was prepared by the routes outlined in schemes 3 and 4.

Step 1: Preparation of 1-butyl-6-chloro-1H-pyrimidine-2,4-dione.

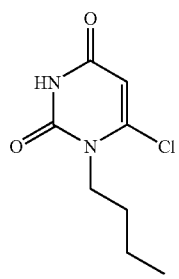

This compound was prepared by the method of Ishikawa et al. as described in *Heterocycles* 1990, 31(9), 1641.

4-Chloro-uracil (Lancaster) (23.36 g, 0.16 mol) was dissolved in dimethyl sulfoxide (100 mL) and treated with potassium carbonate (11.2 g, 0.08 mol) and 1-iodobutane (Aldrich) (52.8 mL, 0.48 mol). After stirring at 23° C. for 18 h, the reaction was then mixed with water and extracted with ethyl acetate (3×). The combined ethyl acetate layers were then washed with diluted aqueous sodium chloride solution and brine, dried (sodium sulfate) and concentrated to dryness to afford the crude product as an off-white solid (27.34 g, 85%). $^1$H NMR (CDCl$_3$, 200 MHz) $\delta_H$ 0.95 (t, 3H), 1.40 (m, 2H), 1.58 (m, 2H), 4.02 (t, 2H), 5.80 (s, 1H), 8.93 (br s, 1H).

Step 2: Preparation of 1-butyl-6-chloro-3-(2-fluorobenzyl)-1H-pyrimidine-2,4-dione.

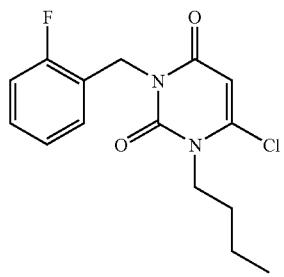

The crude product from step 1 (3.0 g, 14.8 mmol) was dissolved in N,N-dimethylformamide (30 mL) and treated with potassium carbonate (4.08 g, 29.6 mmol) and 2-fluorobenzyl bromide (Aldrich) (1.8 ml, 14.8 mmol). The reaction was stirred at 23° C. for 2 hours and then at 48° C. for 3 hours. The reaction was mixed with diluted brine and extracted with ethyl acetate (3×). The combined ethyl acetate extracts were then washed with diluted aqueous sodium chloride solution and brine, dried (sodium sulfate) and concentrated to dryness to afford 1-butyl-6-chloro-3-(2-fluorobenzyl)-1H-pyrimidine-2,4-dione as a yellow oil (4.07 g, 89%). $^1$H NMR (CDCl$_3$, 200 MHz) $\delta_H$ 0.96 (t, 3H), 1.25–1.48 (m, 2H), 1.58–1.76 (m, 2H), 4.03 (t, 2H), 5.20 (s, 2H), 5.97 (s, 1H), 6.97–7.10 (m, 2H), 7.17–7.30 (m, 2H).

Step 3: Preparation of 1-butyl-3-(2-fluorobenzyl)-6-[2-(4-nitro-phenyl)-ethylamino]-1H-pyrimidine-2,4-dione.

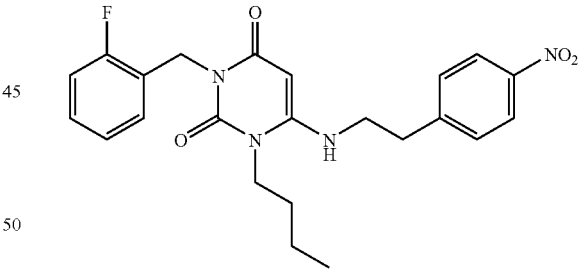

A mixture of 2-(4-nitro-phenyl)-ethylamine hydrochloride salt (Fluka) (7.85 g, 38.7 mmol), 1-butyl-6-chloro-3-(2-fluorobenzyl)-1H-pyrimidine-2,4-dione (8.0 g, 25.8 mmol) and triethylamine (10.7 mL, 77 mmol) in N-methylpyrrolidin-2-one (200 mL) was stirred at 75° C. for 16 hours. The reaction was then mixed with water and extracted with ethyl acetate (3×). The combined ethyl acetate layers were dried (magnesium sulfate) and concentrated. Column chromatography afforded 1-butyl-3-(2-fluorobenzyl)-6-[2-(4-nitro-phenyl)-ethylamino]-1H-pyrimidine-2,4-dione (4.7 g, 41%) as a solid. $^1$H NMR (CDCl$_3$, 200 MHz) $\delta_H$ 0.84 (t, 3H), 1.11–1.50 (m, 4H), 3.10 (t, 2H), 3.48 (m, 2H), 3.70 (t, 2H), 4.36 (t, 1H), 4.94 (t, 1H), 5.20 (s, 2H), 6.95–7.10 (m, 2H), 7.17–7.30 (m, 2H), 7.39 (d, 2H), 8.20 (d, 2H).

Step 4: Preparation of 3-butyl-1-(2-fluorobenzyl)-8-(4-nitro-benzyl)-3,7-dihydro-purine-2,6-dione.

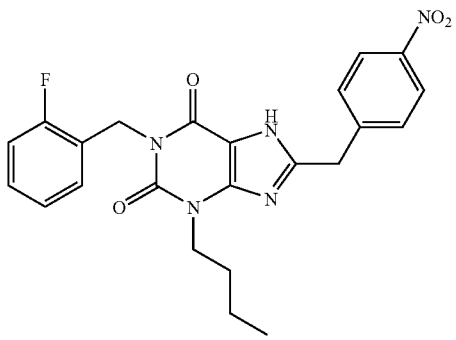

1-Butyl-3-(2-fluorobenzyl)-6-[2-(4-nitro-phenyl)-ethylamino]-1H-pyrimidine-2,4-dione (2.3 g, 5.2 mmol) was dissolved in ethanol (20 mL) and treated with isoamyl nitrite (Aldrich) (3.6 mL, 26 mmol). Concentrated aqueous hydrochloric acid (1 mL) was added to the reaction mixture. The reaction was stirred at 23° C. for 40 minutes. The ethanol was removed under reduced pressure and the residue washed with diethyl ether. The solid residue was then dissolved in n-butanol (15 mL), and the mixture refluxed for 30 minutes. After cooling to room temperature 1-butyl-3-(2-fluorobenzyl)-6-[2-(4-nitro-phenyl)-ethylamino]-1H-pyrimidine-2,4-dione separated as pale yellow crystals which were collected by filtration (1.91 g, 81%). LCMS, m/z(M+H)=452.24.

Step 5: Preparation of 8-(4-amino-benzyl)-3-butyl-1-(2-fluorobenzyl)-3,7-dihydro-purine-2,6-dione.

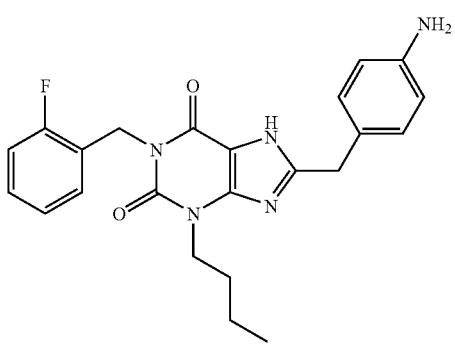

1-Butyl-3-(2-fluorobenzyl)-6-[2-(4-nitro-phenyl)-ethylamino]-1H-pyrimidine-2,4-dione (2.0 g, 4.46 mmol) was dissolved in methanol (100 mL) and treated with zinc dust (<10 μm, Aldrich; 2.91 g) followed by the addition of a solution of ammonium chloride (5.96 g, 112 mmol) in water (50 mL). The reaction mixture was stirred at room temperature for 3 h. The reaction mixture was then filtered through a pad of celite. The filtrate was concentrated to remove methanol and the residual aqueous solution was extracted with ethyl acetate (3×). The combined organic extracts were washed with brine, dried (sodium sulfate) and concentrated in vacuo to afford 8-(4-amino-benzyl)-3-butyl-1-(2-fluorobenzyl)-3,7-dihydro-purine-2,6-dione as a pale yellow solid (1.64 g, 87%). LCMS, m/z(M+H)=422.18.

Step 6: Preparation of 5-chloro-1,3-dimethyl-1H-pyrazole-4-sulfonic acid {4-[3-butyl-1-(2-fluoro-benzyl)-2,6-dioxo-2,3,6,7-tetrahydro-1H-purin-8-ylmethyl]-phenyl}-amide.

8-(4-Amino-benzyl)-3-butyl-1-(2-fluoro-benzyl)-3,7-dihydro-purine-2,6-dione (20 mg, 0.047 mmol) was dissolved in pyridine (0.5 ml) and treated with 5-chloro-1,3-dimethyl-1H-pyrazole-4-sulfonyl chloride (Maybridge, 16 mg, 0.07 mmol). The reaction was stirred at 23° C. for 3 h. The solvent was removed and the residue was purified by reverse phase HPLC. LCMS, m/z (M+H)=615.2.

The compounds cited in examples 35 to 93 were obtained in an analogous manner to that described in example 34.

Example 35

Propane-2-sulfonic acid {4-[3-butyl-1-(2-fluoro-benzyl)-2,6-dioxo-2,3,6,7-tetrahydro-1H-purin-8-ylmethyl]-phenyl}-amide

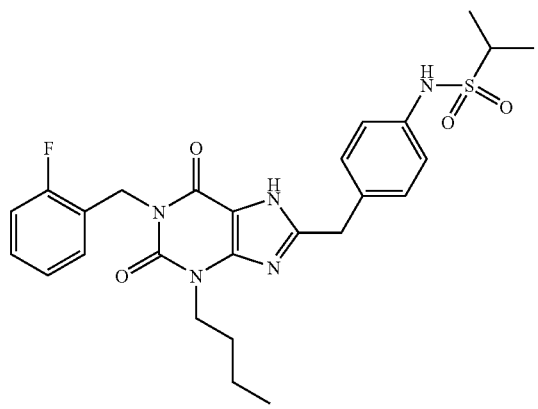

Prepared from 8-(4-amino-benzyl)-3-butyl-1-(2-fluoro-benzyl)-3,7-dihydro-purine-2,6-dione and propane-2-sulfonyl chloride. Purity (ELSD, based on MW=527.6)=84%.

Example 36

Ethanesulfonic acid {4-[3-butyl-1-(2-fluoro-benzyl)-2,6-dioxo-2,3,6,7-tetrahydro-1H-purin-8-ylmethyl]-phenyl}-amide

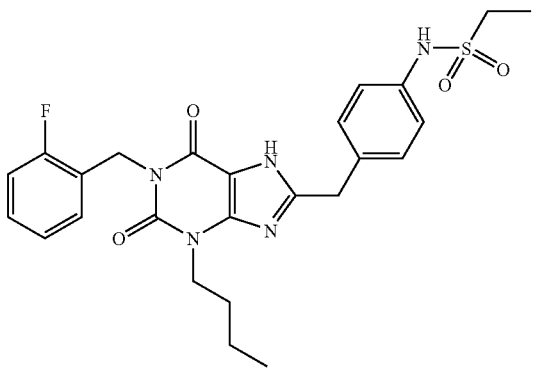

Prepared from 8-(4-amino-benzyl)-3-butyl-1-(2-fluoro-benzyl)-3,7-dihydro-purine-2,6-dione and methanesulfonic chloride. Purity (ELSD, based on MW=513.6)=91%.

Example 37

N-{4-[3-Butyl-1-(2-fluoro-benzyl)-2,6-dioxo-2,3,6,7-tetrahydro-1H-purin-8-ylmethyl]-phenyl}-C-phenyl-methanesulfonamide

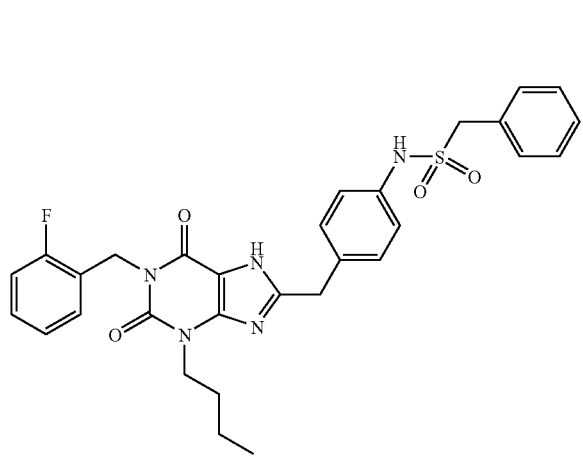

Prepared from 8-(4-amino-benzyl)-3-butyl-1-(2-fluoro-benzyl)-3,7-dihydro-purine-2,6-dione and benzylsulfonyl chloride. Purity (ELSD, based on MW=575.7)=80%.

Example 38

2-Phenyl-ethenesulfonic acid {4-[3-butyl-1-(2-fluoro-benzyl)-2,6-dioxo-2,3,6,7-tetrahydro-1H-purin-8-ylmethyl]-phenyl}-amide

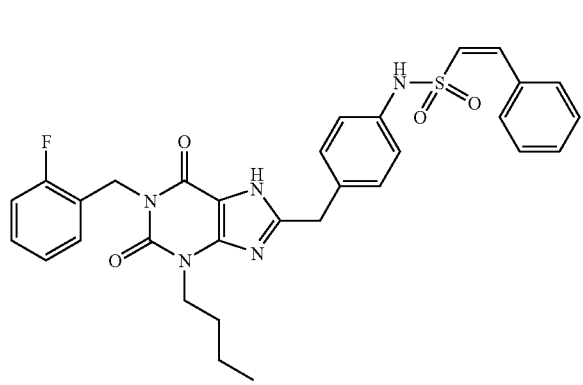

Prepared from 8-(4-amino-benzyl)-3-butyl-1-(2-fluoro-benzyl)-3,7-dihydro-purine-2,6-dione and 2-phenyl-ethenesulfonyl chloride. Purity (ELSD, based on MW=587.7)=97%.

Example 39

N-{4-[3-Butyl-1-(2-fluoro-benzyl)-2,6-dioxo-2,3,6,7-tetrahydro-1H-purin-8-ylmethyl]-phenyl}-benzenesulfonamide

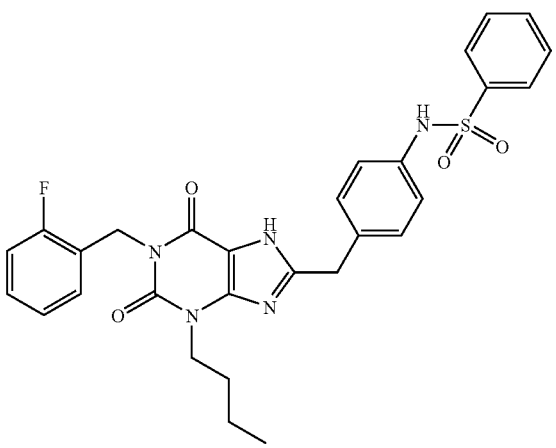

Prepared from 8-(4-amino-benzyl)-3-butyl-1-(2-fluoro-benzyl)-3,7-dihydro-purine-2,6-dione and -benzenesulfonyl chloride. Purity (ELSD, based on MW=561.6)=95%.

Example 40

N-{4-[3-Butyl-1-(2-fluoro-benzyl)-2,6-dioxo-2,3,6,7-tetrahydro-1H-purin-8-ylmethyl]-phenyl}-2-fluoro-benzenesulfonamide

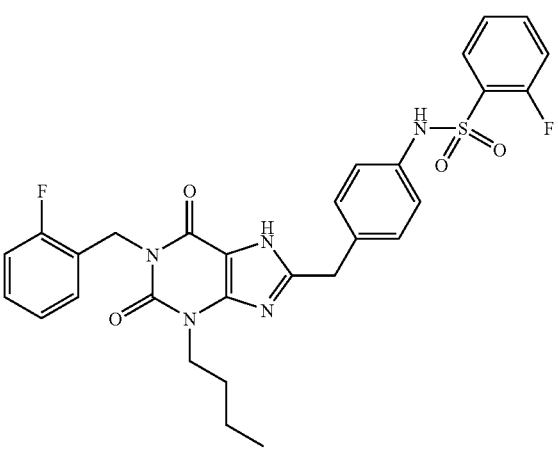

Prepared from 8-(4-amino-benzyl)-3-butyl-1-(2-fluoro-benzyl)-3,7-dihydro-purine-2,6-dione and 2-fluoro-benzenesulfonyl chloride. Purity (ELSD, based on MW=579.6)=80%.

Example 41

N-{4-[3-Butyl-1-(2-fluoro-benzyl)-2,6-dioxo-2,3,6,7-tetrahydro-1H-purin-8-ylmethyl]-phenyl}-2-trifluoromethyl-benzenesulfonamide

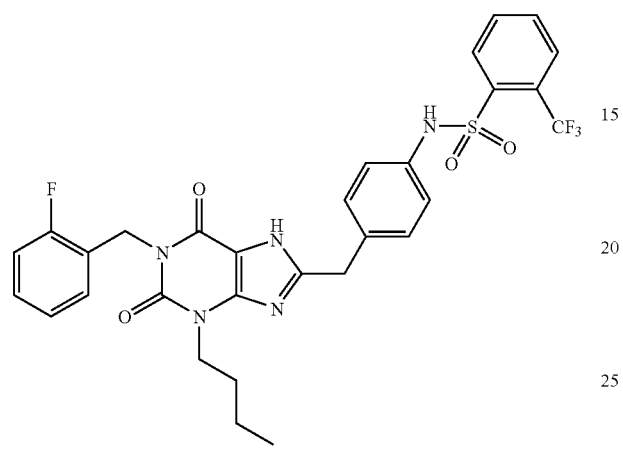

Prepared from 8-(4-amino-benzyl)-3-butyl-1-(2-fluoro-benzyl)-3,7-dihydro-purine-2,6-dione and 2-(trifluoromethyl)-benzenesulfonyl chloride. Purity (ELSD, based on MW=629.6)=90%.

Example 42

N-{4-[3-Butyl-1-(2-fluoro-benzyl)-2,6-dioxo-2,3,6,7-tetrahydro-1H-purin-8-ylmethyl]-phenyl}-2-chloro-benzenesulfonamide

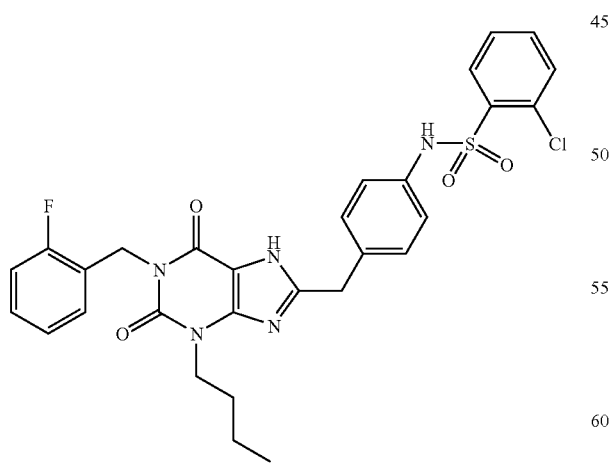

Prepared from 8-(4-amino-benzyl)-3-butyl-1-(2-fluoro-benzyl)-3,7-dihydro-purine-2,6-dione and 2-chloro-benzenesulfonyl chloride. Purity (ELSD, based on MW=596.1)=70%.

Example 43

N-{4-[3-Butyl-1-(2-fluoro-benzyl)-2,6-dioxo-2,3,6,7-tetrahydro-1H-purin-8-ylmethyl]-phenyl}-2-methyl-benzenesulfonamide

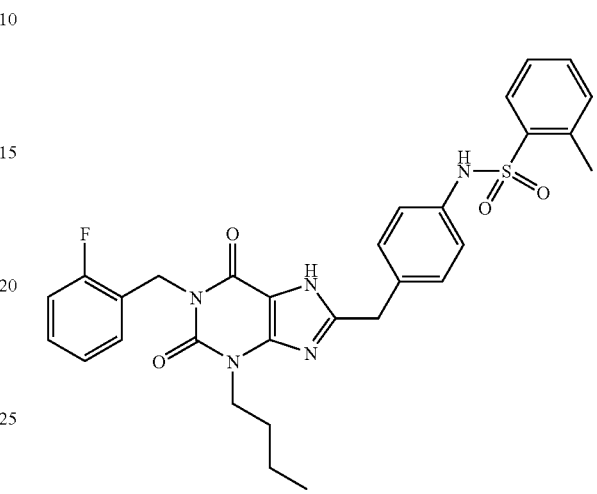

Prepared from 8-(4-amino-benzyl)-3-butyl-1-(2-fluoro-benzyl)-3,7-dihydro-purine-2,6-dione and 2-methyl-benzenesulfonyl chloride. Purity (ELSD, based on MW=575.7)=82%.

Example 44

N-{4-[3-Butyl-1-(2-fluoro-benzyl)-2,6-dioxo-2,3,6,7-tetrahydro-1H-purin-8-ylmethyl]-phenyl}-3-chloro-benzenesulfonamide

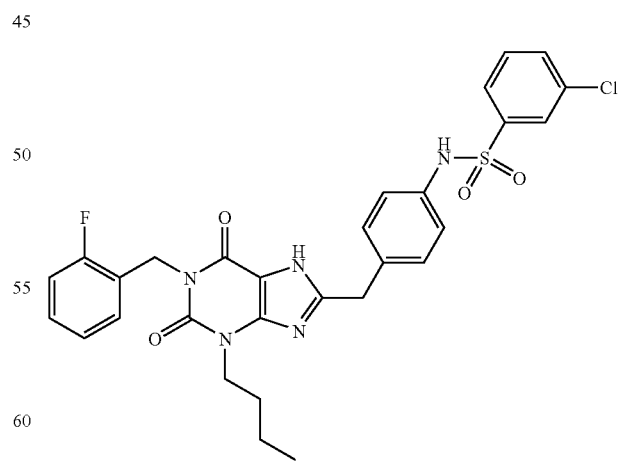

Prepared from 8-(4-amino-benzyl)-3-butyl-1-(2-fluoro-benzyl)-3,7-dihydro-purine-2,6-dione and 3-chloro-benzenesulfonyl chloride. Purity (ELSD, based on MW=596.1)=90%.

Example 45

N-{4-[3-Butyl-1-(2-fluoro-benzyl)-2,6-dioxo-2,3,6,7-tetrahydro-1H-purin-8-ylmethyl]-phenyl}-3-trifluoromethyl-benzenesulfonamide

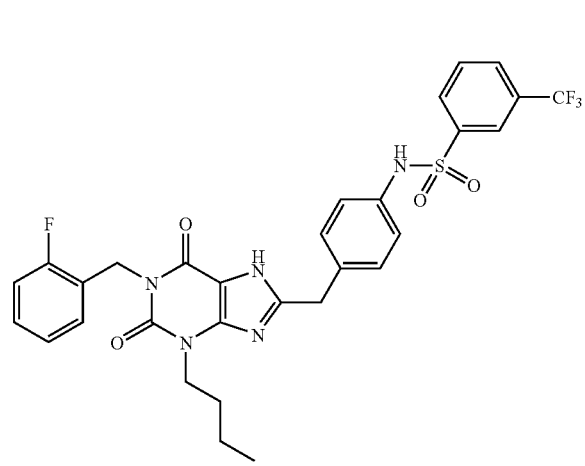

Prepared from 8-(4-amino-benzyl)-3-butyl-1-(2-fluoro-benzyl)-3,7-dihydro-purine-2,6-dione and 3-(trifluoromethyl)-benzenesulfonyl chloride. Purity (ELSD, based on MW=629.6)=97%.

Example 46

N-{4-[3-Butyl-1-(2-fluoro-benzyl)-2,6-dioxo-2,3,6,7-tetrahydro-1H-purin-8-ylmethyl]-phenyl}-3-nitro-benzene sulfonamide

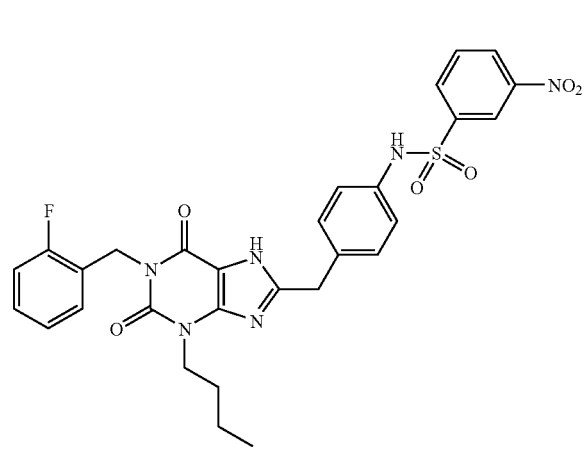

Prepared from 8-(4-amino-benzyl)-3-butyl-1-(2-fluoro-benzyl)-3,7-dihydro-purine-2,6-dione and 3-nitro-benzenesulfonyl chloride. Purity (ELSD, based on MW=606.6)=75%.

Example 47

N-{4-[3-Butyl-1-(2-fluoro-benzyl)-2,6-dioxo-2,3,6,7-tetrahydro-1H-purin-8-ylmethyl]-phenyl}-3-methyl-benzenesulfonamide

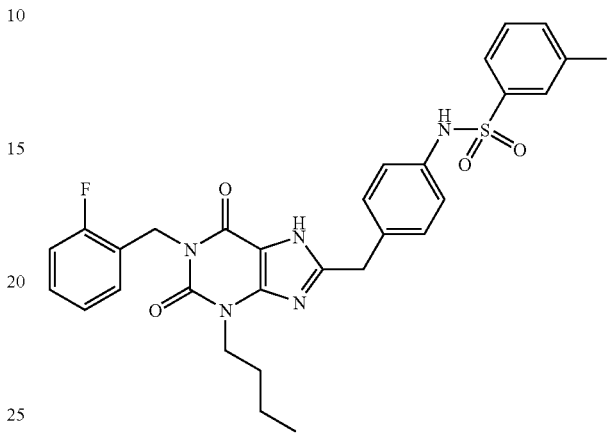

Prepared from 8-(4-amino-benzyl)-3-butyl-1-(2-fluoro-benzyl)-3,7-dihydro-purine-2,6-dione and 3-methyl-benzenesulfonyl chloride. Purity (ELSD, based on MW=575.7)=93%.

Example 48

N-{4-[3-Butyl-1-(2-fluoro-benzyl)-2,6-dioxo-2,3,6,7-tetrahydro-1H-purin-8-ylmethyl]-phenyl}-4-bromo-benzenesulfonamide

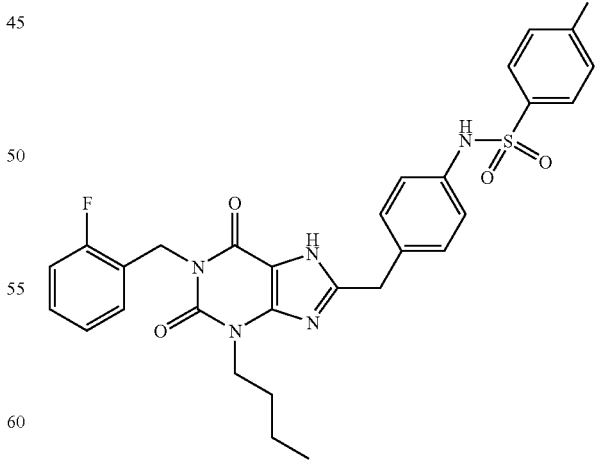

Prepared from 8-(4-amino-benzyl)-3-butyl-1-(2-fluoro-benzyl)-3,7-dihydro-purine-2,6-dione and 4-bromo-benzenesulfonyl chloride. Purity (ELSD, based on MW=640.5)=100%.

Example 49

N-{4-[3-Butyl-1-(2-fluoro-benzyl)-2,6-dioxo-2,3,6,7-tetrahydro-1H-purin-8-ylmethyl]-phenyl}-4-nitro-benzene sulfonamide

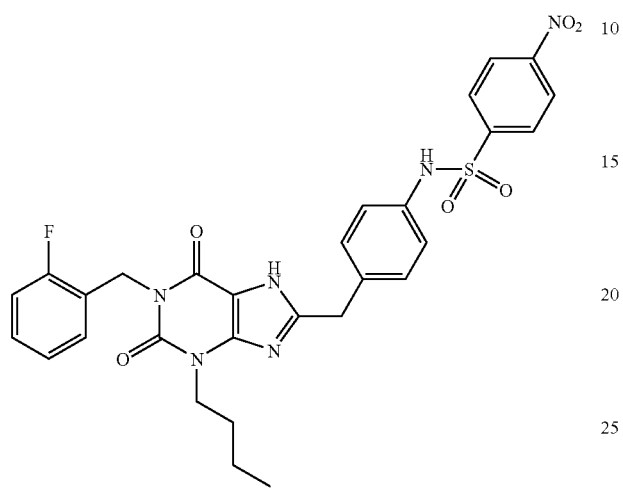

Prepared from 8-(4-amino-benzyl)-3-butyl-1-(2-fluoro-benzyl)-3,7-dihydro-purine-2,6-dione and 4-nitro-benzenesulfonyl chloride. Purity (ELSD, based on MW=606.6)=98%.

Example 50

N-{4-[3-Butyl-1-(2-fluoro-benzyl)-2,6-dioxo-2,3,6,7-tetrahydro-1H-purin-8-ylmethyl]-phenyl}-4-chloro-benzenesulfonamide

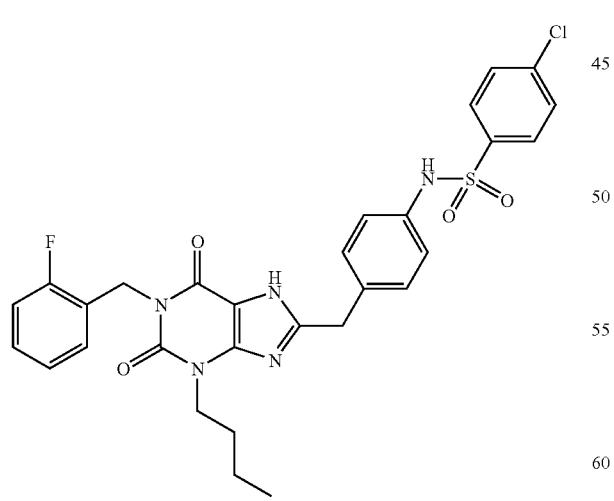

Prepared from 8-(4-amino-benzyl)-3-butyl-1-(2-fluoro-benzyl)-3,7-dihydro-purine-2,6-dione and 4-chloro-benzenesulfonyl chloride. Purity (ELSD, based on MW=596.1)=97%.

Example 51

N-{4-[3-Butyl-1-(2-fluoro-benzyl)-2,6-dioxo-2,3,6,7-tetrahydro-1H-purin-8-ylmethyl]-phenyl}-4-iodo-benzenesulfonamide

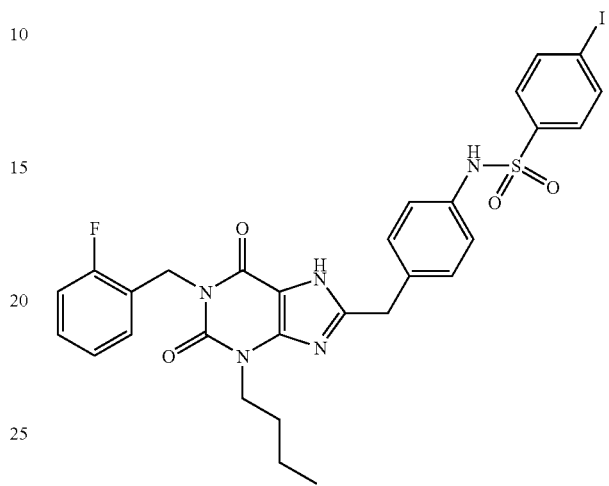

Prepared from 8-(4-amino-benzyl)-3-butyl-1-(2-fluoro-benzyl)-3,7-dihydro-purine-2,6-dione and 4-iodo-benzenesulfonyl chloride. Purity (ELSD, based on MW=687.5)=100%.

Example 52

N-{4-[3-Butyl-1-(2-fluoro-benzyl)-2,6-dioxo-2,3,6,7-tetrahydro-1H-purin-8-ylmethyl]-phenyl}-4-iso-propyl-benzenesulfonamide

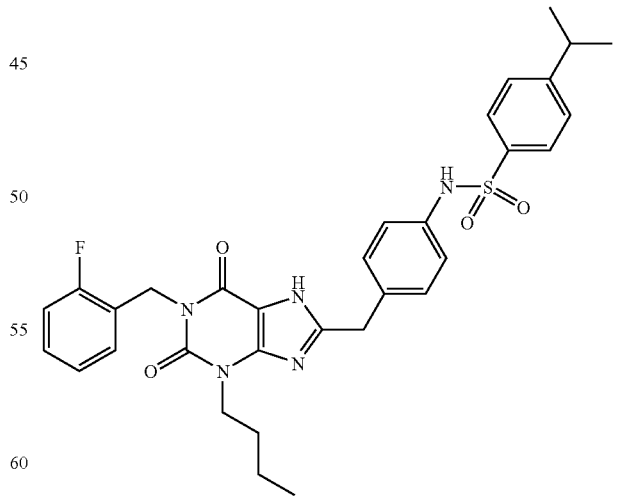

Prepared from 8-(4-amino-benzyl)-3-butyl-1-(2-fluoro-benzyl)-3,7-dihydro-purine-2,6-dione and 4-isopropyl-benzenesulfonyl chloride. Purity (ELSD, based on MW=603.7)=97%.

Example 53

N-{4-[3-Butyl-1-(2-fluoro-benzyl)-2,6-dioxo-2,3,6,7-tetrahydro-1H-purin-8-ylmethyl]-phenyl}-4-methoxy-benzenesulfonamide

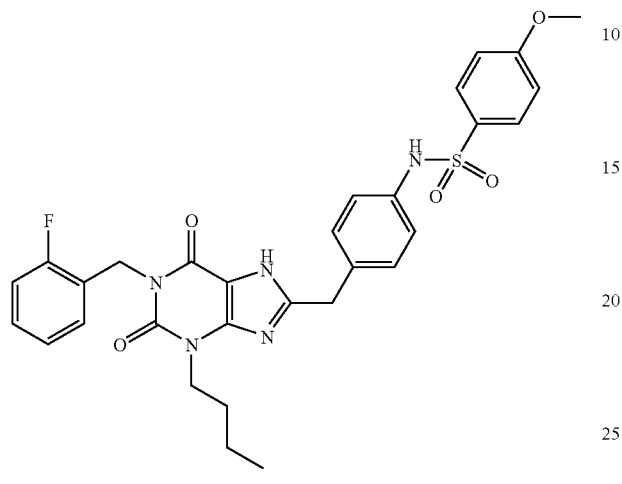

Prepared from 8-(4-amino-benzyl)-3-butyl-1-(2-fluoro-benzyl)-3,7-dihydro-purine-2,6-dione and 4-methoxy-benzenesulfonyl chloride. Purity (ELSD, based on MW=591.7)=94%.

Example 54

N-{4-[3-Butyl-1-(2-fluoro-benzyl)-2,6-dioxo-2,3,6,7-tetrahydro-1H-purin-8-ylmethyl]-phenyl}-4-trifluoromethyl-benzenesulfonamide

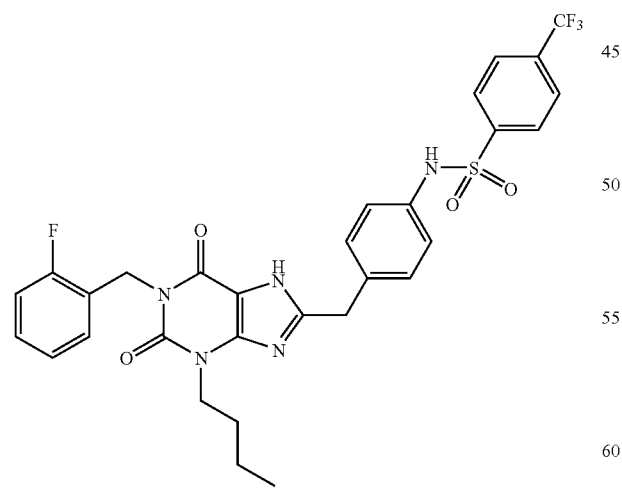

Prepared from 8-(4-amino-benzyl)-3-butyl-1-(2-fluoro-benzyl)-3,7-dihydro-purine-2,6-dione and 4-(trifluoromethyl)-benzenesulfonyl chloride. Purity (ELSD, based on MW=629.6)=94%.

Example 55

N-{4-[3-Butyl-1-(2-fluoro-benzyl)-2,6-dioxo-2,3,6,7-tetrahydro-1H-purin-8-ylmethyl]-phenyl}-4-ethyl-benzene sulfonamide

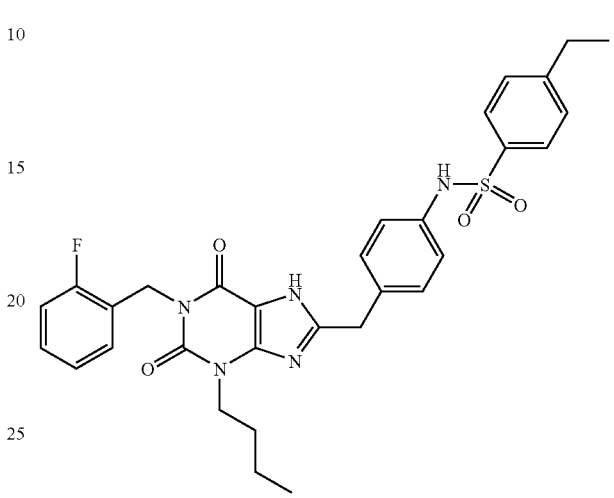

Prepared from 8-(4-amino-benzyl)-3-butyl-1-(2-fluoro-benzyl)-3,7-dihydro-purine-2,6-dione and 4-ethyl-benzenesulfonyl chloride. Purity (ELSD, based on MW=589.7)=90%.

Example 56

N-{4-[3-Butyl-1-(2-fluoro-benzyl)-2,6-dioxo-2,3,6,7-tetrahydro-1H-purin-8-ylmethyl]-phenyl}-4-trifluoromethoxy-benzenesulfonamide

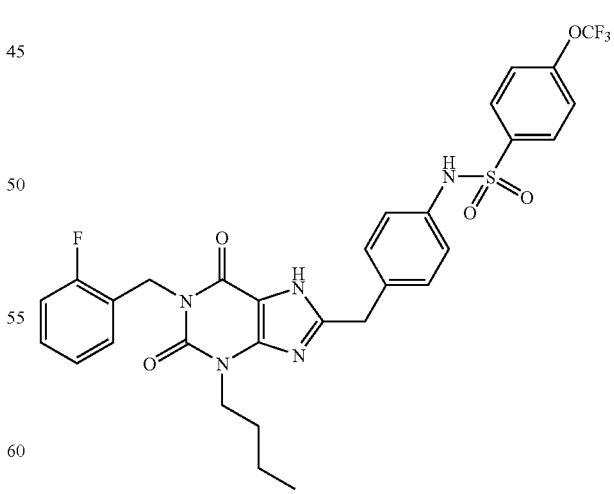

Prepared from 8-(4-amino-benzyl)-3-butyl-1-(2-fluoro-benzyl)-3,7-dihydro-purine-2,6-dione and 4-(trifluoromethoxy)-benzenesulfonyl chloride. Purity (ELSD, based on MW=645.6)=87%.

Example 57

N-{4-[3-Butyl-1-(2-fluoro-benzyl)-2,6-dioxo-2,3,6,7-tetrahydro-1H-purin-8-ylmethyl]-phenyl}-4-fluoro-benzenesulfonamide

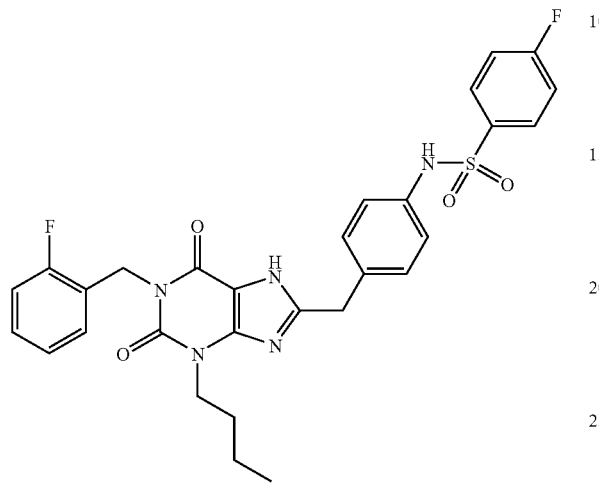

Prepared from 8-(4-amino-benzyl)-3-butyl-1-(2-fluoro-benzyl)-3,7-dihydro-purine-2,6-dione and 4-fluoro-benzenesulfonyl chloride. Purity (ELSD, based on MW=579.6)=93%.

Example 58

N-{4-[3-Butyl-1-(2-fluoro-benzyl)-2,6-dioxo-2,3,6,7-tetrahydro-1H-purin-8-ylmethyl]-phenyl}-2,4-dichloro-benzenesulfonamide

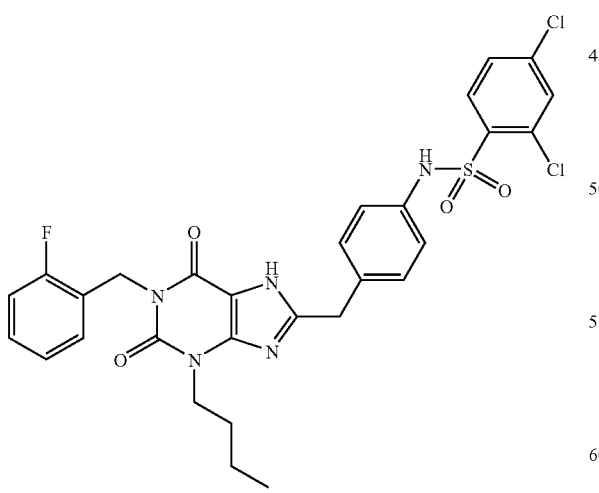

Prepared from 8-(4-amino-benzyl)-3-butyl-1-(2-fluoro-benzyl)-3,7-dihydro-purine-2,6-dione and 2,4-dichloro-benzenesulfonyl chloride. Purity (ELSD, based on MW=630.5)=91%.

Example 59

N-{4-[3-Butyl-1-(2-fluoro-benzyl)-2,6-dioxo-2,3,6,7-tetrahydro-1H-purin-8-ylmethyl]-phenyl}-2,5-dimethoxy-benzenesulfonamide

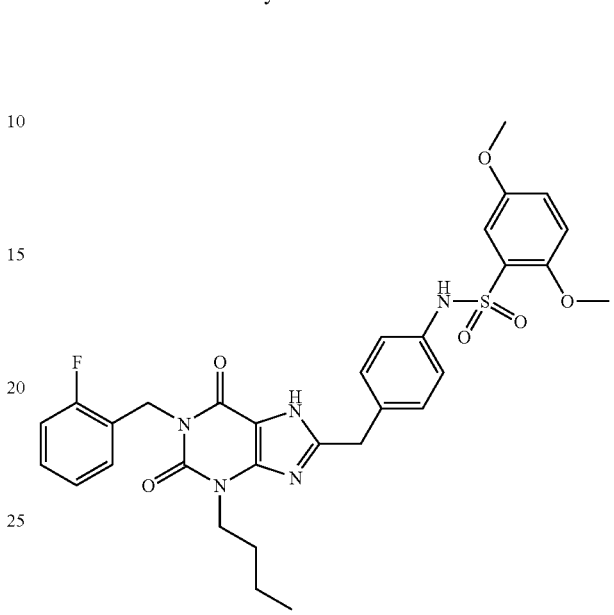

Prepared from 8-(4-amino-benzyl)-3-butyl-1-(2-fluoro-benzyl)-3,7-dihydro-purine-2,6-dione and 2,5-dimethoxy-benzenesulfonyl chloride. Purity (ELSD, based on MW=621.7)=90%.

Example 60

N-{4-[3-Butyl-1-(2-fluoro-benzyl)-2,6-dioxo-2,3,6,7-tetrahydro-1H-purin-8-ylmethyl]-phenyl}-3-chloro-4-methyl-benzenesulfonamide

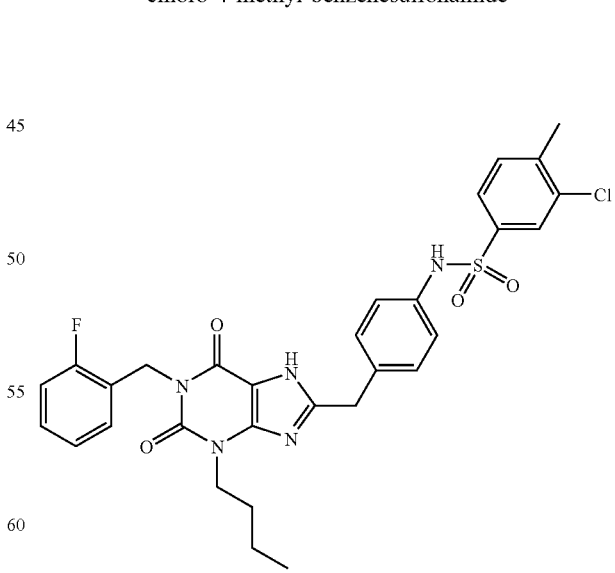

Prepared from 8-(4-amino-benzyl)-3-butyl-1-(2-fluoro-benzyl)-3,7-dihydro-purine-2,6-dione and 3-chloro-4-methyl-benzenesulfonyl chloride. Purity (ELSD, based on MW=610.1)=98%.

Example 61

N-{4-[3-Butyl-1-(2-fluoro-benzyl)-2,6-dioxo-2,3,6,7-tetrahydro-1H-purin-8-ylmethyl]-phenyl}-2-methoxy-5-methyl-benzenesulfonamide

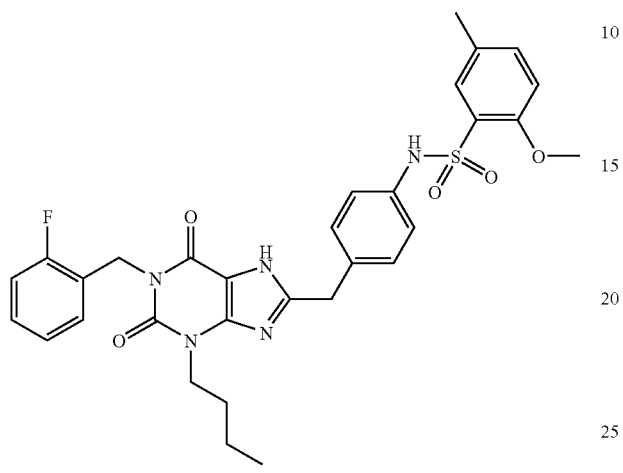

Prepared from 8-(4-amino-benzyl)-3-butyl-1-(2-fluoro-benzyl)-3,7-dihydro-purine-2,6-dione and 2-methoxy-5-methyl-benzenesulfonyl chloride. Purity (ELSD, based on MW=605.7)=94%.

Example 62

N-{4-[3-Butyl-1-(2-fluoro-benzyl)-2,6-dioxo-2,3,6,7-tetrahydro-1H-purin-8-ylmethyl]-phenyl}-2,5-dichloro-benzenesulfonamide

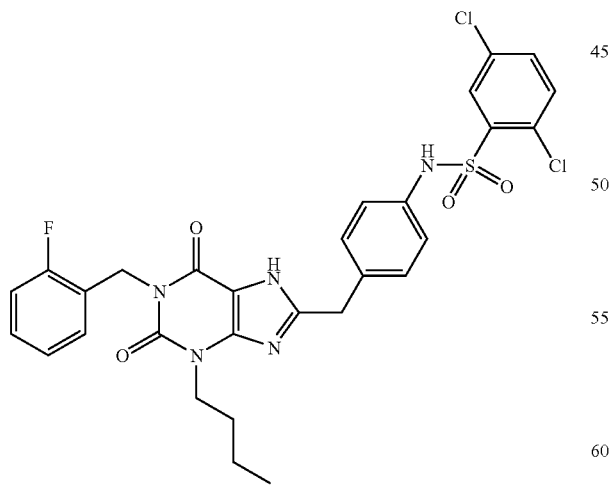

Prepared from 8-(4-amino-benzyl)-3-butyl-1-(2-fluoro-benzyl)-3,7-dihydro-purine-2,6-dione and 2,5-dichloro-benzenesulfonyl chloride. Purity (ELSD, based on MW=630.5)=60%.

Example 63

N-{4-[3-Butyl-1-(2-fluoro-benzyl)-2,6-dioxo-2,3,6,7-tetrahydro-1H-purin-8-ylmethyl]-phenyl}-3-chloro-2-methyl-benzenesulfonamide

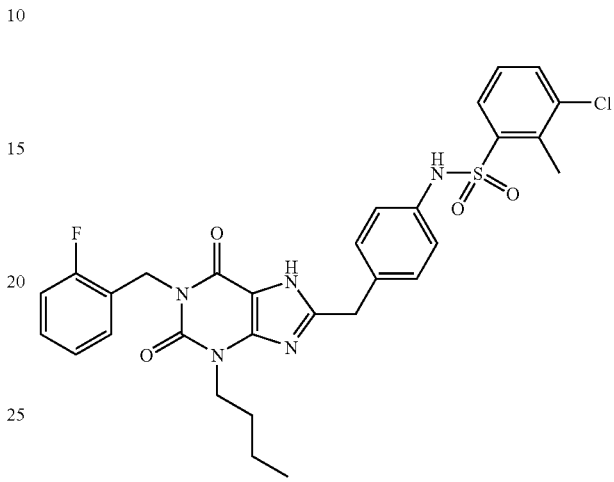

Prepared from 8-(4-amino-benzyl)-3-butyl-1-(2-fluoro-benzyl)-3,7-dihydro-purine-2,6-dione and 3-chloro-2-methyl-benzenesulfonyl chloride. Purity (ELSD, based on MW=610.1)=80%.

Example 64

N-{4-[3-Butyl-1-(2-fluoro-benzyl)-2,6-dioxo-2,3,6,7-tetrahydro-1H-purin-8-ylmethyl]-phenyl}-2,6-dichloro-benzenesulfonamide Prepared from 8-(4-amino-benzyl)-3-butyl-1-(2-fluoro-benzyl)-3,7-dihydro-purine-2,6-dione and 2,6-dichloro-benzenesulfonyl chloride. Purity (ELSD, based on MW=630.5)=80%.

Example 65

N-{4-[3-Butyl-1-(2-fluoro-benzyl)-2,6-dioxo-2,3,6,7-tetrahydro-1H-purin-8-ylmethyl]-phenyl}-2,3-dichloro-benzenesulfonamide

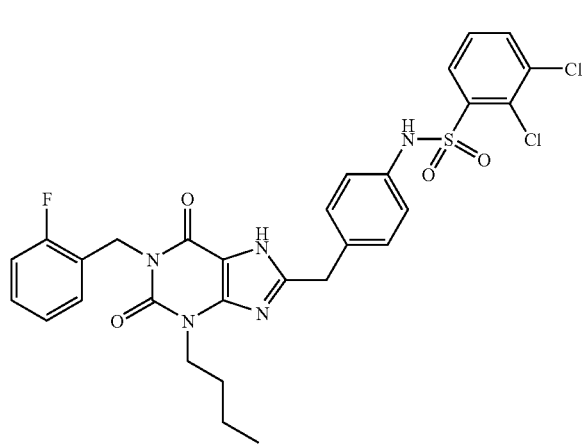

Prepared from 8-(4-amino-benzyl)-3-butyl-1-(2-fluoro-benzyl)-3,7-dihydro-purine-2,6-dione and 2,3-dichloro-benzenesulfonyl chloride. Purity (ELSD, based on MW=630.5)=70%.

Example 66

N-{4-[3-Butyl-1-(2-fluoro-benzyl)-2,6-dioxo-2,3,6,7-tetrahydro-1H-purin-8-ylmethyl]-phenyl}-3,4-dimethoxy-benzenesulfonamide

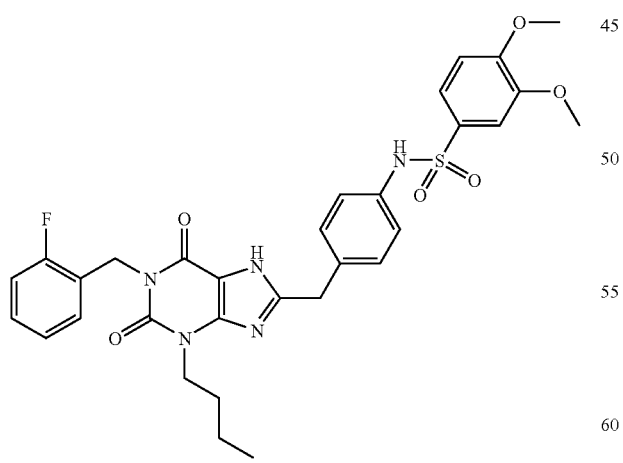

Prepared from 8-(4-amino-benzyl)-3-butyl-1-(2-fluoro-benzyl)-3,7-dihydro-purine-2,6-dione and 3,4-dimethoxy-benzenesulfonyl chloride. Purity (ELSD, based on MW=621.7)=94%.

Example 67

N-{4-[3-Butyl-1-(2-fluoro-benzyl)-2,6-dioxo-2,3,6,7-tetrahydro-1H-purin-8-ylmethyl]-phenyl}-2-chloro-6-methyl-benzenesulfonamide

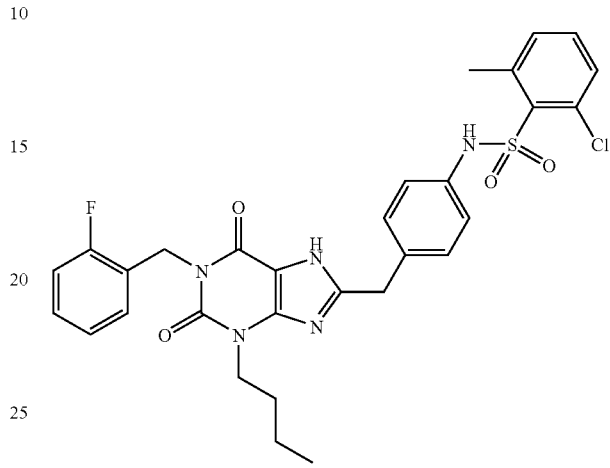

Prepared from 8-(4-amino-benzyl)-3-butyl-1-(2-fluoro-benzyl)-3,7-dihydro-purine-2,6-dione and 2-chloro-6-methyl-benzenesulfonyl chloride. Purity (ELSD, based on MW=610.1)=70%.

Example 68

N-{4-[3-Butyl-1-(2-fluoro-benzyl)-2,6-dioxo-2,3,6,7-tetrahydro-1H-purin-8-ylmethyl]-phenyl}-3,5-dichloro-benzenesulfonamide

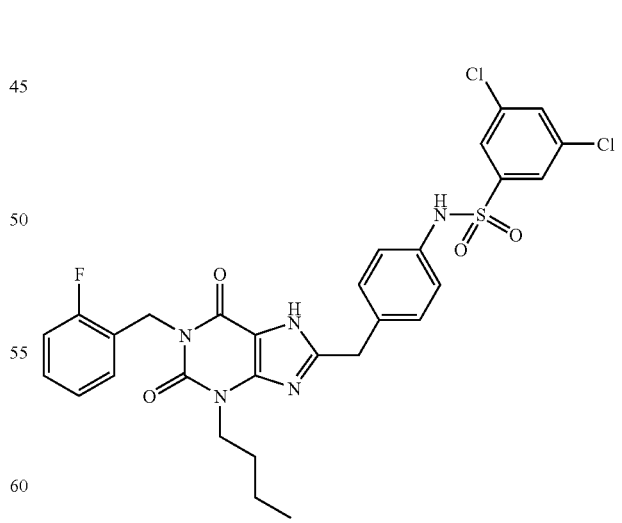

Prepared from 8-(4-amino-benzyl)-3-butyl-1-(2-fluoro-benzyl)-3,7-dihydro-purine-2,6-dione and 3,5-dichloro-benzenesulfonyl chloride. Purity (ELSD, based on MW=630.5)=97%.

Example 69

N-{4-[3-Butyl-1-(2-fluoro-benzyl)-2,6-dioxo-2,3,6,7-tetrahydro-1H-purin-8-ylmethyl]-phenyl}-3,4-dichloro-benzenesulfonamide

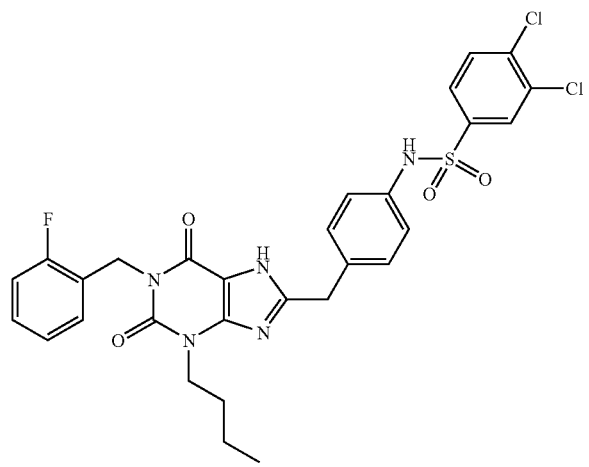

Prepared from 8-(4-amino-benzyl)-3-butyl-1-(2-fluoro-benzyl)-3,7-dihydro-purine-2,6-dione and 3,4-dichloro-benzenesulfonyl chloride. Purity (ELSD, based on MW=630.5)=100%.

Example 70

N-{4-[3-Butyl-1-(2-fluoro-benzyl)-2,6-dioxo-2,3,6,7-tetrahydro-1H-purin-8-ylmethyl]-phenyl}-2,5-dimethyl-benzenesulfonamide

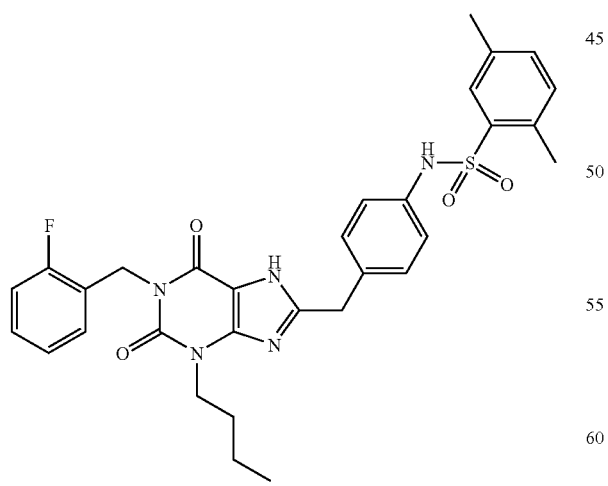

Prepared from 8-(4-amino-benzyl)-3-butyl-1-(2-fluoro-benzyl)-3,7-dihydro-purine-2,6-dione and 2,5-dimethyl-benzenesulfonyl chloride. Purity (ELSD, based on MW=589.7)=85%.

Example 71

N-{4-[3-Butyl-1-(2-fluoro-benzyl)-2,6-dioxo-2,3,6,7-tetrahydro-1H-purin-8-ylmethyl]-phenyl}-5-fluoro-2-methyl-benzenesulfonamide

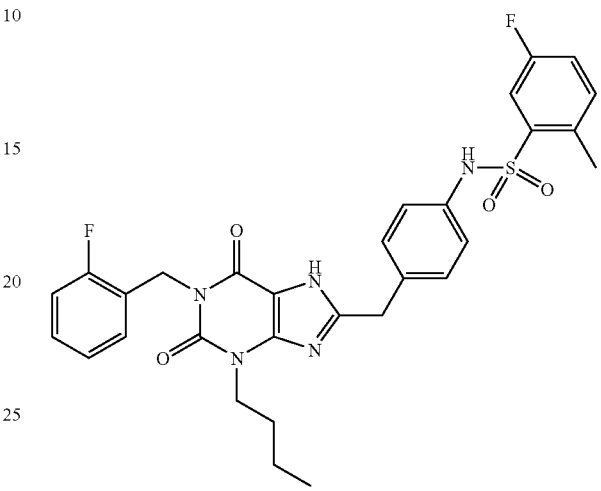

Prepared from 8-(4-amino-benzyl)-3-butyl-1-(2-fluoro-benzyl)-3,7-dihydro-purine-2,6-dione and 5-fluoro-2-methyl-benzenesulfonyl chloride. Purity (ELSD, based on MW=593.7)=92%.

Example 72

N-{4-[3-Butyl-1-(2-fluoro-benzyl)-2,6-dioxo-2,3,6,7-tetrahydro-1H-purin-8-ylmethyl]-phenyl}-2-chloro-4-fluoro-benzenesulfonamide

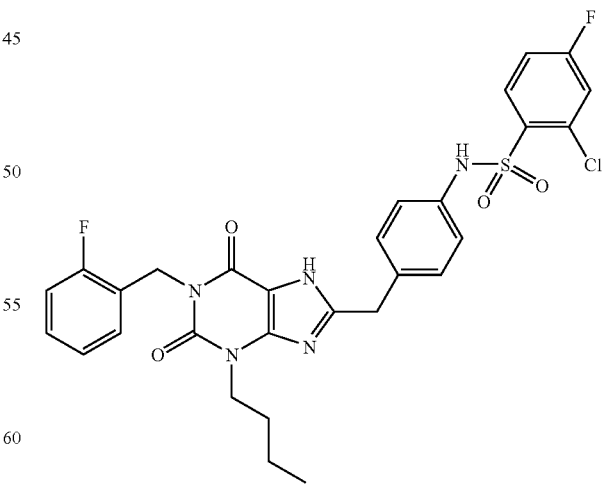

Prepared from 8-(4-amino-benzyl)-3-butyl-1-(2-fluoro-benzyl)-3,7-dihydro-purine-2,6-dione and 2-chloro-4-fluoro-benzenesulfonyl chloride. Purity (ELSD, based on MW=614.1)=93%.

Example 73

N-{4-[3-Butyl-1-(2-fluoro-benzyl)-2,6-dioxo-2,3,6,7-tetrahydro-1H-purin-8-ylmethyl]-phenyl}-2,4-difluoro-benzenesulfonamide

Example 75

N-{4-[3-Butyl-1-(2-fluoro-benzyl)-2,6-dioxo-2,3,6,7-tetrahydro-1H-purin-8-ylmethyl]-phenyl}-3-chloro-4-fluoro-benzenesulfonamide

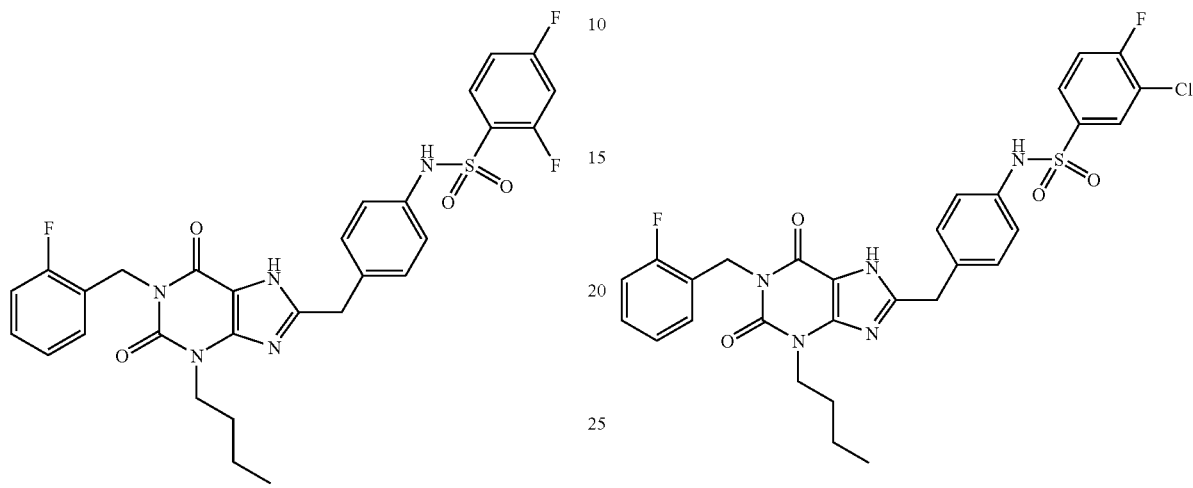

Prepared from 8-(4-amino-benzyl)-3-butyl-1-(2-fluoro-benzyl)-3,7-dihydro-purine-2,6-dione and 2,4-difluoro-benzenesulfonyl chloride. Purity (ELSD, based on MW=597.6)=95%.

Prepared from 8-(4-amino-benzyl)-3-butyl-1-(2-fluoro-benzyl)-3,7-dihydro-purine-2,6-dione and 3-chloro-4-fluoro-benzenesulfonyl chloride. Purity (ELSD, based on MW=614.1)=95%.

Example 74

N-{4-[3-Butyl-1-(2-fluoro-benzyl)-2,6-dioxo-2,3,6,7-tetrahydro-1H-purin-8-ylmethyl]-phenyl}-2-methyl-5-nitro-benzenesulfonamide

Example 76

N-{4-[3-Butyl-1-(2-fluoro-benzyl)-2,6-dioxo-2,3,6,7-tetrahydro-1H-purin-8-ylmethyl]-phenyl}-2,6-difluoro-benzenesulfonamide

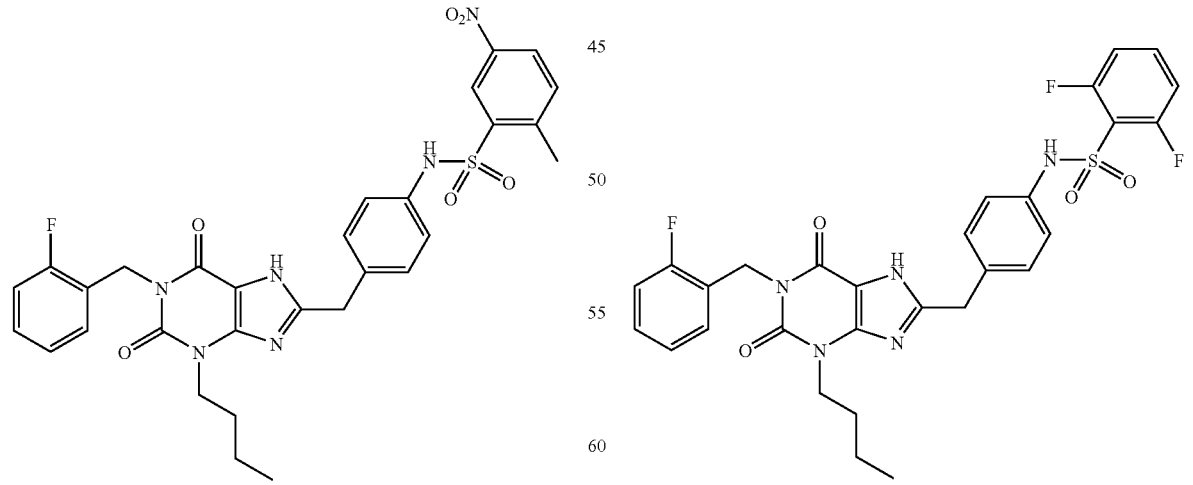

Prepared from 8-(4-amino-benzyl)-3-butyl-1-(2-fluoro-benzyl)-3,7-dihydro-purine-2,6-dione and 2-methyl-5-nitro-benzenesulfonyl chloride. Purity (ELSD, based on MW=620.7)=88%.

Prepared from 8-(4-amino-benzyl)-3-butyl-1-(2-fluoro-benzyl)-3,7-dihydro-purine-2,6-dione and 2,6-difluoro-benzenesulfonyl chloride. Purity (ELSD, based on MW=597.6)=80%.

Example 77

N-{4-[3-Butyl-1-(2-fluoro-benzyl)-2,6-dioxo-2,3,6,
7-tetrahydro-1H-purin-8-ylmethyl]-phenyl}-3,4-
difluoro-benzenesulfonamide

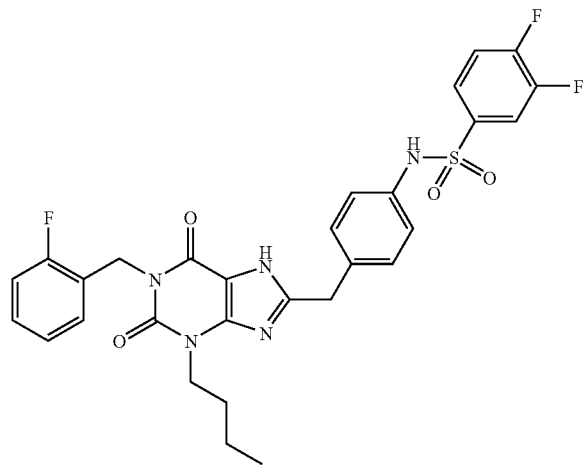

Prepared from 8-(4-amino-benzyl)-3-butyl-1-(2-fluoro-benzyl)-3,7-dihydro-purine-2,6-dione and 3,4-difluoro-benzenesulfonyl chloride. Purity (ELSD, based on MW=597.6)=95%.

Example 78

N-{4-[3-Butyl-1-(2-fluoro-benzyl)-2,6-dioxo-2,3,6,
7-tetrahydro-1H-purin-8-ylmethyl]-phenyl}-2,4,6-
trimethyl-benzenesulfonamide

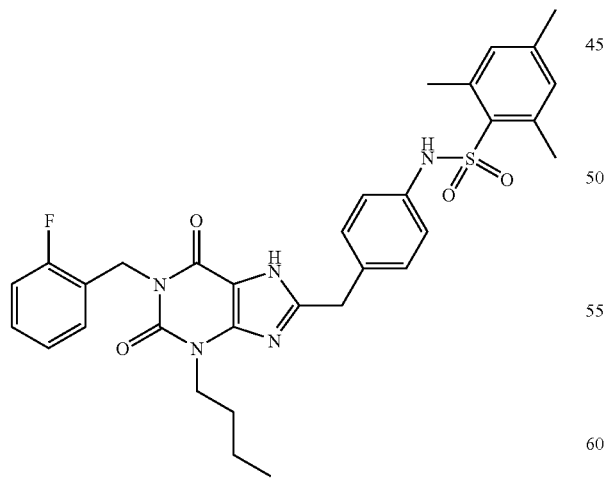

Prepared from 8-(4-amino-benzyl)-3-butyl-1-(2-fluoro-benzyl)-3,7-dihydro-purine-2,6-dione and 2,4,6-trimethyl-benzenesulfonyl chloride. Purity (ELSD, based on MW=603.7)=60%.

Example 79

N-{4-[3-Butyl-1-(2-fluoro-benzyl)-2,6-dioxo-2,3,6,
7-tetrahydro-1H-purin-8-ylmethyl]-phenyl}-4-
chloro-2,5-dimethyl-benzenesulfonamide

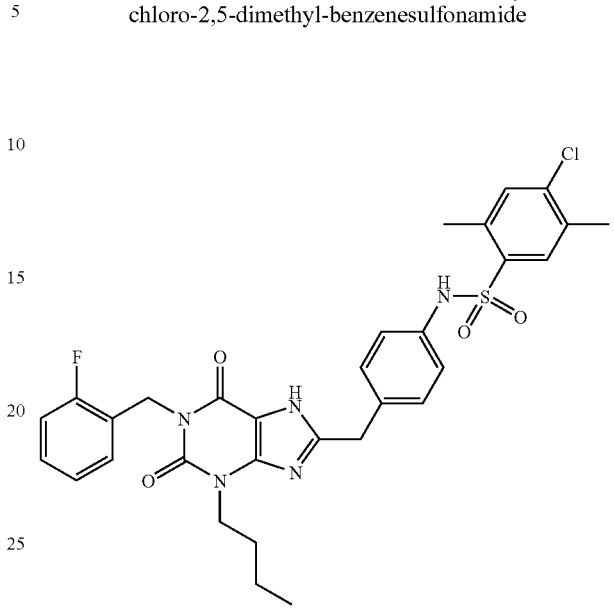

Prepared from 8-(4-amino-benzyl)-3-butyl-1-(2-fluoro-benzyl)-3,7-dihydro-purine-2,6-dione and 4-chloro-2,5-dimethyl-benzenesulfonyl chloride. Purity (ELSD, based on MW=624.1)=93%.

Example 80

N-{4-[3-Butyl-1-(2-fluoro-benzyl)-2,6-dioxo-2,3,6,
7-tetrahydro-1H-purin-8-ylmethyl]-phenyl}-2,4-
dichloro-6-methyl-benzenesulfonamide

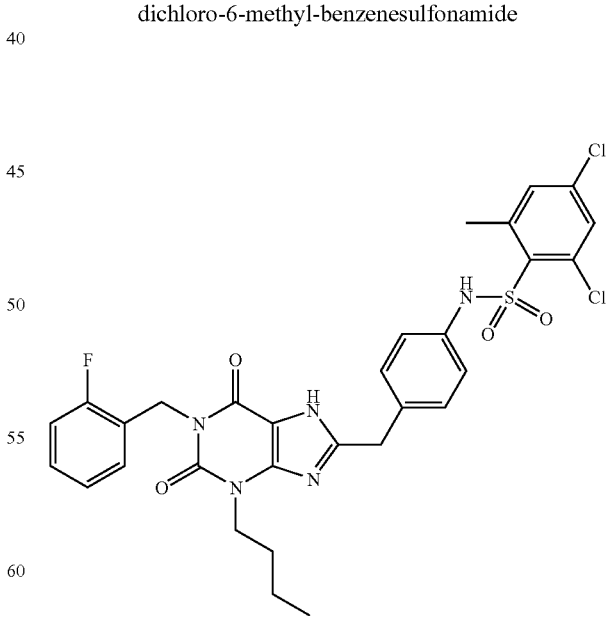

Prepared from 8-(4-amino-benzyl)-3-butyl-1-(2-fluoro-benzyl)-3,7-dihydro-purine-2,6-dione and 2,4-dichloro-6-methyl-benzenesulfonyl chloride. Purity (ELSD, based on MW=644.6)=85%.

Example 81

N-{4-[3-Butyl-1-(2-fluoro-benzyl)-2,6-dioxo-2,3,6,7-tetrahydro-1H-purin-8-ylmethyl]-phenyl}-2,4-dichloro-5-methyl-benzenesulfonamide

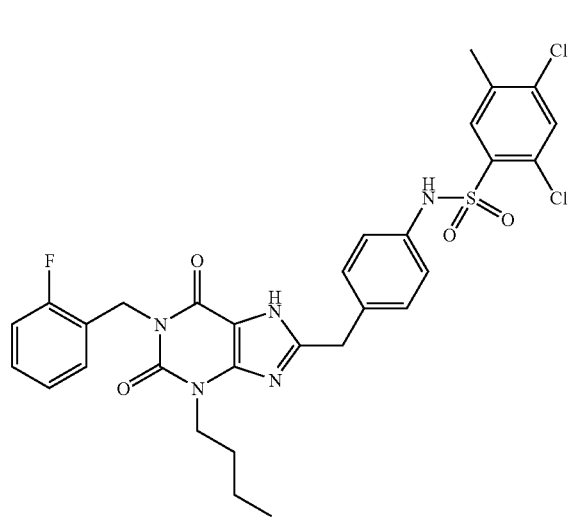

Prepared from 8-(4-amino-benzyl)-3-butyl-1-(2-fluoro-benzyl)-3,7-dihydro-purine-2,6-dione and 2,4-dichloro-5-methyl-benzenesulfonyl chloride. Purity (ELSD, based on MW=644.6)=82%.

Example 82

N-{4-[3-Butyl-1-(2-fluoro-benzyl)-2,6-dioxo-2,3,6,7-tetrahydro-1H-purin-8-ylmethyl]-phenyl}-2,3,5,6-tetramethyl-benzenesulfonamide

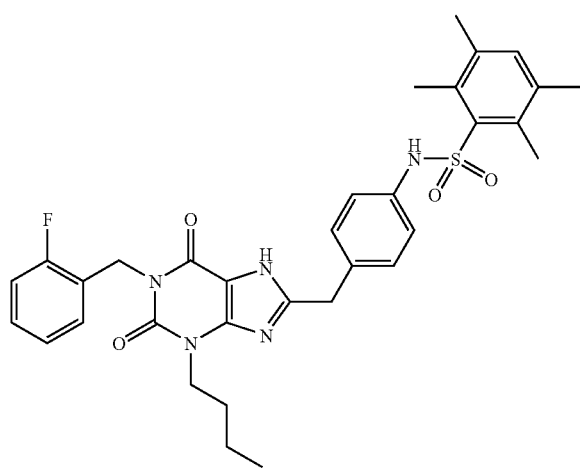

Prepared from 8-(4-amino-benzyl)-3-butyl-1-(2-fluoro-benzyl)-3,7-dihydro-purine-2,6-dione and 2,3,5,6-tetramethyl-benzenesulfonyl chloride. Purity (ELSD, based on MW=617.7)=80%.

Example 83

N-{4-[3-Butyl-1-(2-fluoro-benzyl)-2,6-dioxo-2,3,6,7-tetrahydro-1H-purin-8-ylmethyl]-phenyl}-4-methoxy-2,3,6-trimethyl-benzenesulfonamide

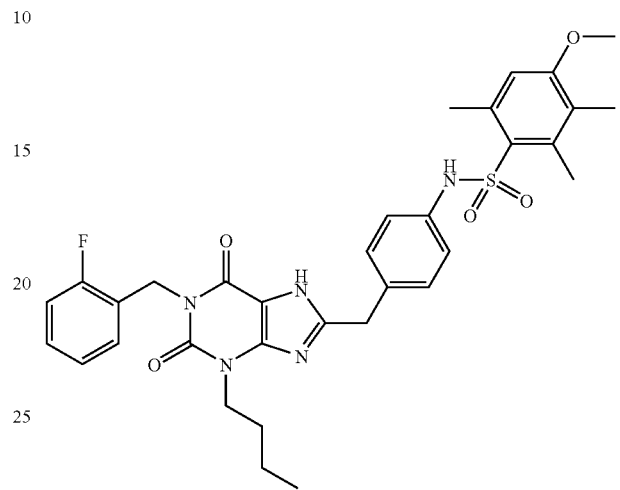

Prepared from 8-(4-amino-benzyl)-3-butyl-1-(2-fluoro-benzyl)-3,7-dihydro-purine-2,6-dione and 4-methoxy-2,3,6-trimethyl-benzenesulfonyl chloride. Purity (ELSD, based on MW=633.7)=80%.

Example 84

N-{4-[3-Butyl-1-(2-fluoro-benzyl)-2,6-dioxo-2,3,6,7-tetrahydro-1H-purin-8-ylmethyl]-phenyl}-1-naphthalenesulfonamide

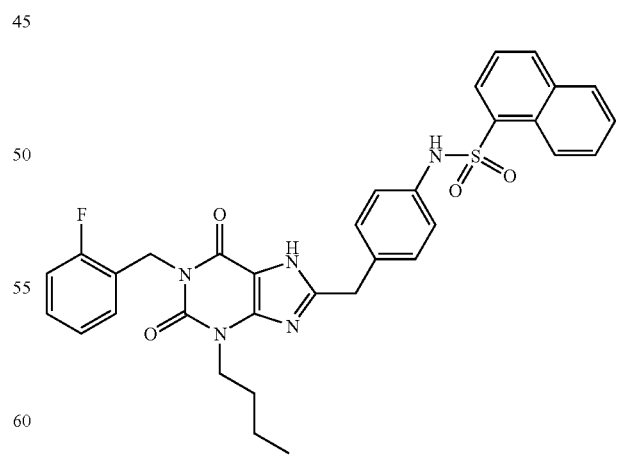

Prepared from 8-(4-amino-benzyl)-3-butyl-1-(2-fluoro-benzyl)-3,7-dihydro-purine-2,6-dione and naphthalene-1-sulfonyl chloride. Purity (ELSD, based on MW=611.7)=81%.

Example 85

5-Dimethylamino-naphthalene-1-sulfonic acid {4-[3-butyl-1-(2-fluoro-benzyl)-2,6-dioxo-2,3,6,7-tetrahydro-1H-purin-8-ylmethyl]-phenyl}-amide

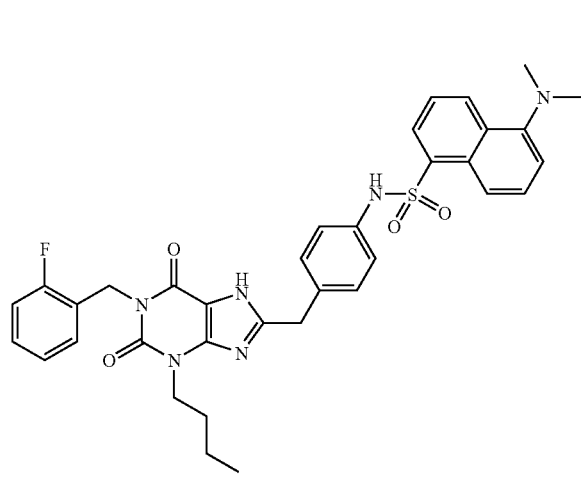

Prepared from 8-(4-amino-benzyl)-3-butyl-1-(2-fluoro-benzyl)-3,7-dihydro-purine-2,6-dione and 5-dimethylamino-1-naphthalenesulfonyl chloride. Purity (ELSD, based on MW=654.8)=90%.

Example 86

Benzo[1,2,5]oxadiazole-4-sulfonic acid {4-[3-butyl-1-(2-fluoro-benzyl)-2,6-dioxo-2,3,6,7-tetrahydro-1H-purin-8-ylmethyl]-phenyl}-amide

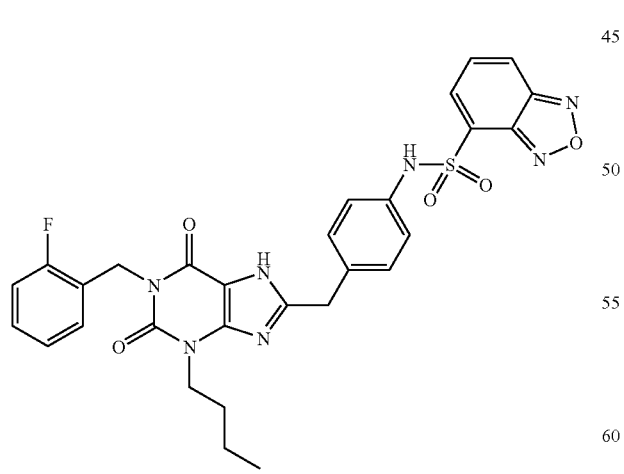

Prepared from 8-(4-amino-benzyl)-3-butyl-1-(2-fluoro-benzyl)-3,7-dihydro-purine-2,6-dione and benzo[1,2,5]oxadiazole-4-sulfonyl chloride. Purity (ELSD, based on MW=603.6)=95%.

Example 87

Benzo[1,2,5]thiadiazole-4-sulfonic acid {4-[3-butyl-1-(2-fluoro-benzyl)-2,6-dioxo-2,3,6,7-tetrahydro-1H-purin-8-ylmethyl]-phenyl}-amide

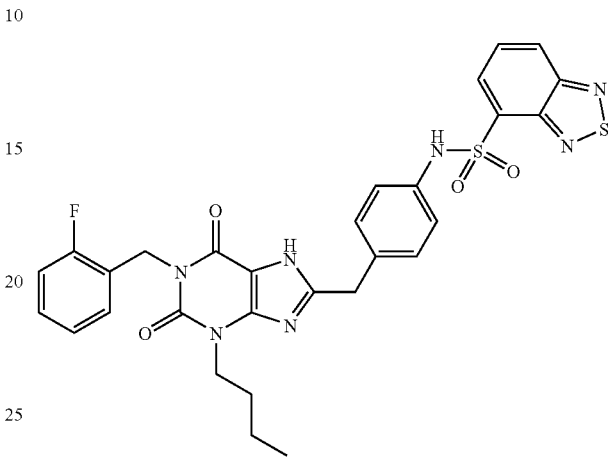

Prepared from 8-(4-amino-benzyl)-3-butyl-1-(2-fluoro-benzyl)-3,7-dihydro-purine-2,6-dione and benzo[1,2,5]thiadiazole-4-sulfonyl chloride. Purity (ELSD, based on MW=619.7)=80%.

Example 88

6-Chloro-pyridine-3-sulfonic acid {4-[3-butyl-1-(2-fluoro-benzyl)-2,6-dioxo-2,3,6,7-tetrahydro-1H-purin-8-ylmethyl]-phenyl}-amide

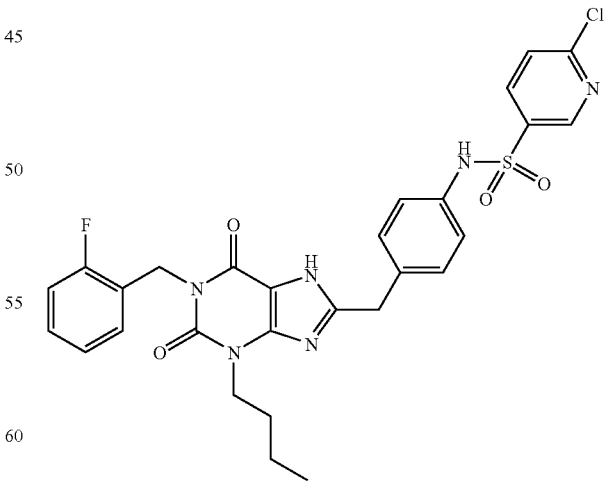

Prepared from 8-(4-amino-benzyl)-3-butyl-1-(2-fluoro-benzyl)-3,7-dihydro-purine-2,6-dione and 6-chloro-pyridine-3-sulfonyl chloride. Purity (ELSD, based on MW=597.1)=98%.

Example 89

Thiophene-2-sulfonic acid {4-[3-butyl-1-(2-fluoro-benzyl)-2,6-dioxo-2,3,6,7-tetrahydro-1H-purin-8-ylmethyl]-phenyl}-amide

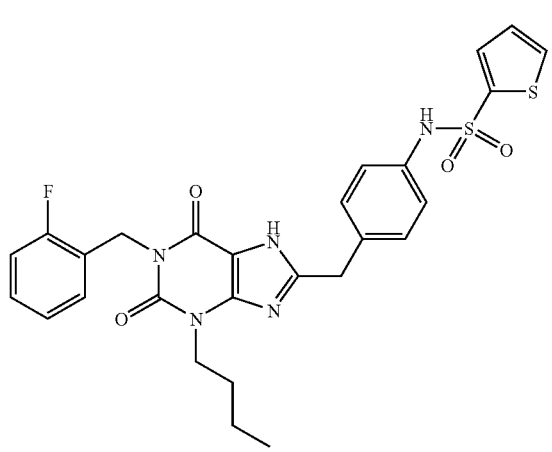

Prepared from 8-(4-amino-benzyl)-3-butyl-1-(2-fluoro-benzyl)-3,7-dihydro-purine-2,6-dione and 2-thio-benzene-sulfonyl chloride. Purity (ELSD, based on MW=567.7)=67%.

Example 90

5-Chlorothiophene-2-sulfonic acid {4-[3-butyl-1-(2-fluoro-benzyl)-2,6-dioxo-2,3,6,7-tetrahydro-1H-purin-8-ylmethyl]-phenyl}-amide

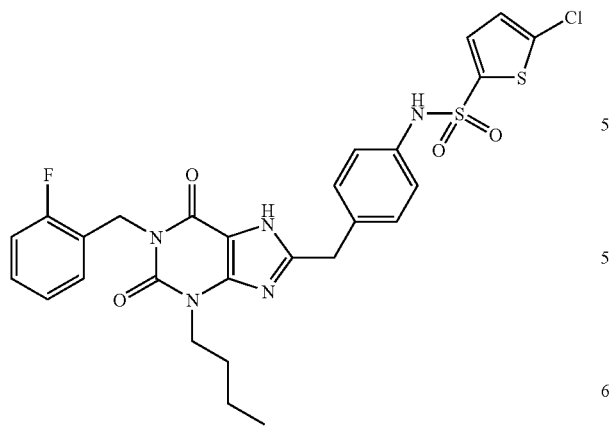

Prepared from 8-(4-amino-benzyl)-3-butyl-1-(2-fluoro-benzyl)-3,7-dihydro-purine-2,6-dione and 5-chloro-2-thio-benzenesulfonyl chloride. Purity (ELSD, based on MW=602.1)=96%.

Example 91

5-Bromo-thiophene-2-sulfonic acid {4-[3-butyl-1-(2-fluoro-benzyl)-2,6-dioxo-2,3,6,7-tetrahydro-1H-purin-8-ylmethyl]-phenyl}-amide

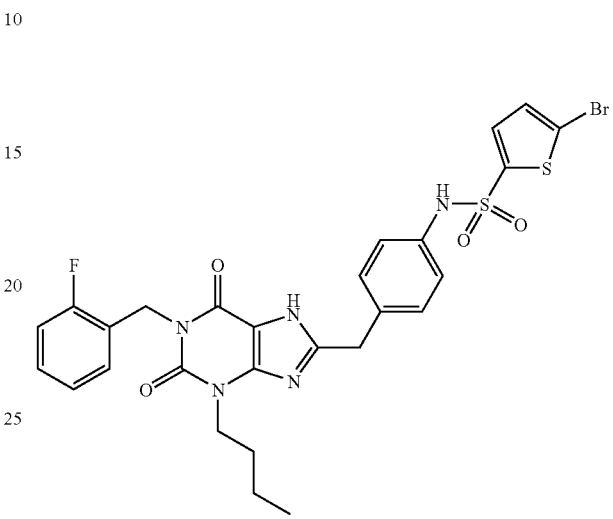

Prepared from 8-(4-amino-benzyl)-3-butyl-1-(2-fluoro-benzyl)-3,7-dihydro-purine-2,6-dione and 5-bromo-2-thio-benzenesulfonyl chloride. Purity (ELSD, based on MW=646.6)=92%.

Example 92

4,5-Dibromothiophene-2-sulfonic acid {4-[3-butyl-1-(2-fluoro-benzyl)-2,6-dioxo-2,3,6,7-tetrahydro-1H-purin-8-ylmethyl]-phenyl}-amide

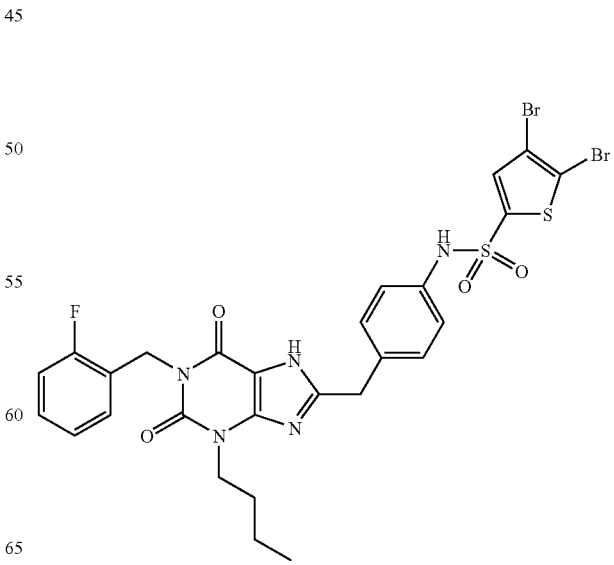

Prepared from 8-(4-amino-benzyl)-3-butyl-1-(2-fluoro-benzyl)-3,7-dihydro-purine-2,6-dione and 4,5-dibromo-2-thio-benzenesulfonyl chloride. Purity (ELSD, based on MW=725.5)=97%.

Example 93

3-{4-[3-Butyl-1-(2-fluoro-benzyl)-2,6-dioxo-2,3,6,7-tetrahydro-1H-purin-8-ylmethyl]-phenylsulfamoyl}-thiophene-2-carboxylic acid methyl ester

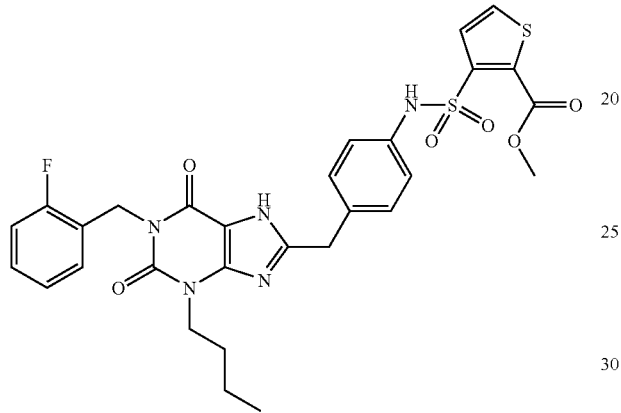

Prepared from 8-(4-amino-benzyl)-3-butyl-1-(2-fluoro-benzyl)-3,7-dihydro-purine-2,6-dione and 3-chlorosulfonyl-thiophene-2-carboxylic acid methyl ester. Purity (ELSD, based on MW=625.7)=92%.

Example 94

4-(1-Benzyl-3-butyl-2,6-dioxo-2,3,6,7-tetrahydro-1H-purin-8-ylmethyl)-benzenesulfonamide.

Prepared by the same method as described for 5-chloro-1,3-dimethyl-1H-pyrazole-4-sulfonic acid {4-[3-butyl-1-(2-fluoro-benzyl)-2,6-dioxo-2,3,6,7-tetrahydro-1H-purin-8-ylmethyl]-phenyl}-amide (example 34) except that in step 2 benzyl bromide was used in place of 2-fluorobenzyl bromide and in step 3 4-(2-amino-ethyl)-benzenesulfonamide was used in place of 2-(4-nitro-phenyl)-ethylamine hydrochloride salt. 4-(1-Benzyl-3-butyl-2,6-dioxo-2,3,6,7-tetrahydro-1H-purin-8-ylmethyl)-benzenesulfonamide was obtained as a colorless solid; LRMS for $C_{23}H_{25}N_5O_4S$ (M+H)$^+$ at m/z=468.27.

The in vitro biological activity of several representative preferred compounds of the present invention in the foregoing PEPCK enzymatic assay as represented by in vitro potency is presented in Table 1 below.

TABLE 1

| Compound | IC$_{50}$ (μM) |
| --- | --- |
| 1,3-Dimethyl-1H-pyrazole-4-sulfonic acid {4-[3-cyclopropylmethyl-1-(2-fluoro-benzyl)-2,6-dioxo-2,3,6,7-tetrahydro-1H-purin-8-ylmethyl]-phenyl}-amide (example 7) | 0.15 |
| N-(5-{4-[3-Cyclopropylmethyl-1-(2-fluoro-benzyl)-2,6-dioxo-2,3,6,7-tetrahydro-1H-purin-8-ylmethyl]-phenylsulfamoyl}-4-methyl-thiazol-2-yl)-acetamide (example 10) | 0.22 |
| 2-Amino-4-methyl-thiazole-5-sulfonic acid {4-[3-cyclopropylmethyl-1-(2-fluoro-benzyl)-2,6-dioxo-2,3,6,7-tetrahydro-1H-purin-8-ylmethyl]-phenyl}-amide trifluoro-acetic acid salt (example 11) | 0.23 |
| 5-Chloro-1,3-dimethyl-1H-pyrazole-4-sulfonic acid {4-[3-cyclopropylmethyl-1-(2-fluoro-benzyl)-2,6-dioxo-2,3,6,7-tetrahydro-1H-purin-8-ylmethyl]-phenyl}-amide (example 1) | 0.29 |
| 1,2-Dimethyl-1H-imidazole-4-sulfonic acid {4-[3-cyclopropylmethyl-1-(2-fluoro-benzyl)-2,6-dioxo-2,3,6,7-tetrahydro-1H-purin-8-ylmethyl]-phenyl}-amide (example 13) | 0.34 |
| 1-Methyl-1H-pyrazole-4-sulfonic acid {4-[3-cyclopropylmethyl-1-(2-fluoro-benzyl)-2,6-dioxo-2,3,6,7-tetrahydro-1H-purin-8-ylmethyl]-phenyl}-amide (example 2) | 0.39 |
| 1-Methyl-1H-imidazole-4-sulfonic acid {4-[3-cyclopropylmethyl-1-(2-fluoro-benzyl)-2,6-dioxo-2,3,6,7-tetrahydro-1H-purin-8-ylmethyl]-phenyl}-amide (example 14) | 0.41 |
| Quinoline-8-sulfonic acid {4-[3-cyclopropylmethyl-1-(2-fluoro-benzyl)-2,6-dioxo-2,3,6,7-tetrahydro-1H-purin-8-ylmethyl]-phenyl}-amide (example 19) | 0.45 |
| 3,5-Dimethyl-isoxazole-4-sulfonic acid {4-[3-cyclopropylmethyl-1-(2-fluoro-benzyl)-2,6-dioxo-2,3,6,7-tetrahydro-1H-purin-8-ylmethyl]-phenyl}-amide (example 12) | 0.79 |
| 5-Chloro-1,3-dimethyl-1H-pyrazole-4-sulfonic acid {6-[3-butyl-1-(2-fluoro-benzyl)-2,6-dioxo-2,3,6,7-tetrahydro-1H-purin-8-ylmethyl]-pyridin-3-yl}-amide (example 25) | 0.88 |

TABLE 1-continued

| Compound | IC$_{50}$ (µM) |
|---|---|
| N-{4-[3-Cyclopropylmethyl-1-(2-fluoro-benzyl)-2,6-dioxo-2,3,6,7-tetrahydro-1H-purin-8-ylmethyl]-phenyl}-N,N-dimethylsulfamide (example 17) | 0.96 |
| 5-Chloro-1,3-dimethyl-1H-pyrazole-4-sulfonic acid {6-[3-cyclobutylmethyl-1-(2-fluoro-benzyl)-2,6-dioxo-2,3,6,7-tetrahydro-1H-purin-8-ylmethyl]-pyridin-3-yl}-amide (example 26) | 0.98 |
| 5-Chloro-1,3-dimethyl-1H-pyrazole-4-sulfonic acid {3-[3-cyclopropylmethyl-1-(2-fluoro-benzyl)-2,6-dioxo-2,3,6,7-tetrahydro-1H-purin-8-ylmethyl]-phenyl}-amide (example 6) | 1.1 |
| N-{4-[3-Cyclopropylmethyl-1-(2-fluoro-benzyl)-2,6-dioxo-2,3,6,7-tetrahydro-1H-purin-8-ylmethyl]-phenyl}-3-methoxy-benzenesulfonamide (example 3) | 1.2 |
| N-{4-[3-Cyclopropylmethyl-1-(2-fluoro-benzyl)-2,6-dioxo-2,3,6,7-tetrahydro-1H-purin-8-ylmethyl]-phenyl}-methanesulfonamide (example 23) | 1.25 |
| 1,3-Dimethyl-1H-pyrazole-4-sulfonic acid {4-[3-cyclopropylmethyl-1-(2-fluoro-benzyl)-2,6-dioxo-2,3,6,7-tetrahydro-1H-purin-8-ylmethyl]-phenyl}-methyl-amide (example 27) | 1.45 |
| Pyridine-3-sulfonic acid {4-[3-cyclopropylmethyl-1-(2-fluoro-benzyl)-2,6-dioxo-2,3,6,7-tetrahydro-1H-purin-8-ylmethyl]-phenyl}-amide trifluoro-acetic acid salt (example 22) | 1.95 |
| 5-Chloro-1,3-dimethyl-1H-pyrazole-4-sulfonic acid {4-[3-cyclopropylmethyl-1-(2-fluoro-benzyl)-2,6-dioxo-2,3,6,7-tetrahydro-1H-purin-8-ylmethyl]-phenyl}-methyl-amide (example 18) | 2.05 |
| 4-[3-Butyl-1-(2-fluoro-benzyl)-2,6-dioxo-2,3,6,7-tetrahydro-1H-purin-8-ylmethyl]-N-pyridin-2-yl-benzenesulfonamide (example 28) | 2.4 |
| 4-[3-Butyl-1-(2-fluoro-benzyl)-2,6-dioxo-2,3,6,7-tetrahydro-1H-purin-8-ylmethyl]-N-pyridin-4-yl-benzenesulfonamide (example 29) | 2.4 |
| N-{4-[3-Cyclopropylmethyl-1-(2-fluoro-benzyl)-2,6-dioxo-2,3,6,7-tetrahydro-1H-purin-8-ylmethyl]-phenyl}-3-fluoro-benzenesulfonamide (example 4) | 2.55 |
| 4-[3-Butyl-1-(2-fluoro-benzyl)-2,6-dioxo-2,3,6,7-tetrahydro-1H-purin-8-ylmethyl]-N-pyridin-3-yl-benzenesulfonamide (example 30) | 4.1 |
| 5-Bromo-6-chloro-pyridine-3-sulfonic acid {4-[3-cyclopropylmethyl-1-(2-fluoro-benzyl)-2,6-dioxo-2,3,6,7-tetrahydro-1H-purin-8-ylmethyl]-phenyl}-amide (example 5) | 4.58 |
| N-(4-{4-[3-Cyclopropylmethyl-1-(2-fluoro-benzyl)-2,6-dioxo-2,3,6,7-tetrahydro-1H-purin-8-ylmethyl]-phenylsulfamoyl}-phenyl)-acetamide (example 20) | 6.25 |
| 4-[3-Butyl-1-(2-fluoro-benzyl)-2,6-dioxo-2,3,6,7-tetrahydro-1H-purin-8-ylmethyl]-N-pyrimidin-2-yl-benzenesulfonamide (example 31) | 6.35 |
| 4-[3-Butyl-1-(2-fluoro-benzyl)-2,6-dioxo-2,3,6,7-tetrahydro-1H-purin-8-ylmethyl]-N-(1,3,5-trimethyl-1H-pyrazol-4-yl)-benzenesulfonamide (example 32) | 6.45 |
| N-[4-(1-Benzyl-3-butyl-2,6-dioxo-2,3,6,7-tetrahydro-1H-purin-8-ylmethyl)-phenyl]-methanesulfonamide (example 24) | 7.55 |
| N-[4-(1-Benzyl-3-butyl-2,6-dioxo-2,3,6,7-tetrahydro-1H-purin-8-ylmethyl)-phenyl]-4-methyl-benzenesulfonamide (example 21) | 7.65 |

The therapeutically effective amount of a compound in accordance with this invention can vary within wide limits and may be determined by a manner known in the art. Such dosage will be adjusted to the individual requirements in each particular case including the specific compound or compounds being administered, the route of administration, the condition being treated, as well as the patient being treated. In general, in the case of parenteral administration to adult humans weighing approximately 70 Kg, a daily dosage of about 10 mg to about 10,000 mg, preferably from about 200 mg to about 1,000 mg should be appropriate, although the upper limit may be exceeded when indicated. The daily dosage can be administered as a single dose or in divided doses, or for parental administration, it may be given as continuous infusion. Additionally, administration in the form of an elixir, tablet, capsule or suppository is envisioned and is within the scope of the present invention. The examples below are exemplary, but not limitative of, the invention.

Tablet Formulation

| Item | Ingredients | Mg/Tablet | | | | | |
|---|---|---|---|---|---|---|---|
| 1 | Compound A* | 5 | 25 | 100 | 250 | 500 | 750 |
| 2 | Anhydrous Lactose | 103 | 83 | 35 | 19 | 38 | 57 |
| 3 | Croscarmellose Sodium | 6 | 6 | 8 | 16 | 32 | 48 |
| 4 | Polyvinyl pyrrolidone K30 | 5 | 5 | 6 | 12 | 24 | 36 |
| 5 | Magnesium Stearate | 1 | 1 | 1 | 3 | 6 | 9 |
| | Total Weight | 120 | 120 | 150 | 300 | 600 | 900 |

*Compound A represents a compound of the invention.

Manufacturing Procedure:

Mix Items 1,2 and 3 in a suitable mixer for 15 minutes.

Granulate the powder mix from Step 1 with 20% Polyvinyl pyrrolidone K30 Solution (Item 4).

Dry the granulation from Step 2 at 50° C.

Pass the granulation from Step 3 through a suitable milling equipment.

Add the Item 5 to the milled granulation Step 4 and mix for 3 minutes.

Compress the granulation from Step 5 on a suitable press.

| | Capsule Formulation | | | | | |
|---|---|---|---|---|---|---|
| Item | Ingredients | | | mg/Capsule | | |
| 1 | Compound A* | 5 | 25 | 100 | 250 | 500 |
| 2 | Anhydrous Lactose | 159 | 123 | 148 | — | — |
| 3 | Corn Starch | 25 | 35 | 40 | 35 | 70 |
| 4 | Talc | 10 | 15 | 10 | 12 | 24 |
| 5 | Magnesium Stearate | 1 | 2 | 2 | 3 | 6 |
| | Total Fill Weight | 200 | 200 | 300 | 300 | 600 |

*Compound A represents a compound of the invention.

Manufacturing Procedure:

Mix Items 1, 2 and 3 in a suitable mixer for 15 minutes.

Add Items 4 & 5 and mix for 3 minutes.

Fill into a suitable capsule.

Example C

| | Injection Solution/Emulsion Preparation | |
|---|---|---|
| Item | Ingredient | mg/mL |
| 1 | Compound A* | 1 mg |
| 2 | Polyethylene glycol (MW 400) | 10–50 mg |
| 3 | Lecithin | 20–50 mg |
| 4 | Soy Oil | 1–5 mg |
| 5 | Glycerol | 8–12 mg |
| 6 | Water q.s. | 1 mL |

*Compound A represents a compound of the invention.

Manufacturing Procedure:

Dissolve item 1 in item 2.

Add item 3, 4 and 5 to item 6 and mix until dispersed, then homogenize.

Add the solution from step 1 to the mixture from step 2 and homogenize until the dispersion is translucent.

Sterile filter through a 0.2 μm filter and fill into vials.

Example D

| | Injection Solution/Emulsion Preparation | |
|---|---|---|
| Item | Ingredient | mg/mL |
| 1 | Compound A* | 1 mg |
| 2 | Glycofurol | 10–50 mg |
| 3 | Lecithin | 20–50 mg |
| 4 | Soy Oil | 1–5 mg |
| 5 | Glycerol | 8–12 mg |
| 6 | Water | q.s. 1 mL |

*Compound A represents a compound of the invention.

The invention claimed is:

1. Compounds of formula I:

wherein
- (a) $R^1$ is selected from the group consisting of:
  - (1) lower alkyl,
  - (2) lower alkyl substituted by phenyl and
  - (3) lower alkyl substituted by halogen substituted phenyl;
- (b) $R^2$ is selected from the group consisting of
  - (1) lower alkyl and
  - (2) lower alkyl substituted by lower cycloalkyl;
- (c) $R^3$ is selected from the group consisting of:

(1)

(2)

(3)

- (d) $R^4$ is selected from the group consisting of H and lower alkyl;
- (e) $R^5$ is selected from the group consisting of:
  - (1) lower alkyl,
  - (2) amino lower alkyl,
  - (3) lower alkyl substituted by phenyl,
  - (4) lower alkenyl substituted by phenyl,
  - (5) phenyl,
  - (6) phenyl substituted by at least one substituent selected from the group consisting of lower alkyl, lower alkyl substituted by halogen, halogen, lower alkoxy, lower alkoxy substituted by halogen, nitro and acetamido,
  - (7) a 5-membered heteroaromatic ring having one heteroatom independently selected from the group consisting of N, O and S, the 5-membered heteroaromatic ring being unsubstituted or substituted by at least one substituent selected from the group consisting of lower alkyl, halogen, carboxy lower alkyl, amino, alkyl amino and acetamido,
  - (8) a 5-membered heteroaromatic ring having two heteroatoms wherein a first heteroatom is N and a second heteroatom is independently selected from the group consisting of N, O and S, the 5-membered heteroaromatic ring being unsubstituted or substituted by at least one substituent selected from the group consisting of lower alkyl, halogen, carboxy lower alkyl, amino, alkyl amino and acetamido, (9) a 6-membered heteroaromatic ring having one N, the 6-membered heteroaromatic ring being unsubstituted or substituted by at least one substituent selected from the group consisting of lower alkyl, halogen, carboxy lower alkyl, amino, alkyl amino and acetamido,

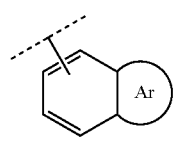

(10)

wherein Ar is selected from the group consisting of:
(A) a 5-membered heteroaromatic ring fused to the 6-membered ring, having one, two, or three heteroatoms, and wherein a first heteroatom is N, a second heteroatom is N and a third heteroatom is selected from the group consisting of O and S,
(B) a 6-membered aromatic ring fused to the 6-membered ring, having no or one N heteroatoms, the fused 6-membered aromatic ring being unsubstituted or substituted by at least one substituent selected from the group consisting of lower alkyl, halogen, carboxy lower alkyl, amino, alkyl amino and acetamido; and (f) $R^6$ is selected from the group consisting of:
(1) H,
(2) a 5-membered aromatic heterocyclic ring with one or two heteroatoms wherein a first heteroatom is N and a second heteroatom is selected from the group consisting of N and S, the 5-membered heterocyclic ring being unsubstituted or substituted by at least one substituent selected from the group consisting of lower alkyl, halogen, carboxy lower alkyl, amino, alkyl amino and acetamido, and
(3) a 6-membered aromatic heterocyclic ring with one or two N heteroatoms, the 6-membered heterocyclic ring being unsubstituted or substituted by at least one substituent selected from the group consisting of lower alkyl, halogen, carboxy lower alkyl, amino, alkyl amino and acetamido;

or pharmaceutically acceptable salt or prodrug thereof.

2. The compounds of formula I according to claim 1 wherein $R^1$ is lower alkyl.

3. The compounds of formula I according to claim 2 wherein $R^2$ is lower alkyl.

4. A compounds of claim 1 selected from the group consisting of:
1,3-dimethyl-1H-pyrazole-4-sulfonic acid [4-(1,3-dimethyl-2,6-dioxo-2,3,6,7-tetrahydro-1H-purin-8-ylmethyl)-phenyl]-amide; and
5-chloro-1,3-dimethyl-1H-pyrazole-4-sulfonic acid {4-[1,3-dimethyl-2,6-dioxo-2,3,6,7-tetrahydro-1H-purin-8-ylmethyl]-phenyl}-amide.

5. The compounds of formula I according to claim 1 wherein $R^1$ is lower alkyl substituted by phenyl.

6. The compounds of formula I according to claim 5 wherein $R^2$ is lower alkyl.

7. A compounds of claim 1 wherein the compound is selected from the group consisting of:
4-(1-benzyl-3-butyl-2,6-dioxo-2,3,6,7-tetrahydro-1H-purin-8-ylmethyl)-benzenesulfonamide;
N-[4-(1-benzyl-3-butyl-2,6-dioxo-2,3,6,7-tetrahydro-1H-purin-8-ylmethyl)-phenyl]-4-methyl-benzenesulfonamide; and
N-[4-(1-benzyl-3-butyl-2,6-dioxo-2,3,6,7-tetrahydro-1H-purin-8-ylmethyl)-phenyl]-methanesulfonamide.

8. The compounds of formula I according to claim 1 having the formula:

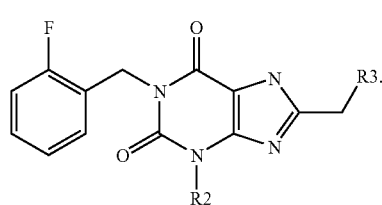

IA

9. The compounds of formula IA according to claim 8 wherein $R^2$ is lower alkyl.

10. The compounds of formula IA according to claim 9 wherein $R^2$ is n-butyl.

11. The compounds of formula IA according to claim 10 wherein: $R^3$ is

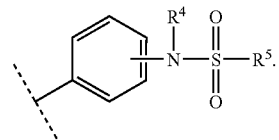

12. The compounds of formula IA according to claim 11 wherein $R^4$ is H.

13. The compounds of formula IA according to claim 12 wherein $R^5$ is a 5-membered heteroaromatic ring having one heteroatom independently selected from the group consisting of N, O and S, the 5-membered heteroaromatic ring being unsubstituted or substituted by at least one substituent selected from the group consisting of lower alkyl, halogen, carboxy lower alkyl, amino, alkyl amino and acetamido.

14. A compounds of claim 1 selected from the group consisting of:
thiophene-2-sulfonic acid {4-[3-butyl-1-(2-fluoro-benzyl)-2,6-dioxo-2,3,6,7-tetrahydro-1H-purin-8-ylmethyl]-phenyl}-amide;
5-chlorothiophene-2-sulfonic acid {4-[3-butyl-1-(2-fluoro-benzyl)-2,6-dioxo-2,3,6,7-tetrahydro-1H-purin-8-ylmethyl]-phenyl}-amide;
3-{4-[3-butyl-1-(2-fluoro-benzyl)-2,6-dioxo-2,3,6,7-tetrahydro-1H-purin-8-ylmethyl]-phenylsulfamoyl}-thiophene-2-carboxylic acid methyl ester;
4,5-dibromothiophene-2-sulfonic acid {4-[3-butyl-1-(2-fluoro-benzyl)-2,6-dioxo-2,3,6,7-tetrahydro-1H-purin-8-ylmethyl]-phenyl}-amide; and
5-bromo-thiophene-2-sulfonic acid {4-[3-butyl-1-(2-fluoro-benzyl)-2,6-dioxo-2,3,6,7-tetrahydro-1H-purin-8-ylmethyl]-phenyl}-amide.

15. The compounds of formula IA according to claim 12 wherein $R^5$ is a 5-membered heteroaromatic ring having two heteroatoms wherein a first heteroatom is N and a second heteroatom is independently selected from the group consisting of N, O and S, the 5-membered heteroaromatic ring being unsubstituted or substituted by at least one substituent selected from the group consisting of lower alkyl, halogen, carboxy lower alkyl, amino, alkyl amino and acetamido.

16. A compound of claim 1 wherein the compound is selected from the group consisting of:
 1-Methyl-1H-imidazole-4-sulfonic acid {4-[3-butyl-1-(2-fluoro-benzyl)-2,6-dioxo-2,3,6,7-tetrahydro-1H-purin-8-ylmethyl]-phenyl}-amide trifluoroacetic acid salt; and
 5-chloro-1,3-dimethyl-1H-pyrazole-4-sulfonic acid {4-[3-butyl-1-(2-fluoro-benzyl)-2,6-dioxo-2,3,6,7-tetrahydro-1H-purin-8-ylmethyl]-phenyl}-amide.

17. The compounds of formula IA according to claim 12 wherein $R^5$ is a 6-membered heteroaromatic ring having one N, the 6-membered heteroaromatic ring being unsubstituted or substituted by at least one substituent selected from the group consisting of lower alkyl, halogen, carboxy lower alkyl, amino, alkyl amino and acetamido.

18. A compound of claim 1 wherein the compound is 6-chloro-pyridine-3-sulfonic acid {4-[3-butyl-1-(2-fluoro-benzyl)-2,6-dioxo-2,3,6,7-tetrahydro-1H-purin-8-ylmethyl]-phenyl}-amide.

19. The compounds of formula IA according to claim 12 wherein $R^5$ is:

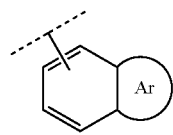

(10)

where Ar is selected from the group consisting of:
 (A) a 5-membered heteroaromatic ring fused to the 6-membered ring, having one, two, or three heteroatoms, and wherein a first heteroatom is N, a second heteroatom is N and a third heteroatom is selected from the group consisting of O and S, and
 (B) a 6-membered aromatic ring fused to the 6-membered ring, having no or one N heteroatoms, the fused 6-membered aromatic ring being unsubstituted or substituted by at least one substituent selected from the group consisting of lower alkyl, halogen, carboxy lower alkyl, amino, alkyl amino and acetamido.

20. A compound selected from the group consisting of:
 N-{4-[3-butyl-1-(2-fluoro-benzyl)-2,6-dioxo-2,3,6,7-tetrahydro-1H-purin-8-ylmethyl]-phenyl}-1-naphthalenesulfonamide;
 5-dimethylamino-naphthalene-1-sulfonic acid {4-[3-butyl-1-(2-fluoro-benzyl)-2,6-dioxo-2,3,6,7-tetrahydro-1H-purin-8-ylmethyl]-phenyl}-amide;
 benzo[1,2,5]thiadiazole-4-sulfonic acid {4-[3-butyl-1-(2-fluoro-benzyl)-2,6-dioxo-2,3,6,7-tetrahydro-1H-purin-8-ylmethyl]-phenyl}-amide; and
 benzo[1,2,5]oxadiazole-4-sulfonic acid {4-[3-butyl-1-(2-fluoro-benzyl)-2,6-dioxo-2,3,6,7-tetrahydro-1H-purin-8-ylmethyl]-phenyl}-amide.

21. The compounds of formula IA according to claim 12 wherein $R^5$ is lower alkyl or lower alkyl substituted by phenyl.

22. A compound of claim 1 wherein the compound is selected from the group consisting of:
 propane-2-sulfonic acid {4-[3-butyl-1-(2-fluoro-benzyl)-2,6-dioxo-2,3,6,7-tetrahydro-1H-purin-8-ylmethyl]-phenyl}-amide;
 N-{4-[3-butyl-1-(2-fluoro-benzyl)-2,6-dioxo-2,3,6,7-tetrahydro-1H-purin-8-ylmethyl]-phenyl}-C-phenyl-methanesulfonamide; and
 ethanesulfonic acid {4-[3-butyl-1-(2-fluoro-benzyl)-2,6-dioxo-2,3,6,7-tetrahydro-1H-purin-8-ylmethyl]-phenyl}-amide.

23. The compounds of formula IA according to claim 12 wherein $R^5$ is lower alkenyl substituted by phenyl.

24. A compound of claim 1 wherein the compound is 2-phenyl-ethenesulfonic acid {4-[3-butyl-1-(2-fluoro-benzyl)-2,6-dioxo-2,3,6,7-tetrahydro-1H-purin-8-ylmethyl]-phenyl}-amide.

25. The compounds of formula IA according to claim 12 wherein $R^5$ is phenyl.

26. A compound of claim 1 wherein the compound is N-{4-[3-butyl-1-(2-fluoro-benzyl)-2,6-dioxo-2,3,6,7-tetrahydro-1H-purin-8-ylmethyl]-phenyl}-benzenesulfonamide.

27. The compounds of formula IA according to claim 12 wherein $R^5$ is phenyl substituted by at least one substituent selected from the group consisting of lower alkyl, lower alkyl substituted by halogen, halogen, lower alkoxy, lower alkoxy substituted by halogen, nitro and acetamido.

28. The compounds of claim 27 wherein the phenyl group has one substituent selected from the group consisting of lower alkyl, lower alkyl substituted by halogen, halogen, lower alkoxy, lower alkoxy substituted by halogen, nitro and acetamido.

29. The compounds of formula IA according to claim 28 wherein the one substituent is halogen.

30. A compound of claim 1 wherein the compound is selected from the group consisting of:
 N-{4-[3-butyl-1-(2-fluoro-benzyl)-2,6-dioxo-2,3,6,7-tetrahydro-1H-purin-8-ylmethyl]-phenyl}-4-chloro-benzenesulfonamide;
 N-{4-[3-butyl-1-(2-fluoro-benzyl)-2,6-dioxo-2,3,6,7-tetrahydro-1H-purin-8-ylmethyl]-phenyl}-4-iodo-benzenesulfonamide;
 N-{4-[3-butyl-1-(2-fluoro-benzyl)-2,6-dioxo-2,3,6,7-tetrahydro-1H-purin-8-ylmethyl]-phenyl}-2-chloro-benzenesulfonamide;
 N-{4-[3-butyl-1-(2-fluoro-benzyl)-2,6-dioxo-2,3,6,7-tetrahydro-1H-purin-8-ylmethyl]-phenyl}-3-chloro-benzenesulfonamide;
 N-{4-[3-butyl-1-(2-fluoro-benzyl)-2,6-dioxo-2,3,6,7-tetrahydro-1H-purin-8-ylmethyl]-phenyl}-4-fluoro-benzenesulfonamide;
 N-{4-[3-butyl-1-(2-fluoro-benzyl)-2,6-dioxo-2,3,6,7-tetrahydro-1H-purin-8-ylmethyl]-phenyl}-2-fluoro-benzenesulfonamide; and
 N-{4-[3-butyl-1-(2-fluoro-benzyl)-2,6-dioxo-2,3,6,7-tetrahydro-1H-purin-8-ylmethyl]-phenyl}-4-bromo-benzenesulfonamide.

31. The compounds of formula IA according to claim 28 wherein the one substituent is lower alkyl or lower alkyl substituted by halogen.

32. A compound of claim 1 wherein the compound is selected from the group consisting of:
 N-{4-[3-butyl-1-(2-fluoro-benzyl)-2,6-dioxo-2,3,6,7-tetrahydro-1H-purin-8-ylmethyl]-phenyl}-3-trifluoromethyl-benzenesulfonamide;
 N-{4-[3-butyl-1-(2-fluoro-benzyl)-2,6-dioxo-2,3,6,7-tetrahydro-1H-purin-8-ylmethyl]-phenyl}-4-isopropyl-benzenesulfonamide;

N-{4-[3-butyl-1-(2-fluoro-benzyl)-2,6-dioxo-2,3,6,7-tetrahydro-1H-purin-8-ylmethyl]-phenyl}-3-methyl-benzenesulfonamide;

N-{4-[3-butyl-1-(2-fluoro-benzyl)-2,6-dioxo-2,3,6,7-tetrahydro-1H-purin-8-ylmethyl]-phenyl}-2-trifluoromethyl-benzenesulfonamide;

N-{4-[3-butyl-1-(2-fluoro-benzyl)-2,6-dioxo-2,3,6,7-tetrahydro-1H-purin-8-ylmethyl]-phenyl}-4-ethyl-benzenesulfonamide;

N-{4-[3-butyl-1-(2-fluoro-benzyl)-2,6-dioxo-2,3,6,7-tetrahydro-1H-purin-8-ylmethyl]-phenyl}-2-methyl-benzenesulfonamide; and N-{4-[3-butyl-1-(2-fluoro-benzyl)-2,6-dioxo-2,3,6,7-tetrahydro-1H-purin-8-ylmethyl]-phenyl}-4-trifluoromethyl-benzenesulfonamide.

33. A compound of formula IA according to claim 28 wherein the one substituent is selected from the group consisting of nitro, alkoxy and alkoxy substituted by halogen.

34. A compound of claim 1 wherein the compound is selected from the group consisting of:
N-{4-[3-butyl-1-(2-fluoro-benzyl)-2,6-dioxo-2,3,6,7-tetrahydro-1H-purin-8-ylmethyl]-phenyl}-4-trifluoromethyl-benzenesulfonamide,
N-{4-[3-butyl-1-(2-fluoro-benzyl)-2,6-dioxo-2,3,6,7-tetrahydro-1H-purin-8-ylmethyl]-phenyl}-3-nitro-benzenesulfonamide,
N-{4-[3-butyl-1-(2-fluoro-benzyl)-2,6-dioxo-2,3,6,7-tetrahydro-1H-purin-8-ylmethyl]-phenyl}-4-methoxy-benzenesulfonamide, and
N-{4-[3-butyl-1-(2-fluoro-benzyl)-2,6-dioxo-2,3,6,7-tetrahydro-1H-purin-8-ylmethyl]-phenyl}-4-trifluoromethoxy-benzenesulfonamide.

35. The compounds of formula IA according to claim 27 wherein the phenyl group has two substituents selected from the group consisting of lower alkyl, lower alkyl substituted by halogen, halogen, lower alkoxy, lower alkoxy substituted by halogen, nitro and acetamido.

36. The compounds of formula IA according to claim 35 wherein the two substituents are each halogen.

37. The compounds of formula IA according to claim 36 wherein the halogen substituents are chloro.

38. A compound of claim 1 wherein the compound is selected from the group consisting of:
N-{4-[3-butyl-1-(2-fluoro-benzyl)-2,6-dioxo-2,3,6,7-tetrahydro-1H-purin-8-ylmethyl]-phenyl}-2,4-dichloro-benzenesulfonamide;
N-{4-[3-butyl-1-(2-fluoro-benzyl)-2,6-dioxo-2,3,6,7-tetrahydro-1H-purin-8-ylmethyl]-phenyl}-2,5-dichloro-benzenesulfonamide;
N-{4-[3-butyl-1-(2-fluoro-benzyl)-2,6-dioxo-2,3,6,7-tetrahydro-1H-purin-8-ylmethyl]-phenyl}-2,6-dichloro-benzenesulfonamide;
N-{4-[3-butyl-1-(2-fluoro-benzyl)-2,6-dioxo-2,3,6,7-tetrahydro-1H-purin-8-ylmethyl]-phenyl}-2,3-dichloro-benzenesulfonamide;
N-{4-[3-butyl-1-(2-fluoro-benzyl)-2,6-dioxo-2,3,6,7-tetrahydro-1H-purin-8-ylmethyl]-phenyl}-3,5-dichloro-benzenesulfonamide; and
N-{4-[3-butyl-1-(2-fluoro-benzyl)-2,6-dioxo-2,3,6,7-tetrahydro-1H-purin-8-ylmethyl]-phenyl}-3,4-dichloro-benzenesulfonamide.

39. The compounds of formula IA according to claim 36 wherein one of the halogen substituents is chloro and the other of the halogen substituents is fluoro.

40. A compound of claim 1 wherein the compound is selected from the group consisting of:

N-{4-[3-Butyl-1-(2-fluoro-benzyl)-2,6-dioxo-2,3,6,7-tetrahydro-1H-purin-8-ylmethyl]-phenyl}-2-chloro-4-fluoro-benzenesulfonamide; and N-{4-[3-butyl-1-(2-fluoro-benzyl)-2,6-dioxo-2,3,6,7-tetrahydro-1H-purin-8-ylmethyl]-phenyl}-3-chloro-4-fluoro-benzenesulfonamide.

41. The compounds of formula IA according to claim 36 wherein the two halogen substituents are fluoro.

42. A compound of claim 1 selected from the group consisting of:
N-{4-[3-butyl-1-(2-fluoro-benzyl)-2,6-dioxo-2,3,6,7-tetrahydro-1H-purin-8-ylmethyl]-phenyl}-2,4-difluoro-benzenesulfonamide;
N-{4-[3-butyl-1-(2-fluoro-benzyl)-2,6-dioxo-2,3,6,7-tetrahydro-1H-purin-8-ylmethyl]-phenyl}-2,6-difluoro-benzenesulfonamide; and
N-{4-[3-butyl-1-(2-fluoro-benzyl)-2,6-dioxo-2,3,6,7-tetrahydro-1H-purin-8-ylmethyl]-phenyl}-3,4-difluoro-benzenesulfonamide.

43. The compounds of formula IA according to claim 35 wherein one of the substituents is halogen and the other of the substituents is lower alkyl.

44. A compound of claim 1 selected from the group consisting of:
N-{4-[3-butyl-1-(2-fluoro-benzyl)-2,6-dioxo-2,3,6,7-tetrahydro-1H-purin-8-ylmethyl]-phenyl}-3-chloro-4-methyl-benzenesulfonamide;
N-{4-[3-butyl-1-(2-fluoro-benzyl)-2,6-dioxo-2,3,6,7-tetrahydro-1H-purin-8-ylmethyl]-phenyl}-3-chloro-2-methyl-benzenesulfonamide;
N-{4-[3-butyl-1-(2-fluoro-benzyl)-2,6-dioxo-2,3,6,7-tetrahydro-1H-purin-8-ylmethyl]-phenyl}-2-chloro-6-methyl-benzenesulfonamide; and
N-{4-[3-butyl-1-(2-fluoro-benzyl)-2,6-dioxo-2,3,6,7-tetrahydro-1H-purin-8-ylmethyl]-phenyl}-5-fluoro-2-methyl-benzenesulfonamide.

45. The compounds of formula IA according to claim 35 wherein the two substituents are selected from the group consisting of lower alkyl, lower alkoxyl and nitro.

46. A compound of claim 1 selected from the group consisting of:
N-{4-[3-butyl-1-(2-fluoro-benzyl)-2,6-dioxo-2,3,6,7-tetrahydro-1H-purin-8-ylmethyl]-phenyl}-2,5-dimethoxy-benzenesulfonamide;
N-{4-[3-butyl-1-(2-fluoro-benzyl)-2,6-dioxo-2,3,6,7-tetrahydro-1H-purin-8-ylmethyl]-phenyl}-2-methoxy-5-methyl-benzenesulfonamide;
N-{4-[3-butyl-1-(2-fluoro-benzyl)-2,6-dioxo-2,3,6,7-tetrahydro-1H-purin-8-ylmethyl]-phenyl}-3,4-dimethoxy-benzenesulfonamide;
N-{4-[3-butyl-1-(2-fluoro-benzyl)-2,6-dioxo-2,3,6,7-tetrahydro-1H-purin-8-ylmethyl]-phenyl}-2,5-dimethyl-benzenesulfonamide; and
N-{4-[3-Butyl-1-(2-fluoro-benzyl)-2,6-dioxo-2,3,6,7-tetrahydro-1H-purin-8-ylmethyl]-phenyl}-2-methyl-5-nitro-benzenesulfonamide.

47. The compounds of formula IA according to claim 27 wherein the phenyl group has three substituents selected from the group consisting of lower alkyl, lower alkyl substituted by halogen, halogen, lower alkoxy, lower alkoxy substituted by halogen, nitro and acetamido.

48. The compounds of formula IA according to claim 47 wherein the three substituents are selected from lower alkyl and halogen.

49. A compound of claim 1 wherein the compound is selected from the group consisting of:

N-{4-[3-butyl-1-(2-fluoro-benzyl)-2,6-dioxo-2,3,6,7-tetrahydro-1H-purin-8-ylmethyl]-phenyl}-2,4,6-trimethyl-benzenesulfonamide;

N-{4-[3-butyl-1-(2-fluoro-benzyl)-2,6-dioxo-2,3,6,7-tetrahydro-1H-purin-8-ylmethyl]-phenyl}-4-chloro-2,5-dimethyl-benzenesulfonamide, N-{4-[3-butyl-1-(2-fluoro-benzyl)-2,6-dioxo-2,3,6,7-tetrahydro-1H-purin-8-ylmethyl]-phenyl}-2,4-dichloro-6-methyl-benzenesulfonamide; and N-{4-[3-butyl-1-(2-fluoro-benzyl)-2,6-dioxo-2,3,6,7-tetrahydro-1H-purin-8-ylmethyl]-phenyl}-C-phenyl-methanesulfonamide.

50. The compounds of formula IA according to claim 27 wherein the phenyl group has four substituents selected from the group consisting of lower alkyl, lower alkyl substituted by halogen, halogen, lower alkoxy, lower alkoxy substituted by halogen, nitro and acetamido.

51. The compounds of formula IA according to claim 50 wherein the four substituents are selected from the group consisting of lower alkyl and lower alkoxy.

52. A compound of claim 1 selected from the group consisting of:
N-{4-[3-butyl-1-(2-fluoro-benzyl)-2,6-dioxo-2,3,6,7-tetrahydro-1H-purin-8-ylmethyl]-phenyl}-2,3,5,6-tetramethyl-benzenesulfonamide; and
N-{4-[3-butyl-1-(2-fluoro-benzyl)-2,6-dioxo-2,3,6,7-tetrahydro-1H-purin-8-ylmethyl]-phenyl}-4-methoxy-2,3,6-trimethyl-benzenesulfonamide.

53. The compounds of formula IA according to claim 10 wherein $R^3$ is:

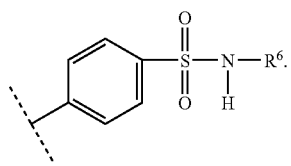

54. The compounds of formula IA according to claim 53 wherein $R^6$ is a 5-membered aromatic heterocyclic ring with one or two heteroatoms wherein a first heteroatom is N and a second heteroatom is selected from the group consisting of N and S; the 5-membered heterocyclic ring being unsubstituted or substituted by at least one substituent selected from the group consisting of lower alkyl, halogen, carboxy lower alkyl, amino, alkyl amino and acetamido.

55. A compound of claim 1 wherein the compound is selected from the group consisting of:
4-[3-butyl-1-(2-fluoro-benzyl)-2,6-dioxo-2,3,6,7-tetrahydro-1H-purin-8-ylmethyl]-N-(1,3,5-trimethyl-1H-pyrazol-4-yl)-benzenesulfonamide; and
4-[3-butyl-1-(2-fluoro-benzyl)-2,6-dioxo-2,3,6,7-tetrahydro-1H-purin-8-ylmethyl]-N-thiazol-2-yl-benzenesulfonamide.

56. The compounds of formula IA according to claim 53 wherein $R^6$ is a 6-membered aromatic heterocyclic ring with one or two N heteroatoms, the 6-membered heterocyclic ring being unsubstituted or substituted by at least one substituent selected from the group consisting of lower alkyl, halogen, carboxy lower alkyl, amino, alkyl amino and acetamido.

57. A compound of claim 1 wherein the compound is selected from the group consisting of:
4-[3-butyl-1-(2-fluoro-benzyl)-2,6-dioxo-2,3,6,7-tetrahydro-1H-purin-8-ylmethyl]-N-pyridin-2-yl-benzenesulfonamide;

4-[3-butyl-1-(2-fluoro-benzyl)-2,6-dioxo-2,3,6,7-tetrahydro-1H-purin-8-ylmethyl]-N-pyridin-3-yl-benzenesulfonamide;

4-[3-butyl-1-(2-fluoro-benzyl)-2,6-dioxo-2,3,6,7-tetrahydro-1H-purin-8-ylmethyl]-N-pyridin-4-yl-benzenesulfonamide;

4-[3-butyl-1-(2-fluoro-benzyl)-2,6-dioxo-2,3,6,7-tetrahydro-1H-purin-8-ylmethyl]-N-pyrimidin-2-yl-benzenesulfonamide; and 4-[3-butyl-1-(2-fluoro-benzyl)-2,6-dioxo-2,3,6,7-tetrahydro-1H-purin-8-ylmethyl]-N-(1,3,5-trimethyl-1H-pyrazol-4-yl)-benzenesulfonamide.

58. The compounds of formula IA according to claim 10 wherein $R^3$ is:

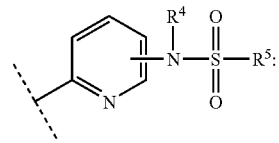

$R^4$ is H; and $R^5$ is a 5-membered aromatic heterocyclic ring with one or two heteroatoms wherein a first heteroatom is N and a second heteroatom is selected from the group consisting of N and S, the 5-membered heterocyclic ring being unsubstituted or substituted by at least one substituent selected from the group consisting of lower alkyl, halogen, carboxy lower alkyl, amino, alkyl amino and acetamido.

59. A compound of claim 1 wherein the compound is 5-chloro-1,3-dimethyl-1H-pyrazole-4-sulfonic acid {6-[3-cyclobutylmethyl-1-(2-fluoro-benzyl)-2,6-dioxo-2,3,6,7-tetrahydro-1H-purin-8-ylmethyl]-pyridin-3-yl}-amide.

60. The compounds of formula IA according to claim 8 wherein $R^2$ is lower alkyl substituted by cyclobutyl and $R^3$ is:

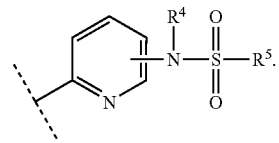

61. A compound of claim 1 wherein the compound is 5-chloro-1,3-dimethyl-1H-pyrazole-4-sulfonic acid {6-[3-cyclobutylmethyl-1-(2-fluoro-benzyl)-2,6-dioxo-2,3,6,7-tetrahydro-1H-purin-8-ylmethyl]-pyridin-3-yl}-amide.

62. The compounds of formula 1 according to claim 8 with the formula:

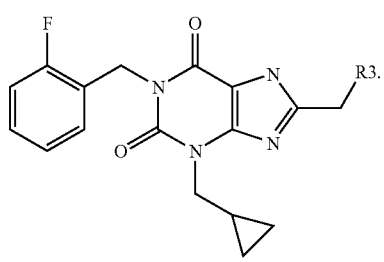

63. The compounds of formula IB according to claim 62 wherein $R^3$ is:

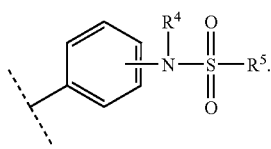

64. The compounds of formula IB according to claim 63 wherein $R^4$ is H.

65. The compounds of formula IB according to claim 64 wherein $R^5$ is a 5-membered heteroaromatic ring having two heteroatoms wherein a first heteroatom is N and a second heteroatom is independently selected from the group consisting of N, O and S, the 5-membered heteroaromatic ring being unsubstituted or substituted by at least one substituent selected from the group consisting of lower alkyl, halogen, carboxy lower alkyl, amino, alkyl amino and acetamido.

66. The compounds of formula IB according to claim 65 wherein the 5-membered heteroaromatic ring has two lower alkyl substituents.

67. A compound of claim 1 wherein the compound is selected from the group consisting of:
   1,2-dimethyl-1H-imidazole-4-sulfonic acid {4-[3-cyclopropylmethyl-1-(2-fluoro-benzyl)-2,6-dioxo-2,3,6,7-tetrahydro-1H-purin-8-ylmethyl]-phenyl}-amide;
   3,5-dimethyl-isoxazole-4-sulfonic acid {4-[3-cyclopropylmethyl-1-(2-fluoro-benzyl)-2,6-dioxo-2,3,6,7-tetrahydro-1H-purin-8-ylmethyl]-phenyl}-amide; and
   1,3-dimethyl-1H-pyrazole-4-sulfonic acid {4-[3-cyclopropylmethyl-1-(2-fluoro-benzyl)-2,6-dioxo-2,3,6,7-tetrahydro-1H-purin-8-ylmethyl]-phenyl}-amide.

68. A compound of claim 1 wherein the compound is 1,2-dimethyl-1H-imidazole-4-sulfonic acid {4-[3-cyclopropylmethyl-1-(2-fluoro-benzyl)-2,6-dioxo-2,3,6,7-tetrahydro-1H-purin-8-ylmethyl]-phenyl}-amide.

69. A compound of claim 1 wherein the compound is 3,5-dimethyl-isoxazole-4-sulfonic acid {4-[3-cyclopropylmethyl-1-(2-fluoro-benzyl)-2,6-dioxo-2,3,6,7-tetrahydro-1H-purin-8-ylmethyl]-phenyl}-amide.

70. A compound of claim 1 wherein the compound is 1,3-dimethyl-1H-pyrazole-4-sulfonic acid {4-[3-cyclopropylmethyl-1-(2-fluoro-benzyl)-2,6-dioxo-2,3,6,7-tetrahydro-1H-purin-8-ylmethyl]-phenyl}-amide.

71. The compounds of formula IB according to claim 65 wherein the 5-membered heteroaromatic ring has one lower alkyl substituent.

72. A compound of claim 1 wherein the compound is selected from the group consisting of:
   1-methyl-1H-pyrazole-4-sulfonic acid {4-[3-cyclopropylmethyl-1-(2-fluoro-benzyl)-2,6-dioxo-2,3,6,7-tetrahydro-1H-purin-8-ylmethyl]-phenyl}-amide, and
   1-methyl-1H-imidazole-4-sulfonic acid {4-[3-cyclopropylmethyl-1-(2-fluoro-benzyl)-2,6-dioxo-2,3,6,7-tetrahydro-1H-purin-8-ylmethyl]-phenyl}-amide.

73. The compounds of formula IB according to claim 65 wherein the 5-membered heteroaromatic ring has one lower alkyl substituent and one amino substituent.

74. A compound of claim 1 wherein the compound is 2-amino-4-methyl-thiazole-5-sulfonic acid {4-[3-cyclopropylmethyl-1-(2-fluoro-benzyl)-2,6-dioxo-2,3,6,7-tetrahydro-1H-purin-8-ylmethyl]-phenyl}-amide trifluoro-acetic acid salt.

75. The compounds of formula IB according to claim 65 wherein the 5-membered heteroaromatic ring has one lower alkyl substituent and one acetamido substituent.

76. A compound of claim 1 wherein the compound is N-(5-{4-[3-cyclopropylmethyl-1-(2-fluoro-benzyl)-2,6-dioxo-2,3,6,7-tetrahydro-1H-purin-8-ylmethyl]-phenylsulfamoyl}-4-methyl-thiazol-2-yl)-acetamide.

77. The compounds of formula IB according to claim 65 wherein the 5-membered heteroaromatic ring has one lower alkyl substituent and one halogen substituent.

78. A compound of claim 1 wherein the compound is 5-chloro-1,3-dimethyl-1H-pyrazole-4-sulfonic acid {4-[3-cyclopropylmethyl-1-(2-fluoro-benzyl)-2,6-dioxo-2,3,6,7-tetrahydro-1H-purin-8-ylmethyl]-phenyl}-amide.

79. The compounds of formula IB according to claim 65 wherein the 5-membered heteroaromatic ring has three substituents.

80. A compound of claim 1 wherein the compound is 5-chloro-1,3-dimethyl-1H-pyrazole-4-sulfonic acid {3-[3-cyclopropylmethyl-1-(2-fluoro-benzyl)-2,6-dioxo-2,3,6,7-tetrahydro-1H-purin-8-ylmethyl]-phenyl}-amide.

81. The compounds of formula IB according to claim 64 wherein $R^5$ is phenyl substituted by at least one substituent selected from the group consisting of lower alkyl, lower alkyl substituted by halogen, halogen, lower alkoxy, lower alkoxy substituted by halogen, nitro and acetamido.

82. The compounds of formula IB according to claim 81 wherein the phenyl group is substituted by one halogen.

83. A compound of claim 1 wherein the compound is N-{4-[3-cyclopropylmethyl-1-(2-fluoro-benzyl)-2,6-dioxo-2,3,6,7-tetrahydro-1H-purin-8-ylmethyl]-phenyl}-3-fluoro-benzenesulfonamide.

84. The compounds of formula IB according to claim 81 wherein the phenyl is substituted by one alkoxy.

85. A compound of claim 1 wherein the compound is N-{4-[3-cyclopropylmethyl-1-(2-fluoro-benzyl)-2,6-dioxo-2,3,6,7-tetrahydro-1H-purin-8-ylmethyl]-phenyl}-3-methoxy-benzenesulfonamide.

86. The compounds of formula IB according to claim 81 wherein the phenyl is substituted by one acetamido.

87. A compound of claim 1 wherein the compound is N-(4-{4-[3-cyclopropylmethyl-1-(2-fluoro-benzyl)-2,6-dioxo-2,3,6,7-tetrahydro-1H-purin-8-ylmethyl]-phenylsulfamoyl}-phenyl)-acetamide.

88. The compounds of formula IB according to claim 64 wherein $R^5$ is a 6-membered heteroaromatic ring having one N, the 6-membered heteroaromatic ring being unsubstituted or substituted by at least one substituent selected from the group consisting of lower alkyl, halogen, carboxy lower alkyl, amino, alkyl amino and acetamido.

89. The compounds of formula IB according to claim 88 wherein the heteroaromatic ring is unsubstituted.

90. A compound of claim 1 wherein the compound is pyridine-3-sulfonic acid {4-[3-cyclopropylmethyl-1-(2-fluoro-benzyl)-2,6-dioxo-2,3,6,7-tetrahydro-1H-purin-8-ylmethyl]-phenyl}-amide trifluoro-acetic acid salt.

91. The compounds of formula IB according to claim 88 wherein the 6-membered heteroaromatic ring has one substituent.

92. The compounds of formula IB according to claim 88 wherein 6-membered heteroaromatic ring is substituted by two halogen substituents.

93. A compound of claim 1 wherein the compound is 5-bromo-6-chloro-pyridine-3-sulfonic acid {4-[3-cyclopropylmethyl-1-(2-fluoro-benzyl)-2,6-dioxo-2,3,6,7-tetrahydro-1H-purin-8-ylmethyl]-phenyl}-amide.

94. The compounds of formula IB according to claim 64 wherein $R^5$ is lower alkyl.

95. A compound of claim 1 wherein the compound is N-{4-[3-cyclopropylmethyl-1-(2-fluoro-benzyl)-2,6-dioxo-2,3,6,7-tetrahydro-1H-purin-8-ylmethyl]-phenyl}-methane-sulfonamide.

96. The compounds of formula IB according to claim 64 wherein $R^5$ is amino lower alkyl.

97. N-'{4-[3-cyclopropylmethyl-1-(2-fluoro-benzyl)-2,6-dioxo-2,3,6,7-tetrahydro-1H-purin-8-ylmethyl]-phenyl}-N,N-dimethylsulfamide.

98. The compounds of formula IB according to claim 64 wherein $R^5$ is:

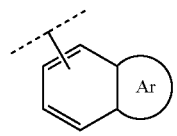

wherein Ar is selected from the group consisting of a 5-membered heteroaromatic ring fused to the 6-membered ring, having one, two, or three heteroatoms, and wherein a first heteroatom is N, a second heteroatom is N and a third heteroatom is selected from the group consisting of O and S; the 5-membered heteroaromatic ring being unsubstituted or substituted by at least one substituent selected from the group consisting of lower alkyl, halogen, carboxy lower alkyl, amino, alkyl amino and acetamido.

99. A compound of claim 1 wherein the compound is quinoline-8-sulfonic acid {4-[3-cyclopropylmethyl-1-(2-fluoro-benzyl)-2,6-dioxo-2,3,6,7-tetrahydro-1H-purin-8-ylmethyl]-phenyl}-amide.

100. The compounds of formula IB according to claim 63 wherein $R^4$ is lower alkyl.

101. A compound of claim 1 wherein the compound is selected from the group consisting of:

1,3-dimethyl-1H-pyrazole-4-sulfonic acid {4-[3-cyclopropylmethyl-1-(2-fluoro-benzyl)-2,6-dioxo-2,3,6,7-tetrahydro-1H-purin-8-ylmethyl]-phenyl}-methyl-amide; and 5-chloro-1,3-dimethyl-1H-pyrazole-4-sulfonic acid {4-[3-cyclopropylmethyl-1-(2-fluoro-benzyl)-2,6-dioxo-2,3,6,7-tetrahydro-1H-purin-8-ylmethyl]-phenyl}-methyl-amide.

102. A pharmaceutical composition comprising a compounds of formula I according to claim 1 or a pharmaceutically acceptable salt or prodrug thereof, and a pharmaceutically acceptable excipient.

103. A method of treatment for type 2 diabetes comprising administering a therapeutically effective amount of a compound of formula I according to claim 1 or a pharmaceutically acceptable salt or prodrug thereof, to a patient in need of such treatment.

* * * * *

UNITED STATES PATENT AND TRADEMARK OFFICE
CERTIFICATE OF CORRECTION

| | | |
|---|---|---|
| PATENT NO. | : 7,148,229 B2 | Page 1 of 1 |
| APPLICATION NO. | : 10/776697 | |
| DATED | : December 12, 2006 | |
| INVENTOR(S) | : Peter W. Dunten et al. | |

It is certified that error appears in the above-identified patent and that said Letters Patent is hereby corrected as shown below:

Title Page, (73) Assignee: delete "Hoffman-La Roche Inc., Nutley, NJ (US)" and insert -- Hoffmann-La Roche Inc., Nutley, NJ (US) --

Column 99, Claim 1, line 51, delete "salt or prodrug" and insert -- salts or prodrugs --

Column 99, Claim 4, line 56, delete "compounds" and insert -- compound --

Column 100, Claim 7, line 1, delete "A compounds" and insert -- A compound --

Column 100, Claim 14, line 47, delete "A compounds" and insert -- A compound --

Column 103, Claim 33, line 16, delete "A compound" and insert -- The compounds --

Signed and Sealed this

Twenty-eighth Day of August, 2007

JON W. DUDAS
*Director of the United States Patent and Trademark Office*